United States Patent
Moskovich et al.

(10) Patent No.: US 7,836,539 B2
(45) Date of Patent: Nov. 23, 2010

(54) ORAL CARE IMPLEMENT

(75) Inventors: Robert Moskovich, East Brunswick, NJ (US); Bruce Russell, Howell, NJ (US); Luca Casini, Milan (IT); Douglas Hohlbein, Pennington, NJ (US); Thomas Küchler, Schliern (CH); Tanja Langgner, London (GB); Thomas Mintel, Rahway, NJ (US); Michael Rooney, Milburn, NJ (US); Joachim Storz, Zell am See (AT)

(73) Assignee: Colgate-Palmolive Company, New York, NY (US)

( * ) Notice: Subject to any disclaimer, the term of this patent is extended or adjusted under 35 U.S.C. 154(b) by 1433 days.

(21) Appl. No.: 11/122,245

(22) Filed: May 5, 2005

(65) Prior Publication Data

US 2006/0195995 A1 Sep. 7, 2006

Related U.S. Application Data

(63) Continuation-in-part of application No. 10/768,363, filed on Jan. 30, 2004, now Pat. No. 7,703,163, (Continued)

(60) Provisional application No. 60/414,117, filed on Sep. 27, 2002, provisional application No. 60/418,776, filed on Oct. 6, 2002, provisional application No. 60/419,425, filed on Oct. 18, 2002, provisional application No. 60/412,290, filed on Sep. 20, 2002, provisional application No. 60/402,162, filed on Aug. 9, 2002, provisional application No. 60/402,170, filed on Aug. 9, 2002, provisional application No. 60/402,670, filed on Aug. 12, 2002, provisional application No. 60/402,165, filed on Aug. 9, 2002.

(51) Int. Cl.
*A61B 17/24* (2006.01)

(52) U.S. Cl. .......................... 15/111; 15/167.1; 606/161

(58) Field of Classification Search ................ 15/167.1, 15/111, 110, 143.1; 606/161; 601/139, 141–142; D24/147

See application file for complete search history.

(56) References Cited

U.S. PATENT DOCUMENTS 585,358 A 6/1897 Gould (Continued)

FOREIGN PATENT DOCUMENTS

CH 99738 6/1923

(Continued)

OTHER PUBLICATIONS

Substantive Examination Adverse Report from the Patent Office of Malaysia for counterpart Malaysian Patent Application No. PI20055377 dated Jan. 29, 2010; references relied on therein are of record in the present application.

(Continued)

*Primary Examiner*—Laura C Guidotti
(74) *Attorney, Agent, or Firm*—Amy M. Fernandez

(57) ABSTRACT

An oral care implement is provided having a handle and a head with a soft tissue cleanser and/or tooth cleaning elements. The tissue cleanser may include a plurality of projections for cleaning the soft tissue, which may include cleaning between the papillae of a user's tongue. The soft tissue cleanser may have an elongate ridge projecting from the head in generally the same direction as the projections. The handle may include a base with a gripping region and a projection protruding from the base in the gripping region. The handle may also have a grip surface with a plurality of spaced slot openings exposing portions of the base. The grip body may form opposite finger grips on the handle.

19 Claims, 52 Drawing Sheets

Related U.S. Application Data

(63) which is a continuation-in-part of application No. 10/697,213, filed on Oct. 30, 2003, application No. 11/122,245, filed on May 5, 2005, which is a continuation-in-part of application No. 11/019,671, filed on Dec. 23, 2004, which is a continuation-in-part of application No. 10/869,922, filed on Jun. 18, 2004, now Pat. No. 7,143,462, which is a continuation-in-part of application No. 10/601,106, filed on Jun. 20, 2003, now abandoned, said application No. 11/019,671 is a continuation-in-part of application No. PCT/US03/30633, filed on Sep. 26, 2003, which is a continuation-in-part of application No. PCT/US03/29497, filed on Sep. 17, 2003, which is a continuation-in-part of application No. 29/189,729, filed on Sep. 10, 2003, now Pat. No. Des. 517,812, and a continuation-in-part of application No. 10/989,267, filed on Nov. 17, 2004, now Pat. No. 7,607,189, which is a continuation-in-part of application No. 29/209,242, filed on Jul. 14, 2004, now abandoned, and a continuation-in-part of application No. 29/209,244, filed on Jul. 14, 2004, now abandoned, application No. 11/122,245, filed on May 5, 2005, which is a continuation-in-part of application No. 10/902,257, filed on Jul. 30, 2004, now Pat. No. 7,047,591, which is a continuation-in-part of application No. PCT/US03/29497, filed on Sep. 17, 2003, said application No. 10/902,257 application No. 11/122,245, filed on May 5, 2005, is a continuation-in-part of application No. 11/053,583, filed on Feb. 8, 2005, now Pat. No. 7,360,270, which is a continuation-in-part of application No. 11/053,589, filed on Feb. 8, 2005, which is a continuation of application No. PCT/US03/24878, filed on Aug. 8, 2003.

(56) References Cited

U.S. PATENT DOCUMENTS

| | | |
|---|---|---|
| 697,336 A | 4/1902 | Hagerty |
| 726,727 A | 4/1903 | Mills |
| 864,054 A | 5/1907 | Peck |
| 907,842 A | 12/1908 | Meuzies |
| 1,002,468 A | 9/1911 | Strangman |
| 1,006,630 A | 10/1911 | Clarke |
| 1,125,532 A | 1/1915 | Himmel |
| 1,128,139 A | 2/1915 | Hoffman |
| 1,142,698 A | 6/1915 | Crumbaugh |
| 1,153,409 A | 9/1915 | Wheeler |
| 1,191,556 A | 7/1916 | Blake |
| 1,251,250 A | 12/1917 | Libby |
| 1,268,544 A | 6/1918 | Cates |
| 1,405,279 A | 1/1922 | Cassedy |
| 1,470,710 A | 10/1923 | Davis |
| 1,495,675 A | 5/1924 | Colt |
| 1,598,224 A | 8/1926 | Van Sant |
| 1,658,706 A | 2/1928 | Carrott |
| D75,971 S | 8/1928 | Faubert et al. |
| 1,704,564 A | 3/1929 | Friedland |
| 1,705,109 A | 3/1929 | Essbach |
| 1,728,956 A | 9/1929 | Darmitzel |
| 1,741,143 A | 12/1929 | Chin |
| 1,796,001 A | 3/1931 | Church |
| 1,816,582 A | 7/1931 | Heron |
| 1,817,585 A | 8/1931 | Samuel |
| 1,860,924 A | 5/1932 | Cooke |
| 1,861,347 A | 5/1932 | Johnson |
| 1,872,832 A | 8/1932 | Silverberg |
| 1,891,864 A | 12/1932 | Barrett |
| 1,892,068 A | 12/1932 | Metzler |
| 1,903,161 A | 3/1933 | Barkan |
| 2,083,217 A | 7/1934 | Brothers et al. |
| 1,993,662 A | 3/1935 | Green |
| 1,993,763 A | 3/1935 | Touchstone |
| D99,352 S | 4/1936 | Grapp |
| 2,042,239 A | 5/1936 | Planding |
| 2,049,956 A | 8/1936 | Greenberg |
| 2,059,914 A | 11/1936 | Rosenberg |
| 2,079,728 A | 5/1937 | Arnold |
| 2,129,082 A | 9/1938 | Byrer |
| 2,161,349 A | 6/1939 | Hadden |
| 2,186,005 A | 1/1940 | Casto |
| 2,263,885 A | 5/1940 | McGauley |
| D122,815 S | 10/1940 | Crosby |
| 2,218,072 A | 10/1940 | Runnels |
| 2,225,331 A | 12/1940 | Campbell |
| 2,233,936 A | 3/1941 | Campbell |
| 2,253,210 A | 8/1941 | Pshiharis |
| 2,253,910 A | 8/1941 | Luenz |
| 2,263,802 A | 11/1941 | Grusin |
| 2,305,461 A | 12/1942 | Spyra |
| 2,364,205 A | 12/1944 | Fuller |
| 2,405,029 A | 7/1946 | Gallanty et al. |
| 2,418,485 A | 4/1947 | Shipley |
| 2,491,274 A | 12/1949 | McNeill |
| 2,512,059 A | 6/1950 | Haeusser |
| 2,651,068 A | 11/1950 | Seko |
| 2,543,999 A | 3/1951 | Voss |
| D162,941 S | 4/1951 | Ehrman |
| 2,554,777 A | 5/1951 | Dangin |
| 2,574,654 A | 11/1951 | Moore |
| 2,583,750 A | 1/1952 | Runnels |
| 2,642,604 A | 6/1953 | Ferrari |
| 2,708,762 A | 6/1953 | Kling et al. |
| 2,686,325 A | 8/1954 | Silver |
| 2,702,914 A | 3/1955 | Kittle et al. |
| 3,103,680 A | 9/1963 | Krichmar |
| 3,153,800 A | 10/1964 | Trotin |
| 3,181,193 A | 5/1965 | Nobles et al. |
| 3,185,582 A | 5/1965 | Viator |
| 3,195,537 A | 7/1965 | Blasi |
| 3,254,356 A | 6/1966 | Yao et al. |
| 3,258,805 A | 7/1966 | Rossnan |
| 3,337,893 A | 8/1967 | Fine et al. |
| D213,669 S | 4/1969 | Miller |
| 3,509,874 A | 5/1970 | Stillman |
| 3,610,043 A | 10/1971 | Wemyss |
| 3,633,237 A | 1/1972 | Bagube |
| 4,299,208 A | 11/1981 | Blanc |
| 4,328,604 A | 5/1982 | Adams |
| 4,356,585 A | 11/1982 | Protell et al. |
| 4,364,142 A | 12/1982 | Pangle |
| D272,683 S | 2/1984 | Stocchi |
| D272,687 S | 2/1984 | Stocchi |
| D272,689 S | 2/1984 | Stocchi |
| D272,690 S | 2/1984 | Stocchi |
| D273,635 S | 5/1984 | Stocchi |
| 4,455,704 A | 6/1984 | Williams |
| 4,488,327 A | 12/1984 | Snider |
| 4,610,043 A | 9/1986 | Vezjak |
| D287,072 S | 12/1986 | Pfleger |
| 4,628,564 A | 12/1986 | Youssef |
| 4,721,021 A | 1/1988 | Kusznir |
| D295,695 S | 5/1988 | Golzari |
| 4,827,551 A | 5/1989 | Maser et al. |
| 4,888,844 A | 12/1989 | Maggs |
| D309,528 S | 7/1990 | Valenti |
| 5,005,246 A | 4/1991 | Yen-Hui |
| D317,986 S | 7/1991 | Huang |
| 5,027,796 A | 7/1991 | Linzey |
| 5,032,082 A | 7/1991 | Herrera |
| 5,040,260 A | 8/1991 | Michaels |
| 5,054,154 A | 10/1991 | Schiffer et al. |

| Patent No. | Date | Name |
|---|---|---|
| 5,120,225 A | 6/1992 | Amit |
| 5,165,761 A | 11/1992 | Dirksing |
| 5,176,427 A | 1/1993 | Weihrauch |
| D334,288 S | 3/1993 | Witzig-Jaggi |
| 5,226,197 A | 7/1993 | Nack et al. |
| 5,230,118 A | 7/1993 | Chamma |
| 5,242,235 A | 9/1993 | Li |
| 5,249,327 A | 10/1993 | Hing |
| 5,273,425 A | 12/1993 | Hoagland |
| 5,305,489 A | 4/1994 | Lage |
| 5,339,482 A | 8/1994 | Desimone et al. |
| D350,851 S | 9/1994 | Spence, Jr. |
| 5,355,546 A | 10/1994 | Scheier et al. |
| 5,392,483 A | 2/1995 | Heinzelman et al. |
| 5,396,678 A | 3/1995 | Bredall et al. |
| 5,398,369 A | 3/1995 | Heinzelman et al. |
| D358,938 S | 6/1995 | Schneider et al. |
| 5,438,726 A | 8/1995 | Leite |
| 5,445,825 A | 8/1995 | Copelan et al. |
| 5,483,722 A | 1/1996 | Scheier et al. |
| D368,163 S | 3/1996 | Overthun |
| 5,511,273 A | 4/1996 | Carroll |
| D371,680 S | 7/1996 | Juhlin et al. |
| 5,530,981 A | 7/1996 | Chen |
| 5,535,474 A | 7/1996 | Salazar |
| 5,570,487 A | 11/1996 | Schneider |
| D376,695 S | 12/1996 | Tveras |
| 5,584,690 A | 12/1996 | Maassarani |
| 5,604,951 A | 2/1997 | Shipp |
| 5,613,262 A | 3/1997 | Choy-Maldonado |
| 5,628,082 A | 5/1997 | Moskovich |
| 5,673,454 A | 10/1997 | Quintanilla et al. |
| D386,905 S | 12/1997 | Brady et al. |
| 5,709,004 A | 1/1998 | Paduano et al. |
| D390,706 S | 2/1998 | Hohlbein et al. |
| D391,769 S | 3/1998 | Kling et al. |
| 5,735,011 A | 4/1998 | Asher |
| 5,735,012 A | 4/1998 | Heinzelman et al. |
| 5,735,864 A | 4/1998 | Heisinger, Jr. |
| 5,758,380 A | 6/1998 | Vrignaud |
| 5,765,252 A | 6/1998 | Carr |
| 5,766,193 A | 6/1998 | Millner |
| D396,288 S | 7/1998 | Samuel |
| 5,778,475 A | 7/1998 | Garcia |
| 5,778,476 A | 7/1998 | Savillaci et al. |
| 5,779,654 A | 7/1998 | Foley et al. |
| 5,781,958 A | 7/1998 | Meessmann et al. |
| D397,219 S | 8/1998 | Rangel et al. |
| 5,792,159 A | 8/1998 | Amin |
| 5,802,656 A | 9/1998 | Dawson et al. |
| 5,810,856 A | 9/1998 | Tveras |
| D399,349 S | 10/1998 | Barth |
| 5,817,114 A | 10/1998 | Anderson et al. |
| 5,818,856 A | 10/1998 | Injeyan et al. |
| D401,069 S | 11/1998 | Lamond et al. |
| 5,839,149 A | 11/1998 | Scheier et al. |
| D402,116 S | 12/1998 | Magloff et al. |
| 5,842,247 A | 12/1998 | Decesare et al. |
| 5,845,358 A | 12/1998 | Woloch |
| D403,510 S | 1/1999 | Menke et al. |
| D404,205 S | 1/1999 | Hohlbein |
| D404,206 S | 1/1999 | Hohlbein |
| 5,860,183 A | 1/1999 | Kam |
| D405,272 S | 2/1999 | Khalaj et al. |
| D407,221 S | 3/1999 | Van Gelder |
| D407,222 S | 3/1999 | Van Gelder |
| D407,223 S | 3/1999 | Van Gelder |
| 5,875,510 A | 3/1999 | Lamond et al. |
| 5,896,614 A | 4/1999 | Flewitt |
| 5,908,038 A | 6/1999 | Bennett |
| 5,913,346 A | 6/1999 | Narwani |
| 5,915,433 A | 6/1999 | Hybler |
| D412,064 S | 7/1999 | Achepohl et al. |
| 5,920,941 A | 7/1999 | Iannotta |
| 5,926,901 A | 7/1999 | Tseng et al. |
| 5,928,254 A | 7/1999 | Jensen |
| 5,930,860 A | 8/1999 | Shipp |
| 5,938,673 A | 8/1999 | DePierro et al. |
| D413,728 S | 9/1999 | Waguespack et al. |
| 5,946,759 A | 9/1999 | Cann |
| 5,951,578 A | 9/1999 | Jensen |
| 5,957,942 A | 9/1999 | Yudelman |
| D415,352 S | 10/1999 | Beals et al. |
| 5,967,152 A | 10/1999 | Rimkus |
| 5,970,564 A | 10/1999 | Inns et al. |
| D416,685 S | 11/1999 | Overthun |
| 5,980,541 A | 11/1999 | Tenzer |
| 5,980,542 A | 11/1999 | Saldivar |
| 5,984,935 A | 11/1999 | Welt et al. |
| 6,004,334 A | 12/1999 | Mythen |
| D418,979 S | 1/2000 | Moskovich et al. |
| D419,304 S | 1/2000 | Moskovich et al. |
| 6,015,293 A | 1/2000 | Rimkus |
| D419,773 S | 2/2000 | Beals et al. |
| D420,515 S | 2/2000 | Van Gelder |
| D420,802 S | 2/2000 | Cheong et al. |
| D420,804 S | 2/2000 | Juhlin et al. |
| D421,184 S | 2/2000 | Koh et al. |
| D421,841 S | 3/2000 | Achepohl et al. |
| D421,844 S | 3/2000 | Stark et al. |
| 6,032,315 A | 3/2000 | Liebel |
| 6,041,467 A | 3/2000 | Roberts et al. |
| D422,413 S | 4/2000 | Goldinger et al. |
| 6,049,936 A | 4/2000 | Holley |
| D423,785 S | 5/2000 | Karallis |
| D423,786 S | 5/2000 | Zelinski |
| D423,787 S | 5/2000 | Musciano |
| D424,808 S | 5/2000 | Beals et al. |
| D424,809 S | 5/2000 | Bernard |
| D425,306 S | 5/2000 | Beals et al. |
| 6,058,541 A | 5/2000 | Masterman et al. |
| D428,702 S | 8/2000 | Van Gelder |
| D429,566 S | 8/2000 | Yoshimoto et al. |
| D429,567 S | 8/2000 | Yoshimoto et al. |
| 6,098,233 A | 8/2000 | Chen |
| 6,105,191 A | 8/2000 | Chen et al. |
| 6,108,849 A | 8/2000 | Weihrauch |
| 6,108,851 A | 8/2000 | Bredall et al. |
| 6,108,869 A | 8/2000 | Meessmann et al. |
| 6,119,296 A | 9/2000 | Noe et al. |
| 6,131,228 A | 10/2000 | Chen et al. |
| D434,906 S | 12/2000 | Beals et al. |
| 6,171,323 B1 | 1/2001 | Potti et al. |
| 6,179,503 B1 | 1/2001 | Taghavi-Khanghah |
| D439,412 S | 3/2001 | Volpenhein et al. |
| D440,767 S | 4/2001 | Moskovich et al. |
| D441,958 S | 5/2001 | Rueb |
| 6,254,390 B1 | 7/2001 | Wagner |
| 6,260,227 B1 | 7/2001 | Fulop |
| D446,021 S | 8/2001 | Jen |
| D447,238 S | 8/2001 | Tang |
| 6,276,020 B1 * | 8/2001 | Leversby et al. ........... 15/167.1 |
| 6,276,021 B1 | 8/2001 | Hohlbein |
| D448,174 S | 9/2001 | Harris et al. |
| 6,289,545 B1 | 9/2001 | Molster |
| D448,569 S | 10/2001 | Harris et al. |
| D448,570 S | 10/2001 | Harris et al. |
| D448,571 S | 10/2001 | Harris et al. |
| 6,298,516 B1 | 10/2001 | Beals et al. |
| D450,457 S | 11/2001 | Hohlbein |
| 6,319,332 B1 | 11/2001 | Gavney, Jr. et al. |
| 6,322,573 B1 | 11/2001 | Murayama |
| 6,332,233 B1 | 12/2001 | Proulx |
| D452,615 S | 1/2002 | Cheong et al. |
| D453,270 S | 2/2002 | Choong |
| 6,345,405 B1 | 2/2002 | Brackin |

| | | | | | | |
|---|---|---|---|---|---|---|
| D453,998 S | 3/2002 | Ping | | D503,538 S | 4/2005 | Desalvo |
| D454,252 S | 3/2002 | Lee | | 6,886,207 B1 | 5/2005 | Solanki |
| 6,352,545 B1 | 3/2002 | Wagner | | 6,895,629 B1 | 5/2005 | Wenzler |
| 6,353,958 B2 | 3/2002 | Weihrauch | | 2001/0023516 A1 | 9/2001 | Driesen et al. |
| RE37,625 E | 4/2002 | Wieder et al. | | 2001/0014232 A1 | 11/2001 | Ichimura |
| D456,139 S | 4/2002 | Hohlbein | | 2001/0041903 A1 | 11/2001 | Richard |
| 6,374,448 B2 | 4/2002 | Seifert | | 2001/0042280 A1 | 11/2001 | Moskovich et al. |
| D456,607 S | 5/2002 | Carlucci et al. | | 2001/0047556 A1 | 12/2001 | Weihrauch |
| D457,323 S | 5/2002 | Hohlbein | | 2002/0004964 A1 | 1/2002 | Luchino et al. |
| D457,325 S | 5/2002 | Wilson et al. | | 2002/0019645 A1 | 2/2002 | Fischer et al. |
| 6,383,202 B1 | 5/2002 | Rosenblood | | 2002/0100134 A1 | 8/2002 | Dunn et al. |
| D458,453 S | 6/2002 | Baertschi | | 2002/0108194 A1 | 8/2002 | Carlucci et al. |
| D459,086 S | 6/2002 | Belton et al. | | 2002/0124333 A1 | 9/2002 | Hafliger et al. |
| D459,087 S | 6/2002 | Pfleger | | 2002/0124337 A1 | 9/2002 | Calabrese et al. |
| 6,402,768 B1 | 6/2002 | Liebel | | 2002/0138926 A1 | 10/2002 | Brown, Jr. et al. |
| 6,408,476 B1 | 6/2002 | Cann | | 2002/0138928 A1 | 10/2002 | Calabrese |
| 6,421,867 B1 | 7/2002 | Weihrauch | | 2002/0138931 A1 | 10/2002 | Davies |
| D461,313 S | 8/2002 | Hohlbein | | 2002/0170145 A1 | 11/2002 | Stvartak et al. |
| D461,959 S | 8/2002 | Chan et al. | | 2003/0009837 A1 | 1/2003 | Cann |
| 6,440,149 B1 | 8/2002 | Potti | | 2003/0115699 A1 | 6/2003 | Wagstaff |
| D462,178 S | 9/2002 | Moskovich et al. | | 2003/0116884 A1 | 6/2003 | Wagstaff |
| D462,527 S | 9/2002 | Ping | | 2003/0163149 A1 | 8/2003 | Heisinger, Jr. |
| D462,528 S | 9/2002 | Crossman et al. | | 2003/0167582 A1 | 9/2003 | Fischer et al. |
| D463,131 S | 9/2002 | Winter et al. | | 2003/0196283 A1 | 10/2003 | Gatzemeyer et al. |
| D463,132 S | 9/2002 | Winter et al. | | 2003/0208865 A1 | 11/2003 | Davies |
| D463,133 S | 9/2002 | Hohlbein | | 2003/0216762 A1 | 11/2003 | Levit |
| 6,446,295 B1 | 9/2002 | Calabrese | | 2003/0229959 A1 | 12/2003 | Gavney et al. |
| 6,625,839 B2 | 9/2002 | Fischer | | 2004/0006837 A1 | 1/2004 | Cann |
| D463,668 S | 10/2002 | Yoshimoto et al. | | 2004/0010876 A1 | 1/2004 | Kraemer |
| D464,796 S | 10/2002 | Winter et al. | | 2004/0025272 A1 | 2/2004 | Stvartak et al. |
| 6,463,619 B2 | 10/2002 | Gavney, Jr. | | 2004/0025275 A1 | 2/2004 | Moskovich et al. |
| D465,847 S | 11/2002 | Jacobs | | 2004/0031115 A1 | 2/2004 | Gavney, Jr. |
| D466,302 S | 12/2002 | Ping | | 2004/0068810 A1 | 4/2004 | Lee |
| D467,430 S | 12/2002 | Ping | | 2004/0134007 A1 | 7/2004 | Davies |
| 6,496,999 B1 | 12/2002 | Gleason et al. | | 2004/0200748 A1 | 10/2004 | Klassen et al. |
| D469,958 S | 2/2003 | Saindon et al. | | 2004/0221409 A1 | 11/2004 | Gavney, Jr. |
| 6,513,182 B1 | 2/2003 | Calabrese et al. | | 2004/0231076 A1 | 11/2004 | Gavney, Jr. |
| D471,276 S | 4/2003 | Potti | | 2004/0237236 A1 | 12/2004 | Gavney, Jr. |
| 6,546,586 B2 | 4/2003 | Cho | | 2004/0255416 A1 | 12/2004 | Hohlbein |
| D474,608 S | 5/2003 | Hohlbein | | 2005/0000049 A1 | 1/2005 | Hohlbein |
| D475,531 S | 6/2003 | Klimeck et al. | | 2005/0015904 A1 | 1/2005 | Gavney, Jr. |
| D476,158 S | 6/2003 | Ling | | 2005/0038461 A1 | 2/2005 | Phillips |
| 6,571,417 B1 | 6/2003 | Gavney, Jr. | | 2005/0069372 A1 | 3/2005 | Hohlbein et al. |
| D476,487 S | 7/2003 | Saindon et al. | | 2006/0058821 A1* | 3/2006 | Jansheski ................ 606/161 |
| D477,465 S | 7/2003 | Reilly et al. | | | | |
| D478,211 S | 8/2003 | Ping | | FOREIGN PATENT DOCUMENTS | | |
| D478,213 S | 8/2003 | Ping | | | | |
| D478,424 S | 8/2003 | Saindon et al. | | CN | 1111535 A | 11/1995 |
| D478,425 S | 8/2003 | Ping | | CN | 99225704.2 | 2/1999 |
| D478,727 S | 8/2003 | Wong | | CN | 2377910 Y | 5/2000 |
| D478,728 S | 8/2003 | Wong | | DE | 857128 | 11/1952 |
| 6,601,272 B2 | 8/2003 | Stvartak et al. | | DE | 3114507 A1 | 3/1983 |
| D479,047 S | 9/2003 | Wong | | DE | 2930459 | 2/1989 |
| D479,914 S | 9/2003 | Choong | | DE | 3639424 A1 | 6/1998 |
| D480,213 S | 10/2003 | Ping | | EP | 0875169 A | 4/1998 |
| D480,214 S | 10/2003 | Kling et al. | | EP | 1 034 721 A | 9/2000 |
| D480,877 S | 10/2003 | Crossman et al. | | EP | 1308108 | 5/2003 |
| D482,199 S | 11/2003 | De Salvo | | FR | 53797.9 | 6/1922 |
| 6,647,581 B1 | 11/2003 | Persad et al. | | FR | 2594307 A1 | 4/1987 |
| D483,184 S | 12/2003 | Geiberger et al. | | GB | 17643 | 4/1912 |
| D483,568 S | 12/2003 | Jamson | | GB | 495982 | 11/1938 |
| D483,569 S | 12/2003 | Wong | | GB | 2371217 | 7/2002 |
| D485,989 S | 2/2004 | Winkler | | GB | 2391462 | 2/2004 |
| D486,649 S | 2/2004 | Sprosta et al. | | JP | 2000-278899 | 10/2000 |
| 6,687,940 B1 | 2/2004 | Gross et al. | | JP | 2000-308522 | 11/2000 |
| D487,195 S | 3/2004 | Winkler | | JP | 2001-314232 | 11/2001 |
| D488,621 S | 4/2004 | Wong | | JP | 2002-142867 | 5/2002 |
| 6,729,789 B2 | 5/2004 | Gordon | | SU | 1708283 | 1/1992 |
| 6,792,642 B2 | 9/2004 | Wagstaff | | WO | WO98/05241 | 2/1998 |
| 6,817,054 B2 | 11/2004 | Moskovich et al. | | WO | WO 98/08458 A | 3/1998 |
| 6,820,299 B2 | 11/2004 | Gavney, Jr. | | WO | WO98/09573 | 3/1998 |
| 6,859,969 B2 | 3/2005 | Gavney et al. | | WO | WO99/49754 A1 | 10/1999 |
| 6,865,767 B1 | 3/2005 | Gavney, Jr. | | WO | 0053054 A | 9/2000 |

| | | |
|---|---|---|
| WO | WO 00/64306 | 11/2000 |
| WO | WO 00/64307 | 11/2000 |
| WO | WO01/17433 A1 | 3/2001 |
| WO | WO01/45573 | 6/2001 |
| WO | WO 02/062174 A | 8/2002 |
| WO | WO 02/071967 A2 | 9/2002 |
| WO | WO03/030680 A | 4/2003 |
| WO | WO 2004/019801 A | 3/2004 |

OTHER PUBLICATIONS

International Search Report PCT/US2005/041384 Oct. 10, 2006.
Chinese Patent Office Action (References cited in the document) 200580046629.9 dated Mar. 6, 2005.

* cited by examiner

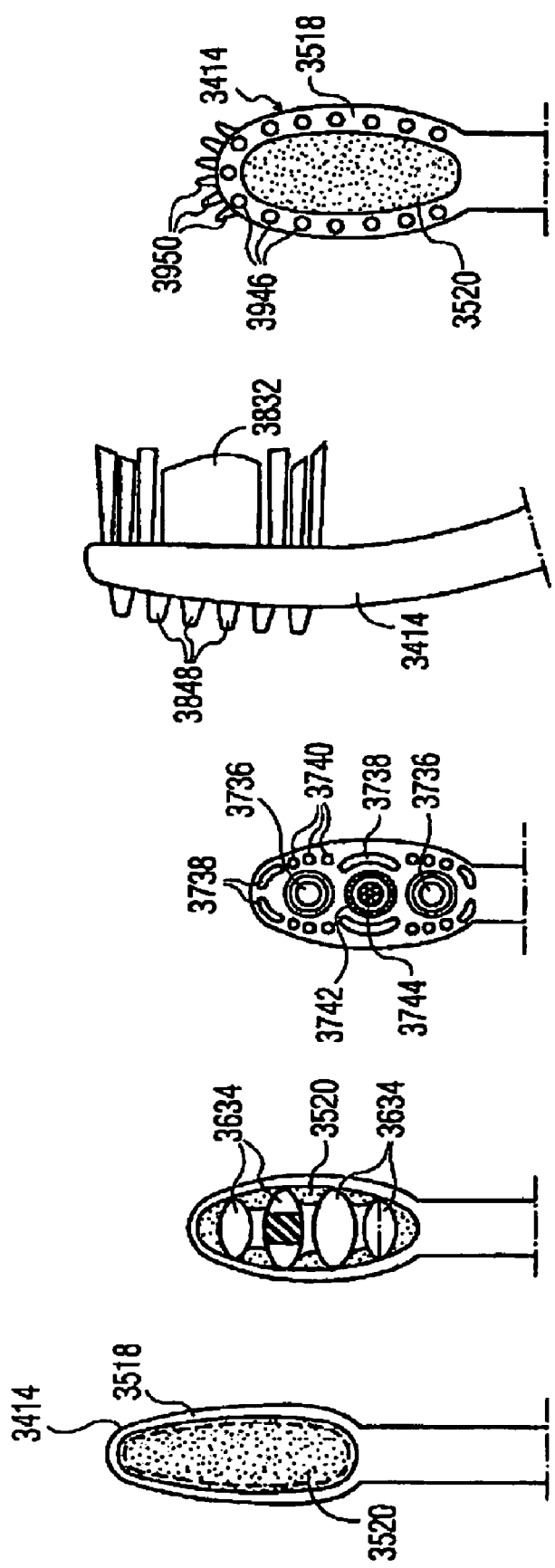

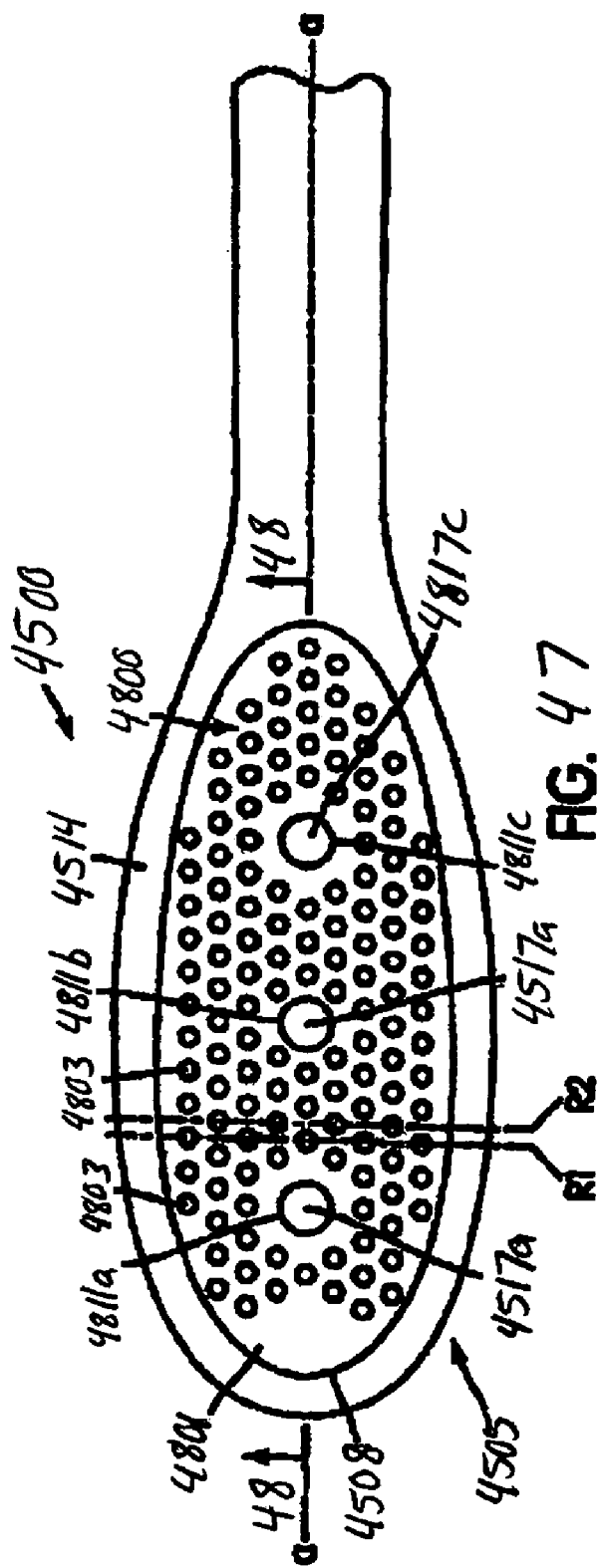
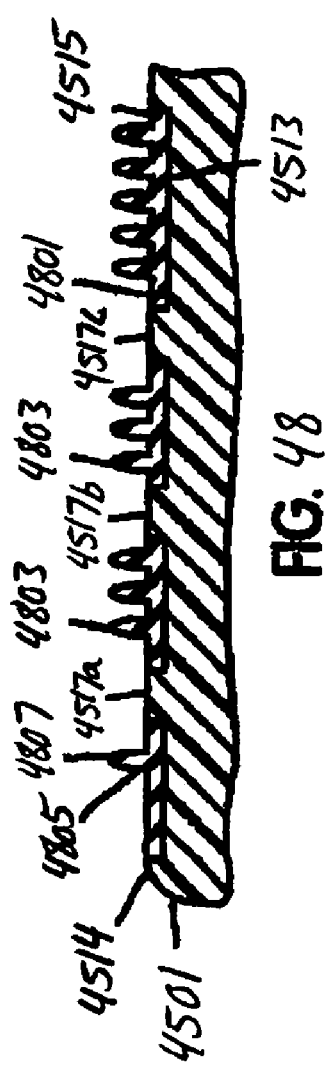
FIG. 47
FIG. 48

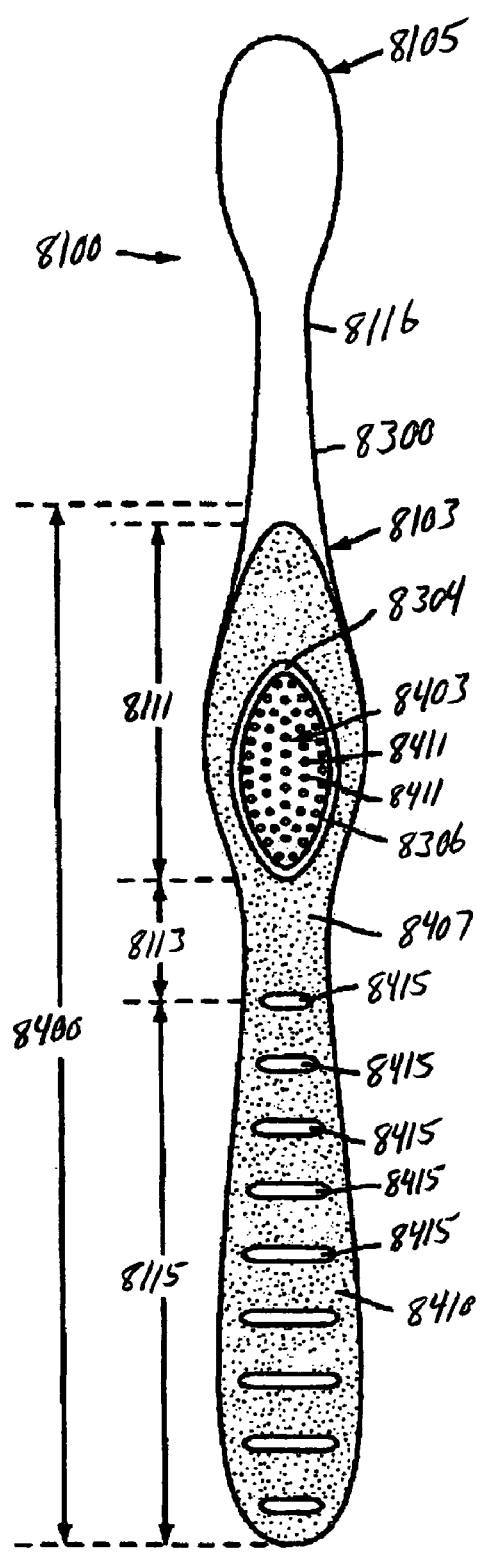
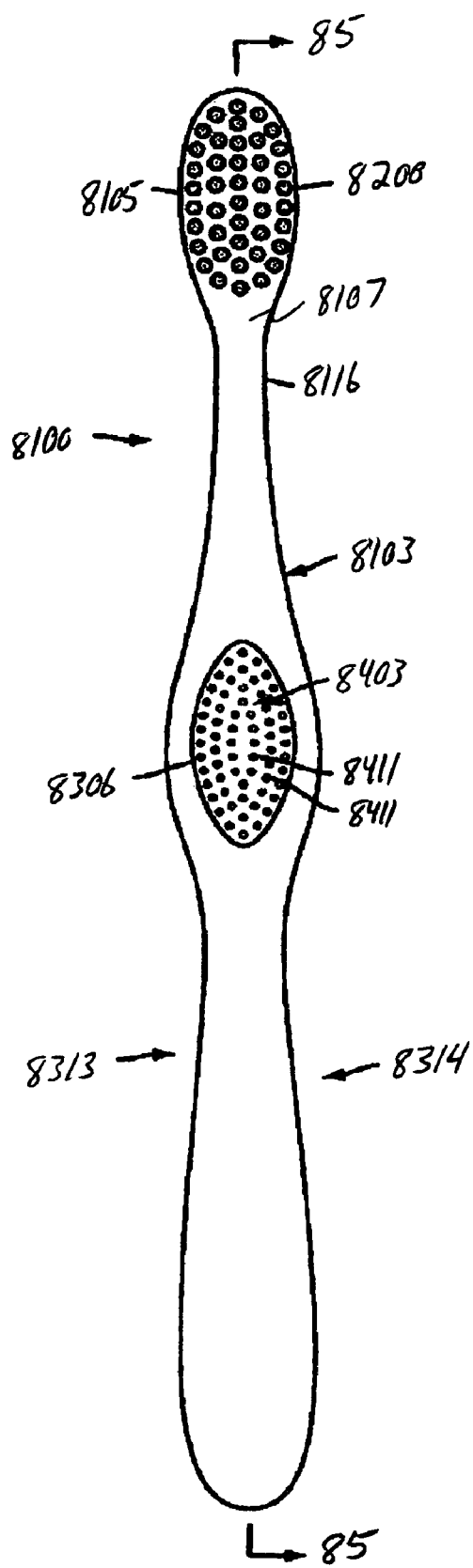
FIG. 82
FIG. 83

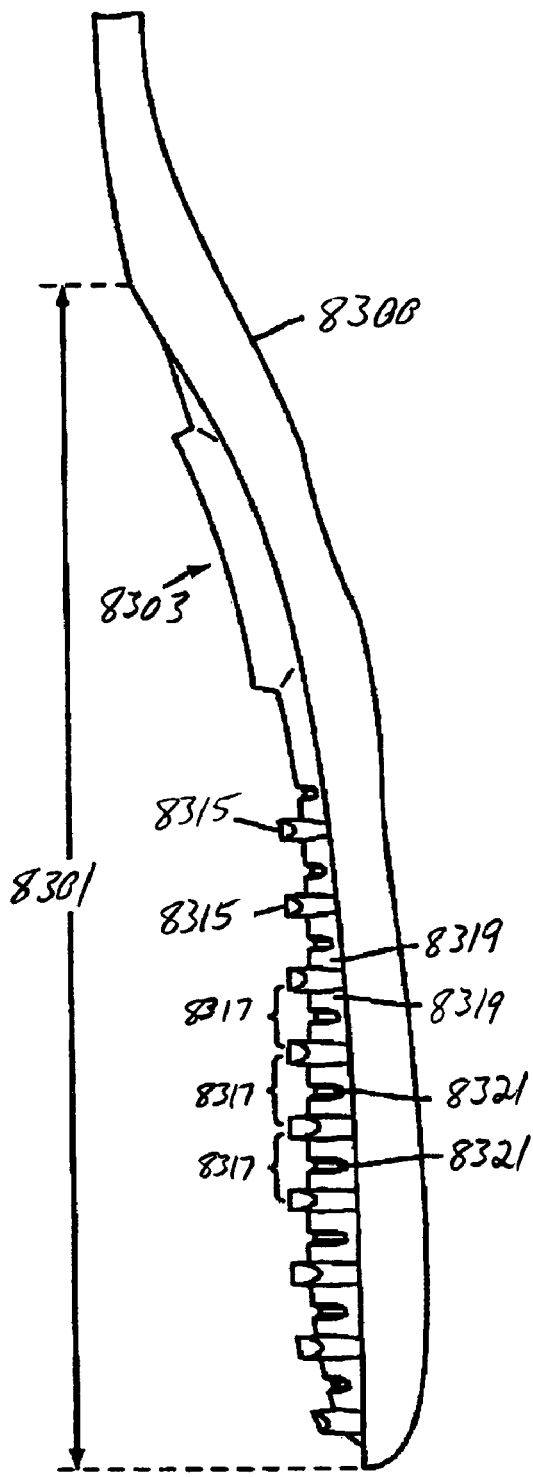
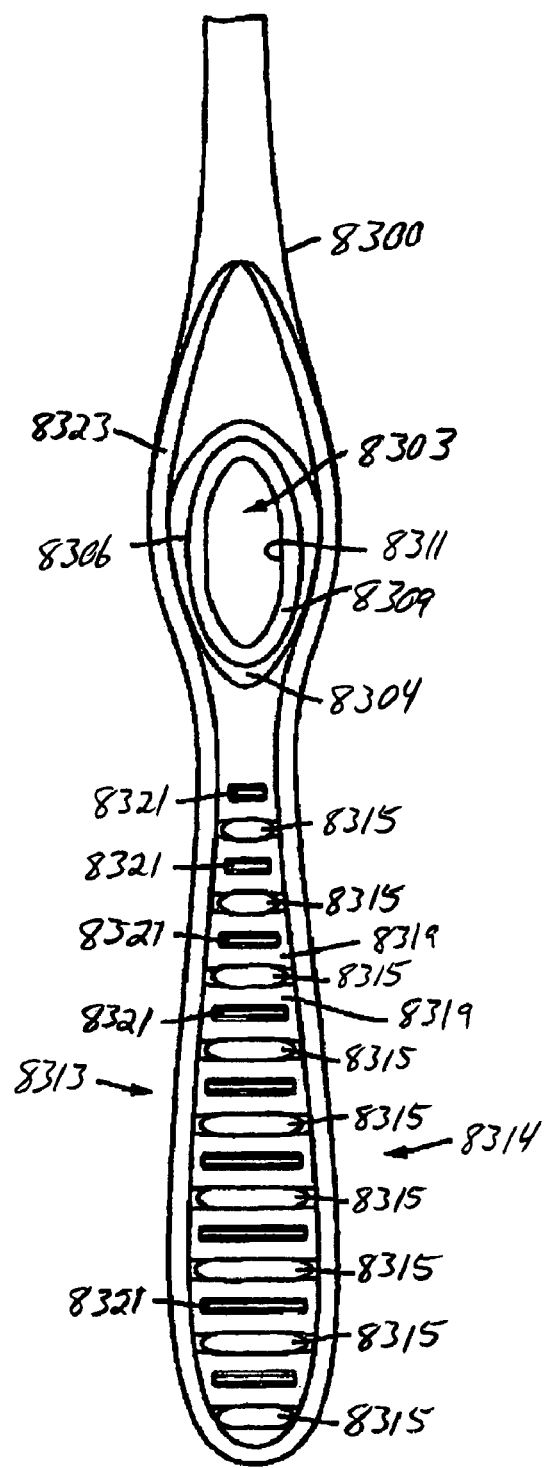
FIG. 86
FIG. 87

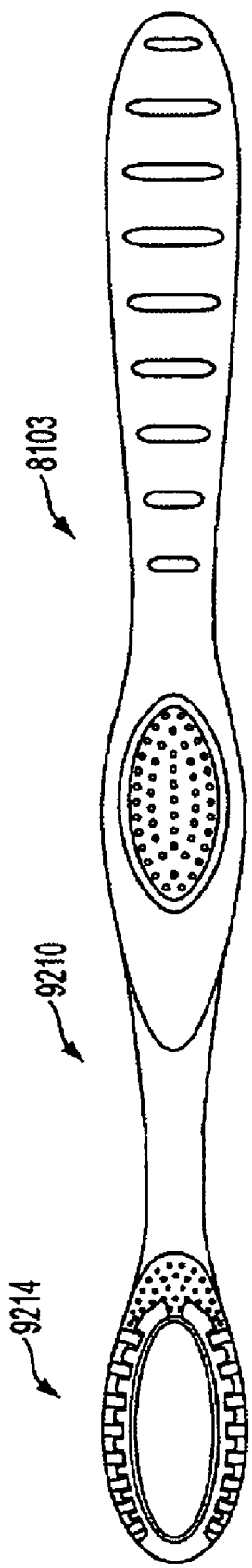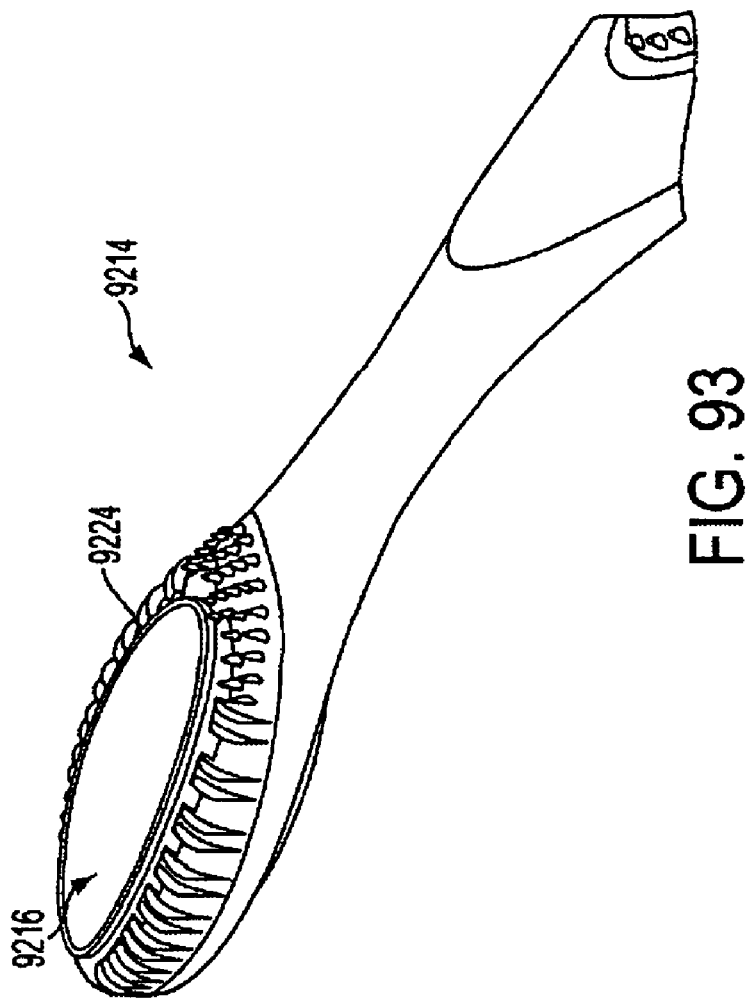
FIG. 92
FIG. 93

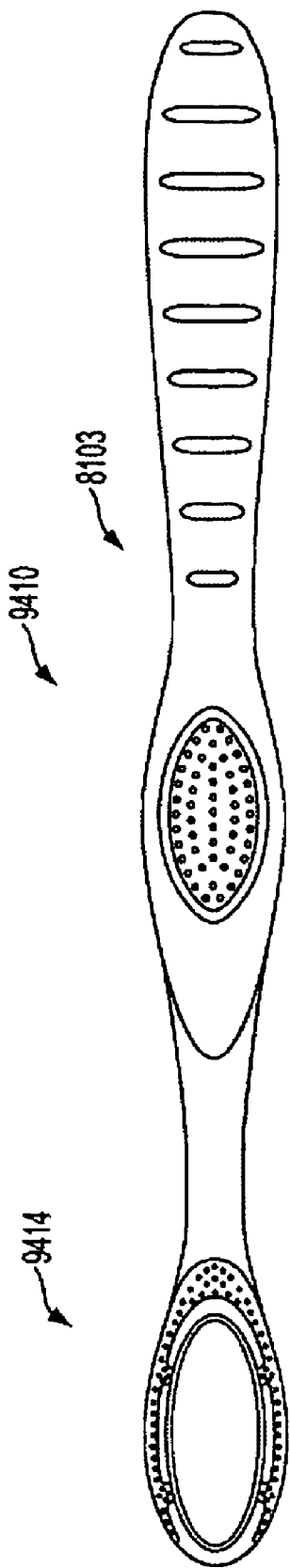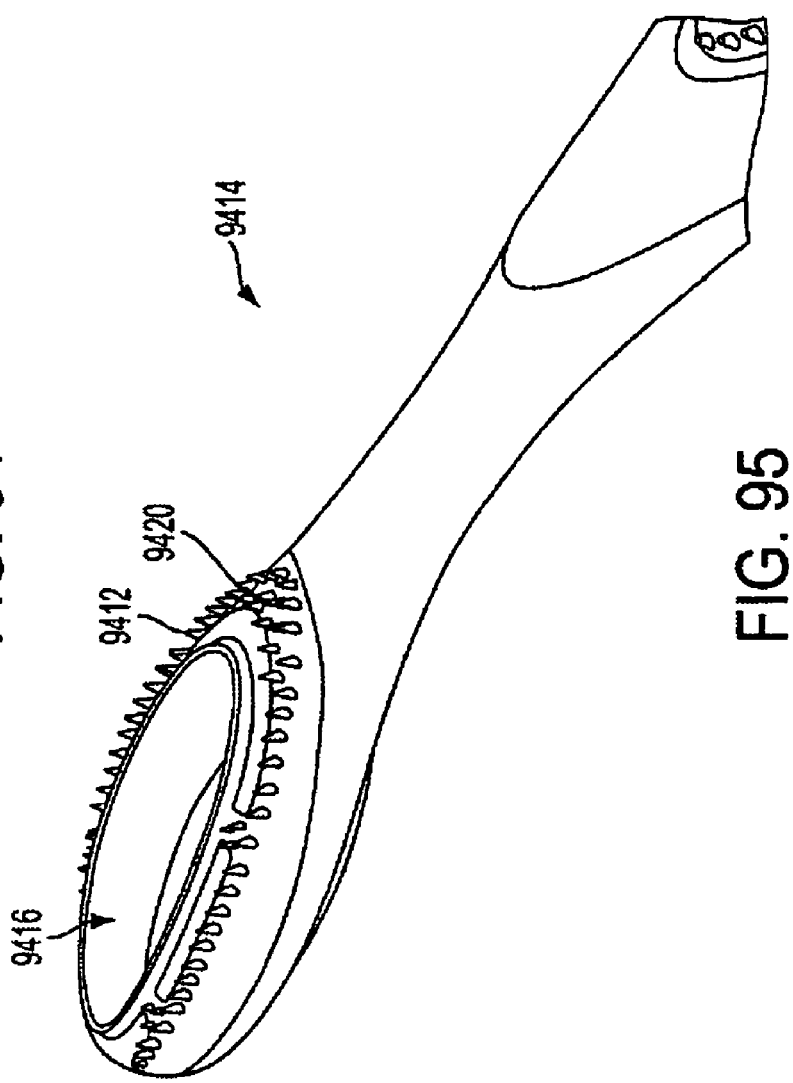
FIG. 94
FIG. 95

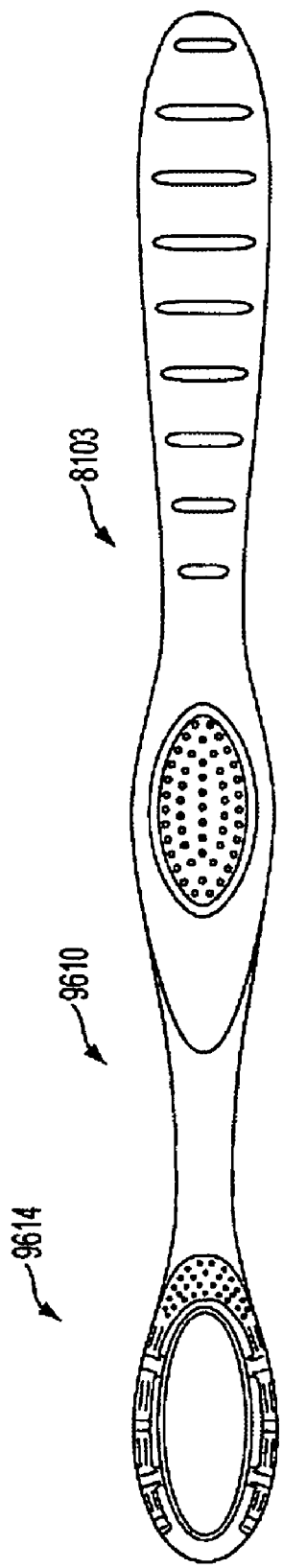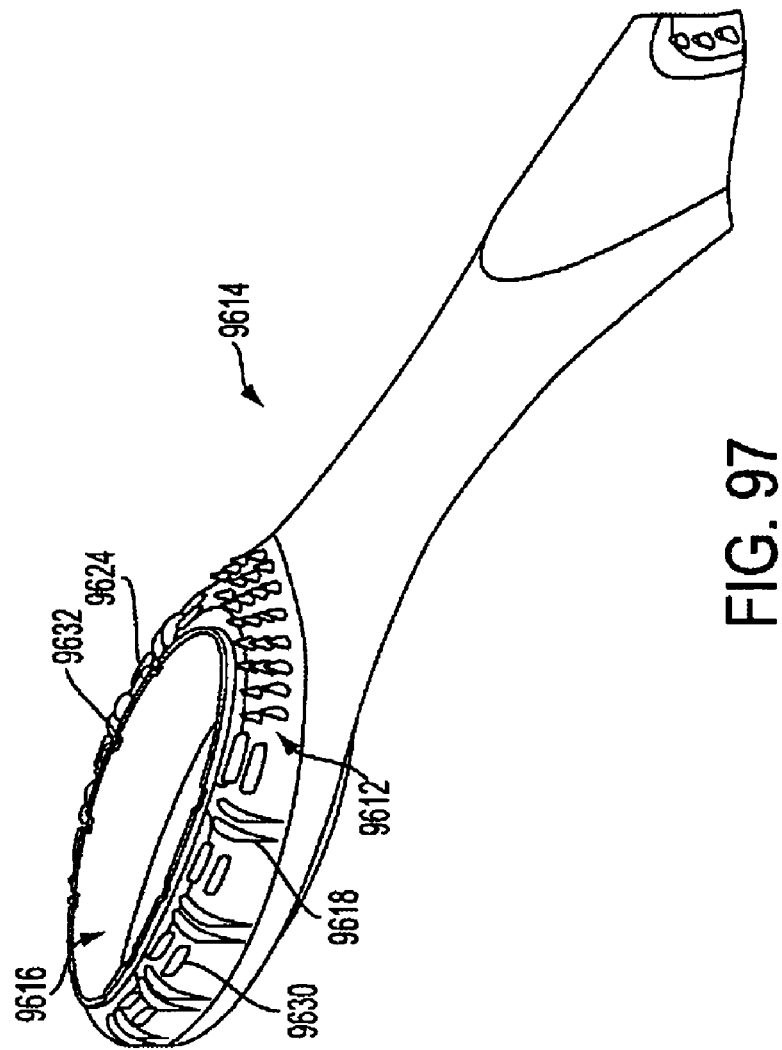

US 7,836,539 B2

ORAL CARE IMPLEMENT

CROSS-REFERENCE TO RELATED APPLICATIONS

This application is a continuation in part of U.S. patent application Ser. No. 10/768,363, filed Jan. 30, 2004, now U.S. Pat. No. 7,703,163 which is a continuation in part application of U.S. application Ser. No. 10/697,213, filed Oct. 30, 2003.

Further, this application is a continuation in part of co-pending U.S. patent application Ser. No. 11/019,671, filed Dec. 23, 2004, which: (1) is a continuation in part of U.S. patent application Ser. No. 10/869,922, filed Jun. 18, 2004, now U.S. Pat. No. 7,143,462 which is a continuation in part of U.S. patent application Ser. No. 10/601,106, filed Jun. 20, 2003; now abandoned (2) is a continuation in part of PCT patent application Ser. No. PCT/US03/030633 (designating the U.S.) filed Sep. 26, 2003, which claims the benefit of U.S. Provisional Application No. 60/414,117, filed Sep. 27, 2002, U.S. Provisional Application No. 60/418,776, filed Oct. 16, 2002, and U.S. Provisional Application No. 60/419,425, filed Oct. 18, 2002; (3) is a continuation in part of PCT patent application Ser. No. PCT/US2003/029497 (designating the U.S.), filed Sep. 17, 2003, which claims the benefit of U.S. Provisional Application No. 60/412,290, filed Sep. 20, 2002; (4) is a continuation in part of U.S. patent application Ser. No. 29/189,729, filed Sep. 10, 2003; now U.S. Pat. No. Des. 517,812 and (5) is a continuation-in-part of U.S. patent application Ser. No. 10/989,267, filed Nov. 17, 2004, now U.S. Pat. No. 7,607,189 which is a continuation-in-part application of U.S. patent application Ser. No. 29/209,242, filed Jul. 14, 2004 now abandoned.

Additionally, this application is a continuation in part application of U.S. application Ser. No. 10/989,267, 2004, filed Nov. 17, 2004, now U.S. Pat. No. 7,607,189 which is a continuation in part application of U.S. patent application Ser. No. 29/209,242, filed Jul. 14, 2004, now abandoned and a continuation in part application of U.S. patent application Ser. No. 29/209,244, filed Jul. 14, 2004 now abandoned.

Further, this application is a continuation in part application of U.S. application Ser. No. 10/902,257, 2004, filed Jul. 30, 2004, now U.S. Pat. No. 7,047,591 which (1) is a continuation in part of co-pending PCT Application No. PCT/US2003/029497 (designating the U.S.), filed Sep. 17, 2003, entitled "Toothbrush With Gripping Area", which claims priority of U.S. Provisional Application Ser. No. 60/412,290, filed Sep. 20, 2002; and (2) is a continuation in part of U.S. patent application Ser. No. 29/189,729, filed Sep. 10, 2003 now U.S. Pat. No. Des. 517,812.

In addition, this application is a continuation in part of U.S. patent application Ser. No. 11/053,583, filed Feb. 8, 2005, now U.S. Pat. No. 7,360,270 which is a continuation of International Patent Application No. PCT/US2003/024878 designating the U.S. filed Aug. 8, 2003 and published as International Publication No. WO2004/014181, which claims priority to U.S. Applications Ser. Nos. 60/402,162 filed Aug. 9, 2002, 60/402,170 filed Aug. 9, 2002 and 60/402,670 filed Aug. 12, 2002.

Further, this application is a continuation in part of U.S. patent application Ser. No. 11/053,589, filed Feb. 4, 2005, which is a continuation of International Patent Application No. PCT/US2003/024879 designating the U.S. filed Aug. 8, 2003 and published as International Publication No. WO2004/014182 on Feb. 19, 2004, which claims priority to U.S. Application Ser. No. 60/402,165 filed Aug. 9, 2002.

The contents of the above-noted applications are each expressly incorporated herein by reference.

FIELD OF THE INVENTION

The present invention pertains to an oral care implement having various features that may include a cleanser for cleaning soft tissue surfaces in a user's mouth, tooth cleaning or tooth treating elements, movable cleaning features, vibratory mechanisms, and/or handle gripping features.

BACKGROUND OF THE INVENTION

A variety of toothbrush configurations exist that have stationary and/or mechanically-driven movable cleaning elements. These conventional toothbrushes are dedicated to tooth cleaning/polishing operations and typically include a head portion directed to the cleaning/polishing operations, and a handle portion. The head typically has a flat or slightly altered surface to which the cleaning elements are attached, or to which mechanically-driven movable carriers for the cleaning elements are attached. The cleaning elements of these toothbrushes are configured for cleaning and/or for polishing a user's teeth, but are not configured for effective cleaning of soft tissue in a user's mouth, such as the user's tongue.

Tongue scrapers exist as devices for removing micro debris disposed on a user's tongue. Conventional tongue scrapers are stand-alone devices directed to the singular purpose of scraping a user's tongue. These conventional devices typically include a handle and scraper portion without including other cleaning elements.

Users manipulate conventional toothbrushes and tongue scrapers by grasping their handle portions. The handles are typically simple, linear rods of a relatively rigid material, which are neither comfortable for the user nor given to easy manipulation. As these devices are commonly used in wet conditions, their handles are often slippery during use.

Many people use multiple oral care implements, such as toothbrushes and tongue scrapers, on a daily basis to accomplish multiple oral care tasks. For instance, a user may use a toothbrush to clean his teeth and then use a tongue scraper to remove debris from his tongue. The user may then re-use the toothbrush to further clean his tongue. Thus, the user may switch between various oral care implements during a single session in a wet environment.

BRIEF SUMMARY OF THE INVENTION

The present invention pertains to an oral care implement that provides several advantages and that may be used for multiple functions. In one embodiment of the invention, an oral care implement is provided that has a soft tissue cleanser with a ring of projections for dislodging microbial and other debris from soft tissue of a user's mouth. The ring of projections may include nubs and ridges for engaging the soft tissue. The ring may border a central portion on a face of the oral care implement, which may have a depth in comparison with the height of the projections.

Embodiments of the invention may be multi-functional and include various combinations of features in advantageous combinations. Some embodiments include a soft tissue cleanser in combination with tooth cleaning features and/or in combination with gripping features on the handle that improve the user's grip and handling thereof. The embodiments may be manual or mechanically-driven devices, or combinations thereof. These and other aspects are discussed in relation to the following figures.

BRIEF DESCRIPTION OF THE DRAWINGS

A more complete understanding of the present invention and the advantages thereof may be acquired by referring to the following description in consideration of the accompanying drawings, in which like reference numbers indicate like features.

FIG. 35 is a front plan view showing the resilient cleaning field to which the cleaning/treating elements of FIG. 34 could be mounted.

FIGS. 36-37 are front plan views of different forms of cleaning heads in accordance with the invention.

FIG. 38 is a side elevational view of still yet another form of cleaning head in accordance with this invention.

FIG. 39 is a front plan view of a modified form of cleaning head in accordance with the invention.

FIG. 47 is a plan view of the oral care implement of FIG. 45 illustrating a tongue cleaning feature.

FIG. 48 is a partial section view of a head of the oral care implement of FIG. 45 taken along line 48-48 of FIG. 47.

FIG. 82 is a bottom plan view of the oral care implement of FIG. 81.

FIG. 83 is a top plan view of the oral care implement of FIG. 81.

FIG. 86 is a partial side view of a base of an oral care implement of FIG. 81.

FIG. 87 is a partial front view of the base of FIG. 86.

FIG. 92 is side view of a further oral care implement in accordance with the present invention.

FIG. 93 is partial perspective view of a head portion of the oral care implement of FIG. 92.

FIG. 94 is side view of a further oral care implement in accordance with the present invention.

FIG. 95 is partial perspective view of a head portion of the oral care implement of FIG. 94.

FIG. 96 is side view of a further oral care implement in accordance with the present invention.

FIG. 97 is partial perspective view of a head portion of the oral care implement of FIG. 96.

DETAILED DESCRIPTION OF THE INVENTION

Figure 1:
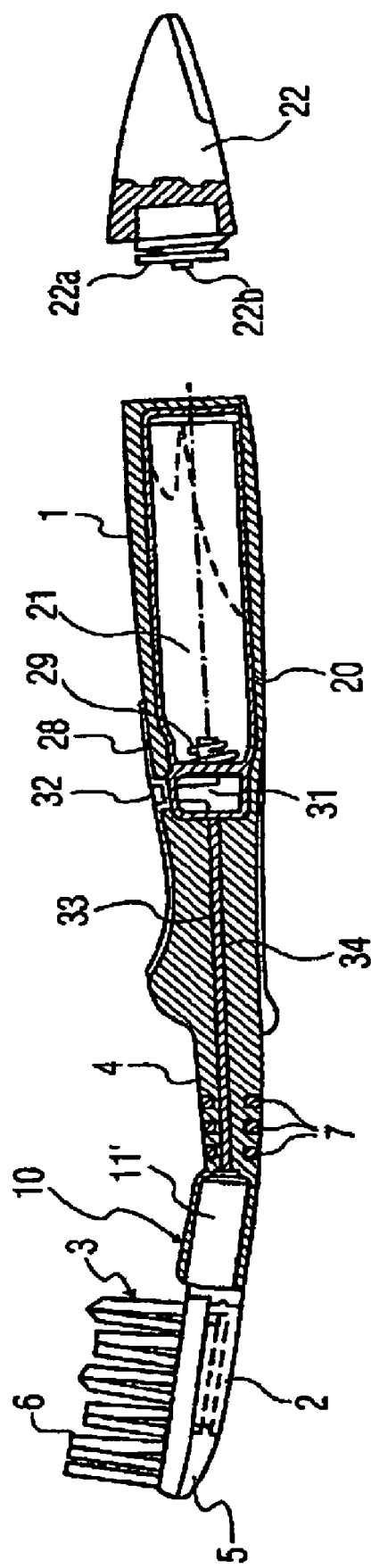
FIG. 1 shows a side view, partially in section, of an embodiment of a toothbrush according to the invention and of a handle-closure part separated from one another (without a battery).

The following embodiments describe aspects of the invention in the form of various oral care implement configurations that provide a variety of features and functions. Although these aspects are disclosed in the context of particular exemplary embodiments, the invention provides an oral care implement that includes one or more of the features described herein. The oral care implement may include a first feature described in one example configuration herein, as well as a second feature described in another example configuration herein.

In other words, the invention contemplates mixing and matching features from the disclosed embodiments in various combinations into a single oral care implement. The present invention thus makes it possible to select a combination of cleaning/treating element configurations, tissue cleanser configurations, handle features, gripping features, mechanical driving features, materials and orientations, etc. to achieve intended results, and to deliver additional oral health benefits, such as enhanced cleaning, tooth polishing, tooth whitening, tongue cleansing, massaging of gums, etc.

Oral care implements of various configurations are provided that generally include a handle and one or more cleaning features. The handle may include a mechanically-driven feature, such as rotating, vibrating, and/or moving cleaning elements. In one configuration, a toothbrush is provided with a mechanical vibratory element and a head having a plurality of different types of cleaning/treating elements and cleaning areas which provide for an enhanced cleaning and/or treating effects. The cleaning/treating elements move by the mechanical vibratory device and/or independently of the mechanical vibratory device. Such a toothbrush, therefore, provides for synergistic and enhanced cleaning, scrubbing and massaging experience on the teeth and gums.

A variety of toothbrush configurations are disclosed herein. One configuration is a toothbrush having multiple groupings of cleaning/treating elements that are uniquely mounted to the head of a toothbrush, which mounting facilitates flexible orientation of those groupings relative to the teeth and gums being cleaned. For example, the head of such a toothbrush could be designed to "wrap around" individual teeth resulting in deeper penetration of cleaning/treating elements between teeth. Such a configuration provides overall cleaning, for example, by independent movement of groups of cleaning/treating elements relative to the toothbrush head and each other.

In one example, a first group is a central grouping or "island" of cleaning/treating elements flexibly mounted to the toothbrush head. A second group is fixedly mounted to the toothbrush head in a configuration surrounding at least part of the central grouping. The central group is attached to the toothbrush head via, a flexible elastomeric membrane, resilient plastic straps, webbing or other material that flexibly interconnects the first group with the toothbrush head.

In another embodiment, the toothbrush head is divided into a plurality of separate cleaning areas. These areas include at least one and preferably two areas wherein the cleaning/treating elements are mounted to a base with other areas having the cleaning/treating elements mounted to pods wherein the pods have a greater degree of movability than do the bases. The pods are resilient so that during use, the cleaning/treating elements could be moved from their initial position and then returned to the initial position. The pods may be formed from a narrow or small diameter beam extending from the body of the toothbrush head to a cleaning/treating elements support pad. The narrow or small diameter beam may be enclosed in elastic material.

In one other configuration, a relatively non-movable base is located at each of the distal and proximal ends of the toothbrush head with at least two elastic pods mounted between the two bases. These various cleaning areas are separated from each other by channels extending completely across the head in a transverse direction.

This application further discloses a toothbrush configuration having multiple groupings of cleaning/treating elements ("islands") uniquely mounted to the head of a toothbrush, which mounting facilitates flexible orientation of those groupings relative to the teeth and gums being cleaned. More particularly, the groupings of cleaning/treating elements are mounted relative to the toothbrush head using a transverse, flexible membrane or web extending from the periphery of the cleaning/treating elements to the sidewalls of the toothbrush head. In one example, such flexible mounting facilitates 360 degree limited angle wobble of the cleaning/treating elements, which, in turn, orients the cleaning/treating elements towards the teeth even if the toothbrush head is not angled directly parallel to the user's teeth.

One exemplary toothbrush of this configuration includes a head in the form of a base having an upstanding wall to create a peripheral frame. In one embodiment, a thin resilient membrane or web is mounted within the frame. The membrane or web is capable of flexing to facilitate orientation of the cleaning/treating elements carried by the membrane relative to the teeth of the user.

The cleaning/treating elements may be bristles secured to the membrane or web by in-molded technology. Additional cleaning/treating elements can be arranged on the periphery of the "islands" to facilitate cleaning in those areas between the "islands". In a one embodiment, these additional cleaning/treating elements are fixedly mounted to the toothbrush head outside the periphery of the membrane or web flexibly holding the "islands" of cleaning/treating elements. This combination of flexible and fixed mounting of cleaning/treating elements provides very effective brushing of teeth and massaging of gums.

In use, for example, pressure applied to the toothbrush handle by a user causes a first group of cleaning/treating elements to contact the teeth being cleaned. As the force applied to the toothbrush exceeds a predetermined volume, a central group of cleaning/treating elements moves relative to the balance of the head. This movement, in turn, allows an outer group of fixed cleaning/treating elements to contact other areas of the teeth located at a greater distance from the head, including interproximal spaces between teeth.

This desired flexibility of the central grouping of cleaning/treating elements may be accomplished with an elastomeric bridge between the central movable group of cleaning/treating elements and the surrounding outer group of cleaning/treating elements. This elastomeric bridge may be continuous or maybe a series of independent bridges with a void between each bridge to encourage greater flexibility. The width of this bridge can be adjusted to vary the amount of force needed to push the central group of cleaning/treating elements into a position where the outer group can achieve their greatest cleaning potential.

In another toothbrush configuration, the gap between the groups of cleaning/treating elements corresponding to the width of the elastomeric bridge between them can effectively be filled with elastomeric wipers that move as force is applied to the central group of cleaning/treating elements. For example, tapered elastomeric wipers can be mounted to the elastomeric bridge so that the narrower tip of the wipers flex in ward and outward as force is applied to and released from the toothbrush handle. This wiping action further enhances the cleaning and treating functions of the toothbrush.

In a powered configuration, the toothbrush has a power source. The power source may be at least one battery, for example, 1, 2 or more batteries. The battery may be removable or fixed, rechargeable, non-rechargeable or rechargeable from an external source. Further, the battery may be of any size, such as, for example, AA, AAA, 9V and C. Alternatively, the power source may from an external source, for example via an AC adapter.

Figure 2:
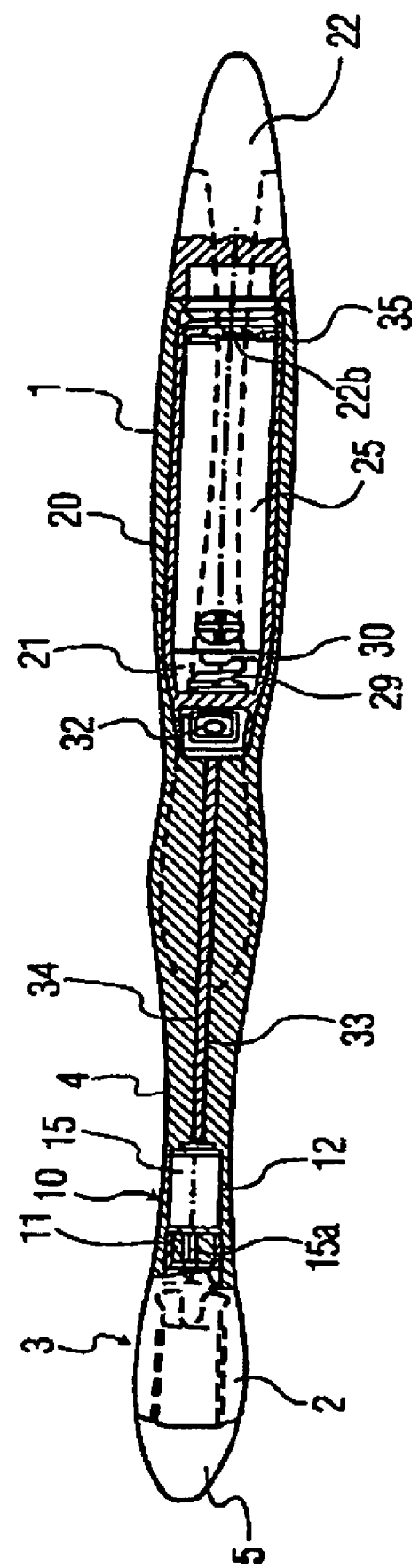
FIG. 2 shows a bottom view, partially in section, of another embodiment of a toothbrush according to the invention shown in the assembled state.
Figure 3:
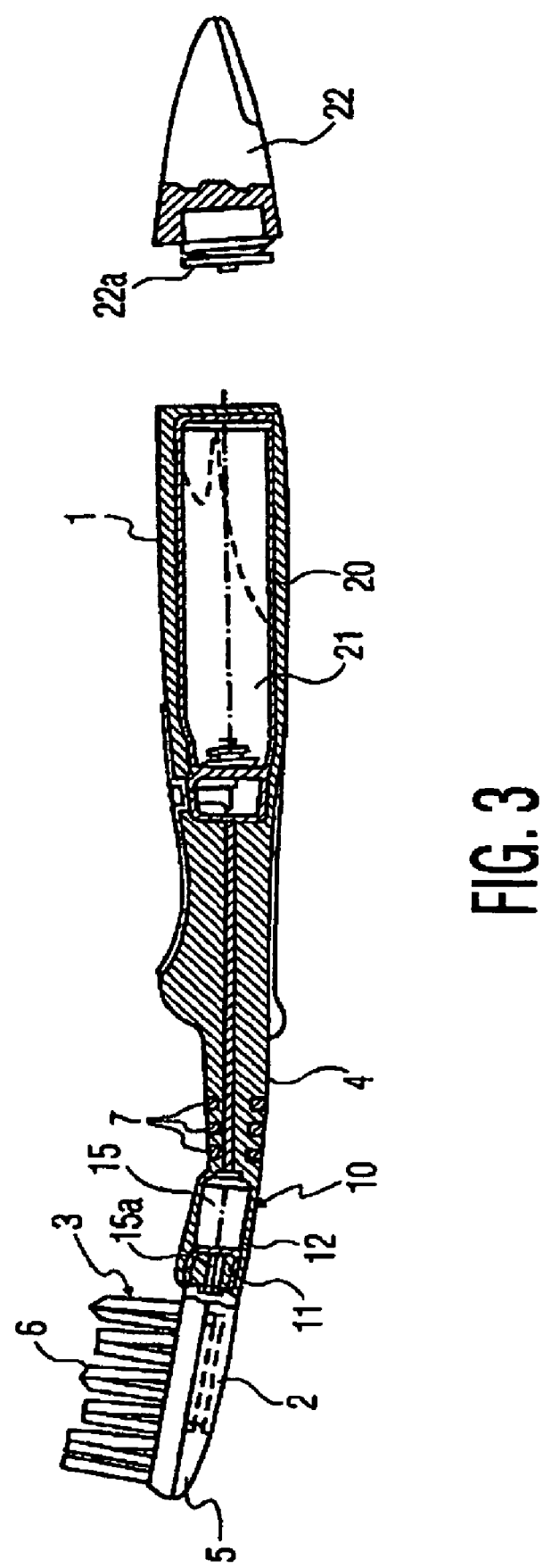
FIG. 3 shows a side view, partially in section, of the toothbrush according to FIG. 2 and the closure part separated from one another (without a battery).

Turning to the Figures, both the toothbrush illustrated in FIG. 1 and that according to FIGS. 2 and 3 each have a handle 1, a front bristle-carrying head part 3 and a neck part 4, which connects the head part 3 to the handle 1. The bristles combined to form clusters of bristles 6 are anchored in a bristle carrier 5 and form a profiled brushing surface with their free ends. In the embodiment illustrated, the bristle carrier 5 with the clusters of bristles 6 is positioned, in a manner which is known per se and thus is not described in detail, on a retaining part 2 of the head part 3 such that it can be exchanged. Also, as note above, any of the arrangements of teeth cleaning elements disclosed herein could be used in place of the illustrated bristle pattern.

The neck part 4 is provided with neck-part zones 7 which are preferably made of an elastically relatively compliant material component and provide for, or additionally increase, the elasticity of the neck part 4, with the result that, during use of the toothbrush, the bristle-carrying head part 3 can be forced back resiliently in the case of forces acting in the direction of the brushing surface. Optionally, the neck-part zones 7 are designed as notches which extend over part of the neck circumference and are filled with elastically compliant material (e.g., with a thermoplastic elastomer). It is understood that the form and number of neck-part zones can be different. It is also conceivable to have a flexible neck zone without using elastic material components, e.g., by providing constrictions or by way of a bellows.

Integrated in the front head part 3, or in that region of the neck part 4 which is adjacent to the head part 3, is a mechanical vibratory device 10, by means of which vibrations which effect or enhance the teeth-cleaning action may be imparted to the bristle-carrying head part 3. The vibratory device 10 can be connected to an electric power source, accommodated in the handle 1, via electrical connections running in the neck part 4, as is described herein below. In one embodiment, neck-part zones 7 are made of an elastically compliant material which dampens the vibration between the vibrating head part 3 and the handle 1, with the result that the vibratory action is produced, in particular, in the head part and is transmitted to the handle 1 to a slight extent. This means that slight vibrations can be felt in the handle 1 during the teeth-cleaning operation, and the toothbrush is thus comfortable to handle. In another embodiment, the vibration produced is not damped by the handle 1 and can act to full effect in the head part 3.Instead of the neck-part zones 7 having elastically compliant-material, however, other vibration-damping elements could also be used. Further, the dampening may also be achieved, for example, by using a basic material, by the neck part being configured in a particular form, for example by the presence of a bellows/accordion part, etc. Alternatively, the neck could be formed with reduced thickness and/or of dual materials as disclosed in U.S. patent application Ser. No. 11/053589, filed Feb. 4, 2005, which is incorporated herein by reference.

Accommodated in the handle 1 is a sheath or sleeve 20 which extends in the longitudinal direction of said handle and is made of electrically conductive material. Both the handle 1 and the sleeve 20 are open to the rear, this forming a cavity 21 which can be closed from the rear by a closure part 22 and into which it is possible to insert a battery 25, in the preferred embodiment illustrated a commercially available, non-rechargeable cylindrical battery, with a defined power (e.g. 1.5 V) as the power source for the vibratory device 10. It would also be possible, however, for a button cell or for a rechargeable storage battery to be used as the power source.

A spring contact 29 for the positive pole 30 of the battery 25 (see FIG. 2) is fitted in the sleeve 20, on a transverse wall 28, and is connected to the vibratory device 10 via an electric line 31, a switch 32, which is installed in the sleeve 20 and can be actuated from the outside of the handle 1, and an electric line 33 running in the neck part 4. The electrical connection can be interrupted by means of the switch 32.

The closure part 22 is provided with a threaded stub 22a made of an electrically conductive material and can be screwed into the handle 1 and/or into the sleeve 20 by way of said threaded stub. The threaded stub 22a is provided with a contact surface 22b which, with the closure part 22 screwed in, comes into abutment against the negative pole 35 of the battery 25 inserted into the sleeve 20. The negative pole 35 is electrically connected to the vibratory device 10 via the threaded stub 22a, the sleeve 20 itself and a line 34, which connects the sleeve 20 to the vibratory device 10 and runs in the neck part 4.

Instead of being transmitted via the electrically conductive sleeve 20, it would also be possible for the power to be transmitted in some other way, for example using wires or an electrically conductive plastic.

In the embodiment illustrated in FIG. 1, the vibratory device 10 comprises a vibratory element 11' which functions preferably in the manner of a vibratory armature, can be electrically connected directly to the power source via the lines 33, 34 and, with the power source connected, is made to vibrate.

In the case of the toothbrush variant illustrated in FIGS. 2 and 3, the vibratory device 10 comprises a vibratory element 11 in the form of an eccentric, which produces mechanical vibrations and can be rotated about an axis located in the longitudinal direction of the toothbrush, and also comprises a drive which is arranged directly adjacent and is designed as a micromotor 15. The vibratory element 11 is connected to the shaft 15a of the micromotor 15, which can be electrically connected to the power source via the lines 33, 34. The micromotor 15 and the eccentric may be accommodated as a structural unit in a housing 12.

Instead of an eccentric which can be driven in rotation, it would also be possible to have a vibratory element 11 which can be driven in a translatory manner. It would be possible, in the case of the toothbrush according to the invention, to arrange the bristle-carrying head part 3 such that it can be moved in relation to the neck part 4 in order for the latter, in the case of vibrations produced by means of the vibratory device 10, to be made to move in relation to the rest of the toothbrush.

The electric lines 31, 33, 34 could also be realized by electricity-conducting plastic tracks. The switch 32, which connects or interrupts the lines 31, 33, may also be, for example, a magnetic switch. A preferred configuration of the switch 32, however, has a pulse switch arranged on a printed circuit board as well as further electronic components which store the switching state.

It is also possible, however, for the electrical connection between the battery 25 and the vibratory element 11' (FIG. 1) or the drive 15 (FIGS. 2 and 3) to be produced or interrupted not by the switch 32, but by the closure part 22, which can be screwed into the handle and/or into the sleeve 20 or connected to the same in a bayonet-like manner, being turned (i.e., the switch 32 is dispensed with in the case of such a configuration).

Instead of the rear closure part 22 being screwed to the handle 1, it would, of course, also be possible to have some other type of releasable connection (e.g., plug-in connection, bayonet connection, etc.) and a corresponding configuration of the contact part interacting with the negative pole 35.

It would also be possible for the closure part 22 to be in a form which is quite different to that illustrated in the drawing. For example, the closure part could be provided with a set-down surface or a foot part and thus serve as an element on which the toothbrush can be set down.

Figure 4:
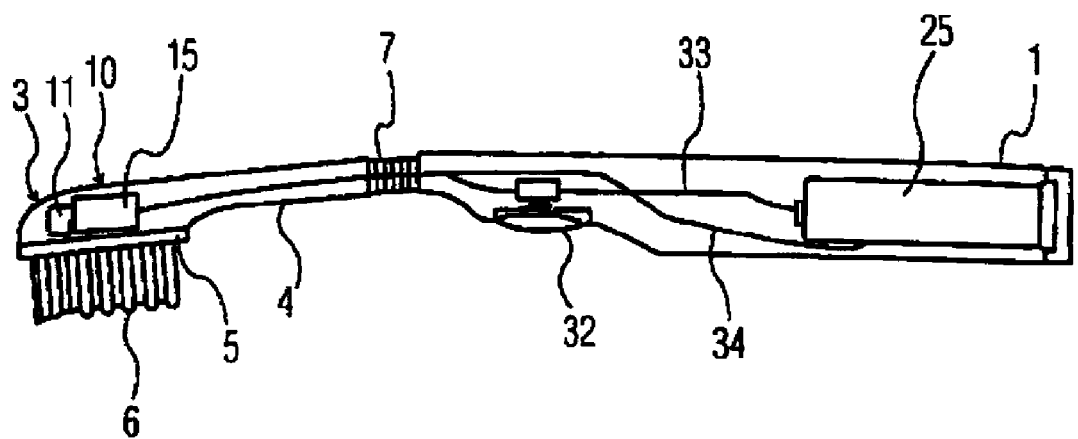
FIG. 4 shows a side view of a further embodiment of a toothbrush according to the invention shown in the assembled state.

The toothbrush illustrated in FIG. 4 corresponds essentially to that according to FIGS. 2 and 3. According to FIG. 4, the vibratory device 10 is arranged directly in the front head part 3. In this exemplary embodiment, the sleeve 20 is dispensed with; the battery 25 is connected directly to the vibratory device 10 via the lines 33, 34. It is also the case with this toothbrush that use is preferably made of an exchangeable bristle carrier 5, which can be positioned on a retaining part 2 of the head part 3, e.g., in the manner of a snap-in connection. The capacity for changing the bristle carrier 5 provided with the clusters of bristles 6 is particularly advantageous since the toothbrush provided with the vibratory device 10 can be used irrespective of the service life of the bristles, which is usually even shorter than the service life of the battery 25.

Figure 5:
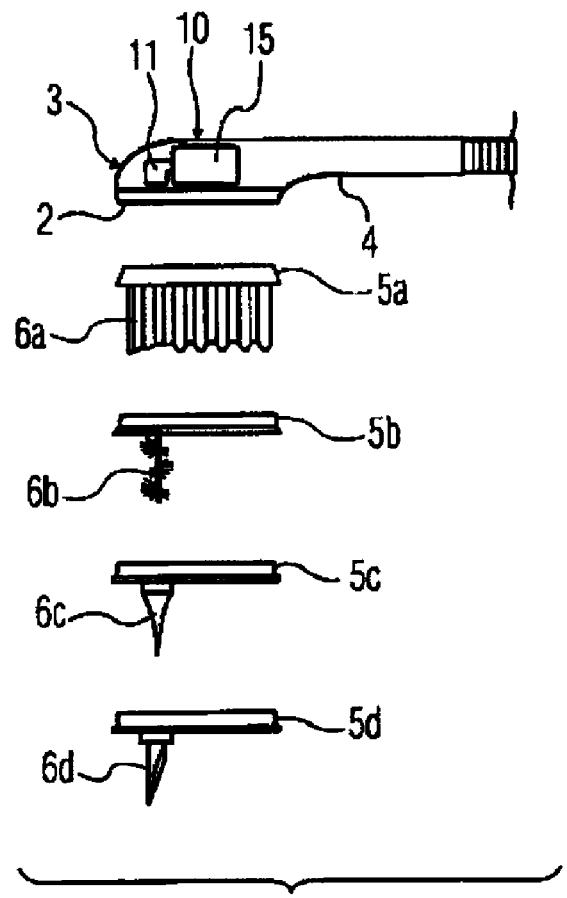
FIG. 5 shows a front part of the toothbrush according to FIG. 4 with different embodiments of exchangeable treatment heads.

As can be seen from FIG. 5, it is possible, instead of the bristle carrier 5 or 5a, which forms part of a conventional brush head and is provided with respective clusters of bristles 6 or 6a, to position other, optionally different bristle carriers or adapters 5b to 5d on the retaining part 2, these being provided with different interdental brushes 6b, 6c or interdental treatment parts 6d for effective cleaning of the spaces between the teeth. The interdental brush 6b may be designed, for example, as a helical brush made of coated wire with plastic filaments twisted in. The interdental brush 6c comprises bristles which, together, form a cluster tip. The treatment part 6d may be designed, for example, as a plastic element which has a tip and may preferably be provided with an abrasive coating for removing plaque and tartar from the spaces between the teeth. Of course, it would also be possible to use any other desired treatment heads. It is also the case with the variant according to FIGS. 4 and 5 that the bristle carrier 5 could be configured such that a vibration-induced movement in relation to the retaining part 2 were possible.

For the introduction of the vibratory device 10, the connecting lines 33, 34 and further electronic components, it is possible for a toothbrush according to the invention, or the housing thereof, to be produced in two parts and for the two parts to be welded in a water-tight manner once the abovementioned parts have been positioned therein. It is also possible, however, for a toothbrush according to the invention to be produced by injection molding preferably involving two or more components. The abovementioned parts are advantageously positioned as a unit in an injection molding made of a first material component and then encapsulated in the second material component (or in the further material component) by injection molding. It is not necessary here for full encapsulation to take place. Certain parts may be exposed, as a result of which it is possible to achieve an esthetic effect.

It would also be possible, however, for the abovementioned electronic components to be inserted into a ready-molded handle 1. In a preferred embodiment, since it is not only the vibratory element 11, 11' itself but also the drive, i.e. the micromotor 15, which are arranged in the front head part 3, or in the directly adjacent front region of the neck part 4, it is not necessary for a mechanical drive element to be led through the flexible neck part 4 in order to connect the micromotor to the vibratory element 11. In this embodiment, electric lines 33, 34 (e.g., wires, cables or electrically conductive plastic tracks) run through the neck part 4.

According to one embodiment of the invention, use is made of a mechanical vibratory device 10 which has a diameter of less than about 15 mm preferably less than about 6 mm, and is less than about 35 mm, preferably less than about 20 mm, in length. This ensures that the toothbrush may be of ergonomic configuration and is easy to handle. A toothbrush according to the invention corresponds, in size, more or less to the conventional manual toothbrushes, which makes them more straightforward to handle in comparison with the commercially available, considerably larger electric toothbrushes. A number of head configurations can produce an enhanced cleaning effect when the mechanical vibratory device is engaged.

FIGS. 6-9 illustrate a toothbrush 610 in accordance with one embodiment of this invention. As shown therein toothbrush 610 includes an elongated hand-held handle 612 with a head 614 connected to and extending from the handle. The head 614 is divided into a plurality of separate cleaning areas which are spaced from each other. As illustrated the cleaning areas include a base 616 located at the distal end of the head 614 and projecting outwardly from the main body portion 930 of the head. Base 616 includes at least one and preferably a plurality of cleaning/treating elements 618. Head 614 further includes a base or supporting member 620 at the proximal end of head 614 cleaning/treating elements 618 also extend outwardly from base 620.

Mounted between the cleaning areas which incorporate bases 616 and 620 are a pair of pods 622, 624. Each pod is provided with at least one and preferably a plurality of cleaning/treating elements. As later described the pods 622, 624 have a greater degree of movability than do the bases 616, 620. In a preferred practice of the invention the pods 622, 624 are resilient members extending from an elastic material 636 so that the pod cleaning/treating elements add a motion range beyond the cleaning/treating elements 618 which are generally static or non-movable. The pods 622, 624 comprise a thin pad or plate 934 which provides a support area onto which the cleaning/treating elements are affixed. Because the various cleaning/treating elements are separated from each other such as by channels 728, which extend completely across head 614 in a transverse direction, and because of the elastic nature of pods 622, 624, the cleaning/treating elements 626 may be capable of 360 degrees rotation about the vertical axis of each individual pod. The angle of the bend may be dictated by the ability of the material to bend.

Toothbrush 610 thus provides a head 614 wherein the front (distal end) and the back (proximal end) areas are in a relatively fixed position and wherein the cleaning/treating elements, such as bristle strands, 618 do not have any extra degree of motion. The middle portion of head 614, however, has two areas of cleaning/treating elements 626, which are capable of 360 degree rotation.

Figure 9:
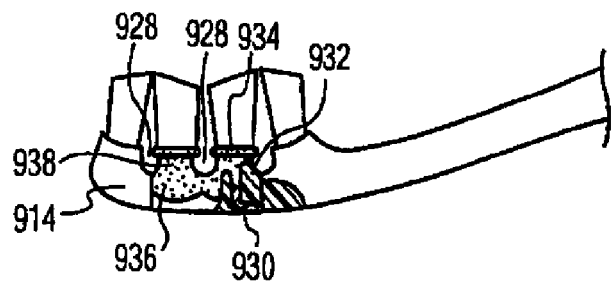
FIG. 9 is a side elevational view similar to FIG. 7 partially broken away.

As best shown in FIG. 9 the head 914 includes a main body portion 930 which supports the bases and pods. Body portion 930 and bases 616 and 620 are preferably made from conventional hard plastic materials, such as polypropylene, commonly used in the making of toothbrush handles and heads. Pods 622, 624, however, are made so as to be resilient. In a preferred practice of this invention, the resiliency of pods 622, 624 is achieved by providing a thin diameter beam 932 which extends from the main body portion 930 of the head of the toothbrush. Beam 932 is joined into the bottom of a thin pad or plate 934 which provides a support area onto which the cleaning/treating elements 626 are affixed. The manner of mounting the cleaning/treating elements 626 to the support pads 934 can be achieved utilizing various cleaning/treating elements, such as bristles and other cleaning materials, in known attachment methods.

The desired flexibility or resiliency of the pods 622, 624 is enhanced by enclosing the thin beams 932 in elastic material 936 which could be acquired during the multi-injection molding process. The elastic material 936 serves as a rubber band by returning the beams 932 to their original form or initial position. This return action creates an active motion in the opposite direction of the beam bend which aids in the cleaning of teeth by introducing extra brushing strokes.

Figure 6:
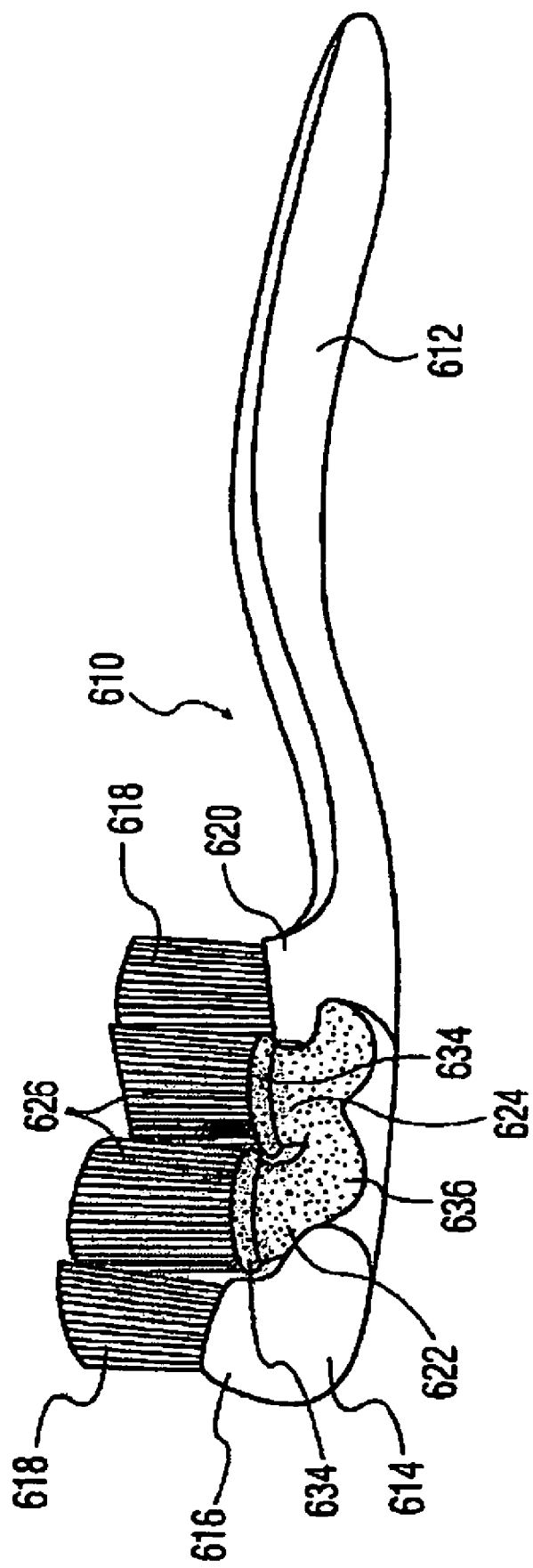
FIG. 6 is a perspective view of an additional toothbrush embodiment in accordance with this invention.
Figure 7:
FIG. 7 is a side elevational view, in partial section, of the toothbrush shown in FIG. 6.

As best shown in FIGS. 6, 7 and 9 the pods 622, 624 include a widened portion disposed toward the body 930. The support pads 934 are also widened. Each pod has a narrow or reduced diameter central portion 938 longitudinally intermediate the length of each pod. Thus, each pod is of generally mushroom shape.

Beam 932 could be of any suitable shape such as having a cross-section which is circular, square or any other geometric shape that provides a thin dimension or thin diameter to the beam to facilitate the bendability of the beam. The elastomer 936 may be considered as a continuous layer of any suitable thickness which covers the entire central area of head 614 as illustrated so that both pods 622, 624 are incorporated as part of the same elastic material. The portion of the head 614 which includes pods 622, 624 may be formed as a separate subassembly similar to the subassembly later described with respect to FIGS. 10 and 11.

Although the invention could be practiced with a single base and a single pod and could be practiced with the base having some, but a lesser degree of flexibility than the pod, the invention is preferably practiced wherein the base is generally static or non-movable. In addition, the invention is preferably practiced where there are a plurality of such bases and a plurality of pods. The drawings illustrate a configuration of the invention where there are a total of four separate cleaning areas with the pods being located in the central portion of head 614. The invention may be practiced in a configuration in which the cleaning/treating elements comprise a plurality of bristles or strands on each base and each pod.

Figure 8:
FIG. 8 is a top, plan view of the toothbrush shown in FIGS. 6 and 7.

As illustrated in FIG. 8 each base 616 and 620 and each pod 622 and 624 may have a generally oval outer surface. The bases and pods are longitudinally aligned, but spaced from each other by the depressions or open areas which form the channels 728. As also illustrated in FIG. 8 the pods may have a larger outer surface or cleaning/treating element carrying surface than do the bases.

As shown in FIG. 7 the terminal surfaces of the cleaning/treating elements 618 and 626 are tapered so that the terminal surfaces of the cleaning/treating elements 618 taper outwardly in a direction toward the center of head 614 while the terminal surfaces of cleaning/treating elements 626 taper outwardly in a direction away from the center of head 614. Thus, the highest points of each set of cleaning/treating elements 618 and its adjacent set of cleaning/treating elements 626 are generally disposed toward each other for each pair of base and pod 616, 622 and 620, 624.

Any suitable form of cleaning/treating elements may be used as the cleaning/treating elements 618 and 626 in the broad practice of this invention. The term "cleaning/treating elements" is intended to be used in a generic sense which could include conventional fiber bristles or massage elements or other forms of cleaning/treating elements such as elastomeric fingers or walls arranged in a circular cross-sectional shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

Using different cleaning materials as cleaning/treating elements of the toothbrushes may yield different effects. In an attempt to provide better stain removal a rubber-like material or elastomer can be used in combination with conventional bristles or used by itself to "brighten/whiten" the teeth.

It is to be understood that the specific illustration of the cleaning/treating elements is merely for exemplary purposes. The invention can be practiced with various combinations of the same or different cleaning/treating element configurations (such as stapled or in-molded technology bristles, etc.) and/or with the same bristle or cleaning/treating elements materials (such as nylon bristles, spiral bristles, rubber bristles, etc.) Similarly, while FIG. 7 illustrates the cleaning/treating elements to be generally perpendicular to the outer surface of head 614, some or all of the cleaning/treating elements may be angled at various angles with respect to the outer surface of head 614. It is thereby possible to select the combination of cleaning/treating element configurations, materials and orientations to achieve specific intended results to deliver additional oral health benefits, like enhanced cleaning tooth polishing, tooth whitening and/or massaging of the gums. Further, although shown as a manual toothbrush, the disclosed head and cleaning elements could be formed as part of a powered brush, e.g., as part of a vibrating brush (as in FIG. 1) with the drive means disclosed for the brush of FIG. 16, or other known powered brushes where the heads or parts of the heads (e.g., platforms) are driven.

Figure 10:
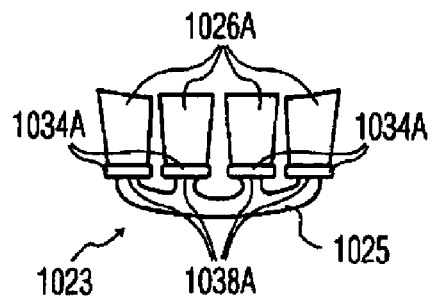
FIG. 10 is a side elevational view showing a subassembly of the bristle containing portion of the brush head in accordance with another aspect of this invention.
Figure 11:
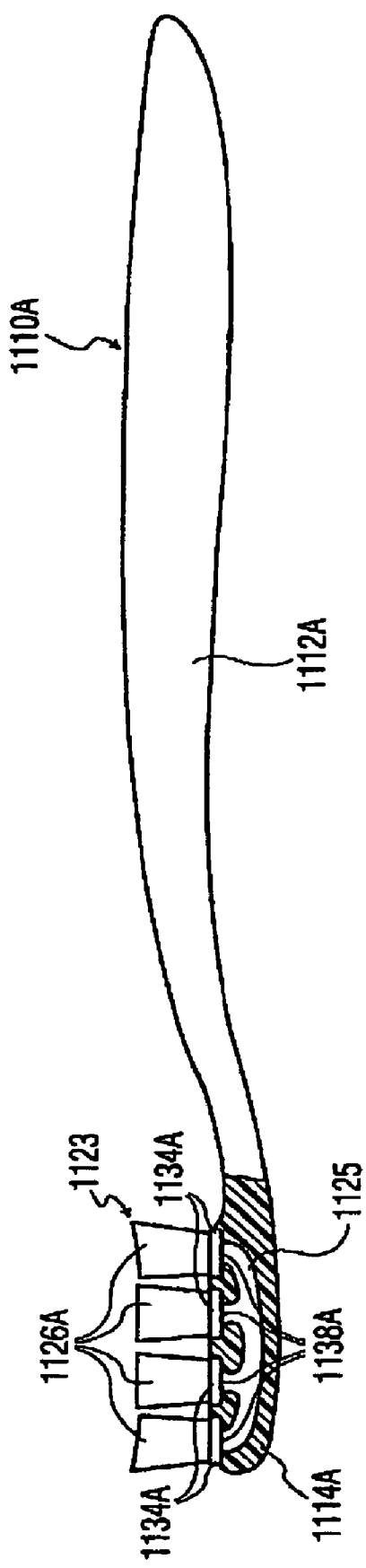
FIG. 11 is a side elevational view, in partial section, showing the subassembly of FIG. 10 incorporated in a completed toothbrush.

FIGS. 10-11 illustrate a further embodiment of this invention. The toothbrush 1110A has the ability to provide flexible support for the bristles 1026A, 1126A in designated areas. The flexibility is provided by designing the tuft holding areas 1034A, 1134A as plates which in combination with the stems 1038A, 1138A forms pods of mushroom shape. The mushroom stem 1038A, 1138A is made flexible to allow the plate 1034A, 1134A populated with bristles or cleaning/treating elements 1026A, 1126A to move in different directions while brushing, as described with respect to the flexible pods of FIGS. 6-9.

FIGS. 10-11 show the toothbrush 1110A and in particular the cleaning/treating element or bristle carrying portion 1023, 1133 of the head 1114A. As shown in FIG. 10 the bristle or cleaning/treating element carrying portion 1023 forms an initial subassembly. This subassembly is made by introducing the cleaning/treating elements 1026A into the mold cavity into which a plastic material is injected. As the material injected cools off it permanently traps the bristles or cleaning/treating elements 1026A to form a brush or subassembly 1023.

To achieve a functional flexibility and proper tuft retention the portion of the bristle holding part or subassembly 1023 which comprises the plates 1034A, stems 1038A and interconnecting support 1025, 1125 is preferably a blend of polypropylene (PP) and soft TPE. Once the PP/TPE blend is combined with the bristles 1026A the subassembly 1023 is formed. The subassembly 1023 is then overmolded with an entire toothbrush handle 1012A and head 1014A during a second injection cycle to form the completed toothbrush 1110A shown in FIG. 11. If desired or required the entire handle 1112A and head 1114A absent the subassembly 1123 could be made first and the subassembly or bristle retaining portion 1123 made second.

It is to be understood that the invention described in FIGS. 10-11 could be practiced where all portions of the head 1114 include the flexible mushroom sections without having less flexible base portions such as bases 616 and 620 of FIGS. 6-9. Similarly, the subassembly two shot techniques of FIGS. 10-11 could be utilized in the embodiment of FIGS. 6-9 for forming the two or more central pods as a single subassembly initially made separate from the remainder of the toothbrush head 1114. The final toothbrush would be made in a second injection molding process wherein the subassembly having interconnected pods 622, 624 would be molded to the handle 612 and head 614 made of more rigid material.

As noted, FIG. 7 illustrates the terminal surfaces of the cleaning/treating elements 618 and 626 to be tapered in an up and down or zigzag manner. FIGS. 10-11 show an alternative taper wherein the terminal surfaces form a smooth, gentle, concave shape. If desired, other shapes may be used such as a planar shape for the terminal surfaces or a convex shape as well as the zigzag or up and down shape shown in FIG. 7. Similarly, the terminal ends of the cleaning/treating elements in the FIGS. 6-9 embodiment, as well as those of FIGS. 10-11, could have the various shapes such as zigzag, convex, concave or planar.

Figure 12:
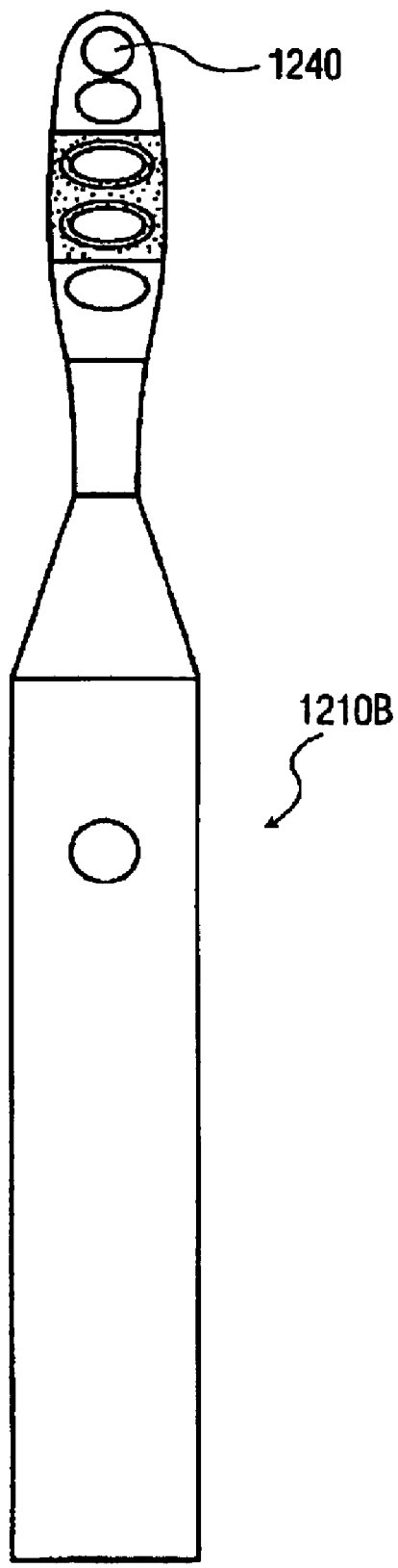
FIG. 12 is a top plan view of a further toothbrush in accordance with the invention.

FIG. 12 illustrates a toothbrush 1210B, which includes a power driven movable disc or section 1240 having cleaning elements. Although FIG. 12 shows movable section 1240 to be at the distal end of the head, the movable section(s) could be located at any desired location on the head.

Figure 13:
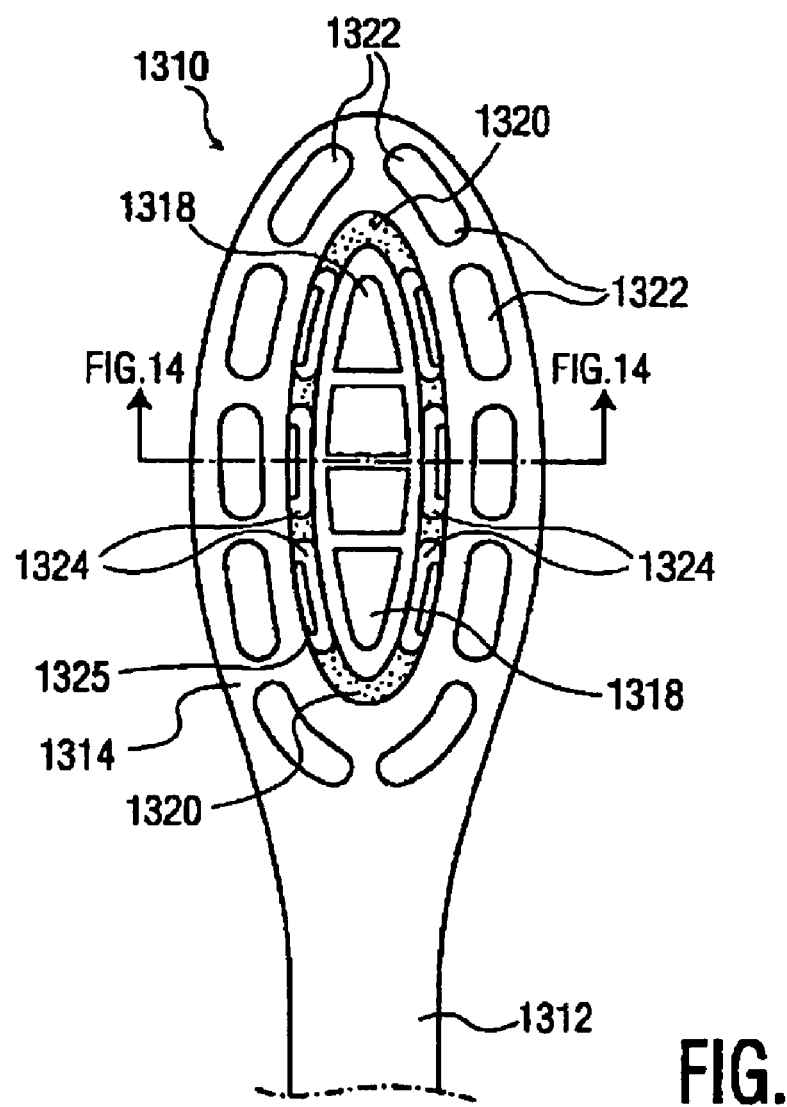
FIG. 13 is a top plan view of a head of a manual toothbrush in accordance with the invention.
Figure 14:
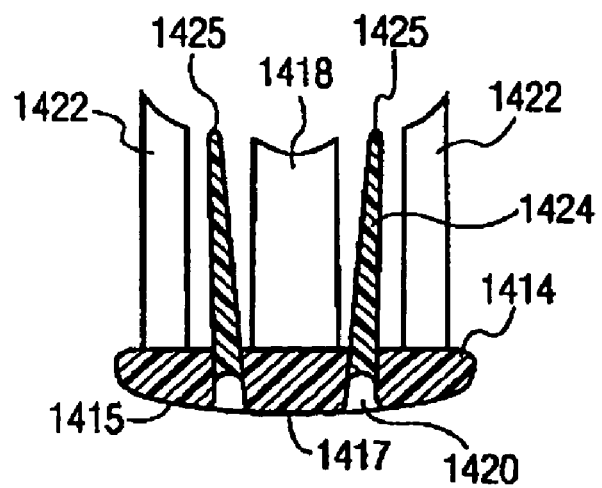
FIG. 14 is a side cross-sectional view taken along lines 14-14 of FIG. 13 showing the bristle and wiper arrangement with minimal force applied to the toothbrush handle.
Figure 15:
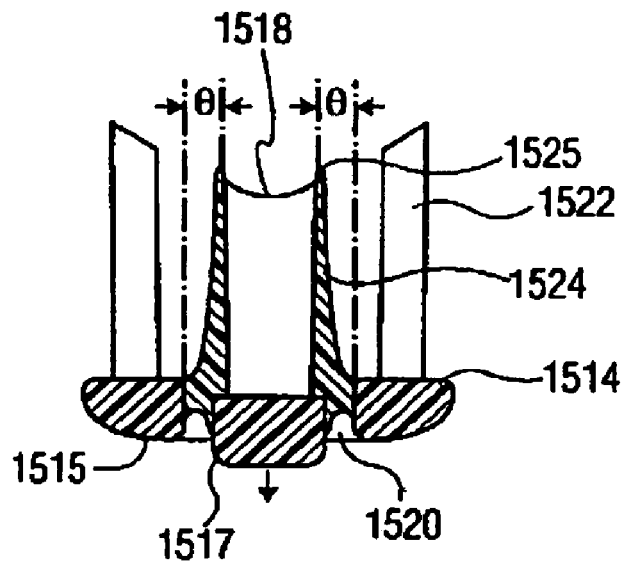
FIG. 15 is a side cross-sectional view taken along lines 14-14 of FIG. 13 showing the bristle and wiper arrangement where greater force is applied to the toothbrush handle.

FIG. 13-15 illustrate heads 1314, 1414, 1514 of a manual toothbrush 1310 in accordance with embodiments of this invention. Heads 1314, 1414, 1514 can be attached to handle 1312 (partially shown in FIG. 13). Heads 1414, 1524 have bottom surfaces 1415, 1515 respectively. In one embodiment, two groups of cleaning/treating elements or bristle are arranged on heads 1314, 1414, 1514. The first group is located in the central region 1417, 1517 of the head 1314, 1414, 1514 and comprises cleaning/treating elements 1318, 1418, 1518 in the form of strands or bristles. Elastomeric material 1320, 1420, 1520 is preferably of a material or combinations of material that can flex to become altered from its original shape and recover to its original shape randomly during brushing.

The first group of cleaning/treating elements 1318, 1418, 1518 flexibly mounted in head 1314, 1414, 1514 and 1614 (FIG. 16) are complemented by a second group of fixed cleaning/treating elements 1322, 1422, 1522 generally arrayed in a surrounding relationship with the first group 1318, 1418, 1518.

The first and second group of cleaning/treating elements work together to provide improved cleansing of teeth. To further promote teeth cleaning, the toothbrush 1310 of this invention may include, for example, wipers 1324, 1424, 1524 positioned between the two groups of cleaning/treating elements. These wipers are preferably made of rubber or like material and terminate in ends 1325, 1425, 1525. Further, any suitable form of cleaning/treating elements may be used as the cleaning/treating elements 1318 and 1322 in the broad practice of this invention.

It is to be understood that the specific illustration of the cleaning/treating elements is merely for exemplary purposes. The invention can be practiced with various combinations of the same or different cleaning/treating element configurations (such as stapled or in-molded technology bristles, etc.) and/or with the same bristle or cleaning/treating element materials (such as nylon bristles, spiral bristles, rubber bristles, etc.) Similarly, while FIG. 13 illustrates the cleaning/treating elements to be generally perpendicular to head 1314 some or all of the, cleaning/treating elements may be angled at various angles with respect to the outer surface of head 1314. It is thereby possible to select the combination of cleaning element configurations, materials and orientations to achieve specific intended results to deliver additional oral health benefits, like enhanced cleaning, tooth polishing, tooth whitening and/or massaging of the gums.

This invention may also be practiced where head 1314 includes one or more power or electrically operated movable sections carrying cleaning/treating elements.

Figure 16:
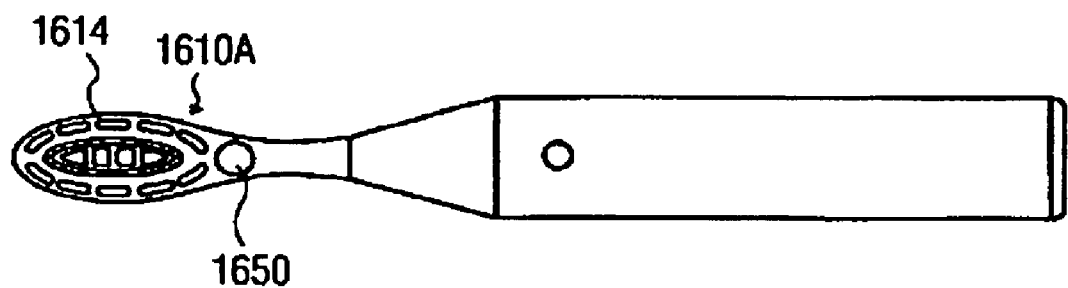
FIG. 16 is a top plan view of a powered toothbrush in accordance with the invention.

FIG. 16 illustrates a toothbrush 1610 A which includes a power driven movable disc or section 1650 having cleaning/treating elements. The movable section 1650 could be oscillated rotationally such as by using the type of drive mechanism shown in U.S. Pat. No. 5,625,916, or could move in and out using the type of drive mechanism shown in U.S. Pat. No. Re 35,941; all of the details of both patents are incorporated herein by reference thereto. Alternatively, the other types of drives referred to above could move section 50 in other manners and directions. Although FIG. 16 shows movable section 1650 to be at one end of the head, the movable section(s) could be located at any desired location on the head.

Figure 17:
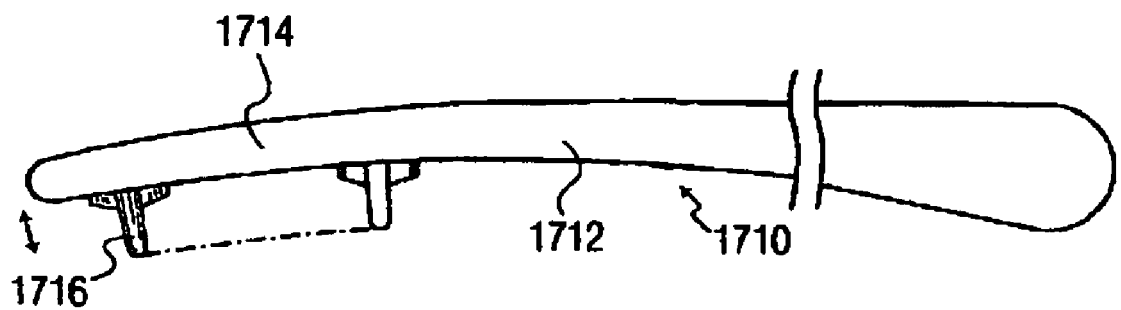
FIG. 17 is a side elevational overview of another toothbrush embodiment in accordance with the invention having a flexible head with fingers mounted thereon, shown broken along its length and showing the ribs interconnecting the finger and flexible head.
Figure 18:
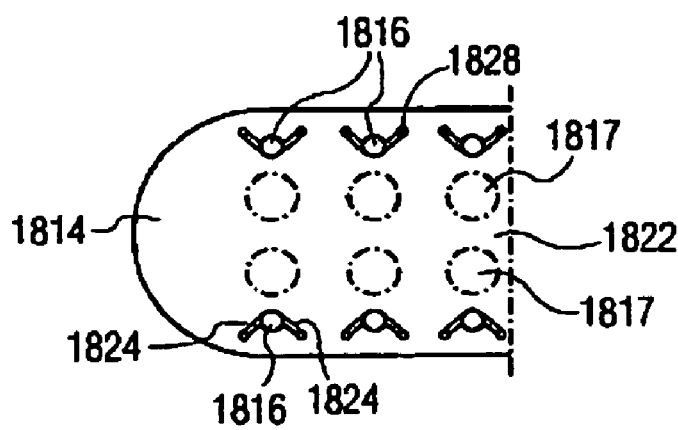
FIG. 18 is a fragmental front plan view of the toothbrush of FIG. 17 showing an arrangement of fingers connected by ribs to a flexible head.

FIGS. 17 and 18 illustrate a toothbrush 1710 with a handle 1712 and head 1714, 1814. Mounted on or in head 1714, 1814 are fingers 1716, 1816, preferably having a tapered shape. As shown in FIG. 18 fingers 1816 are preferably arranged about the periphery of head 1814. That location materially assists the gum massaging effect of the finger movement contemplated by this invention. More particularly, when the longitudinal axis of toothbrush 1710 is perpendicular to the axis of teeth being brushed, as is typical with most users, the fingers 1716, 1816 are closest to the gum line.

Figure 26:
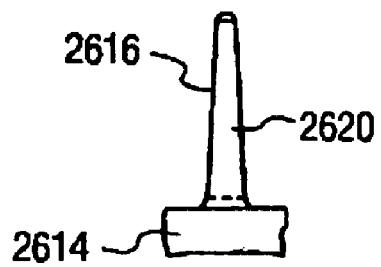
FIGS. 26-28 are fragmental elevational views of the fingers used with the toothbrush of FIG. 17.
Figure 27:
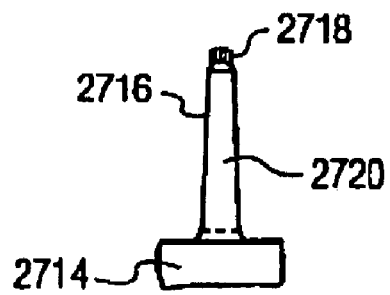
Figure 28:
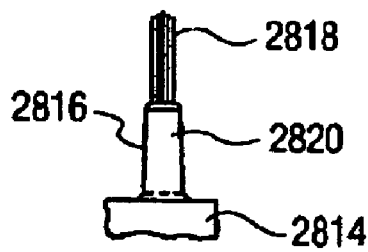

The fingers 1716, 1816 are preferably flexible and soft to the touch. Accordingly they may be formed of a soft elastomeric material. The general shape of fingers 2616, 2716, 2816 is illustrated in FIGS. 26-28 attached to heads 2614, 2714, 2814. As so illustrated they are tapered and comprise all elastomeric material (FIG. 26) or a set of bristles 2718 2818 partially surrounded by elastomeric material 2620, 2720, 2820 (FIGS. 27 and 28). The elastomeric material preferably extend along the length of finger 2616, 2716, 2816 a sufficient distance to facilitate attachment of ribs as described in more detail below.

To facilitate the therapeutic movement of the fingers, the head of the toothbrush may be flexible and the fingers may be flexibly mounted in the head. FIG. 25 illustrates one form of flexible mounting of fingers in head 2514. In this embodiment the head 2514 has a box-like shape in cross section. At least the upper face 2522 of head 2514, and preferably the entirety of head 2514, is made of a flexible material so that the axes of fingers 2516 can move relative to the plane of toothbrush 1710. The fingers 2516 project from apertures 2526 in the flexible upper face 2522 of head 2514. The fingers 2516 are connected to ribs 2524. Any rib and finger 2216, 2316, 2416 arrangement shown in FIGS. 22-24 can be molded into the toothbrush head 2214. This flexible mounting in a flexible portion 2222 of head 2214 assists in obtaining the desired lateral movement of fingers relative to the axes of toothbrush 1710. The role of ribs in obtaining that movement is explained below.

Figure 29:
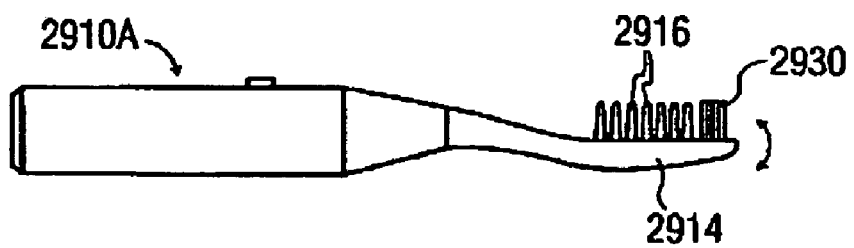
FIG. 29 is a side elevational view of a further toothbrush configuration using a flexible head and gum stimulation fingers.

FIG. 29 illustrates a powered toothbrush 2910A containing the fingers 2916 of the invention mounted on a flexible head 2914 of the toothbrush. Cleaning elements 1817 may be mounted inboard of fingers 1816 as illustrated in FIG. 18.

Although FIG. 29 shows movable section 2930 to be at the distal end of the head, the movable section(s) could be located at any desired location on the head.

Figure 30:
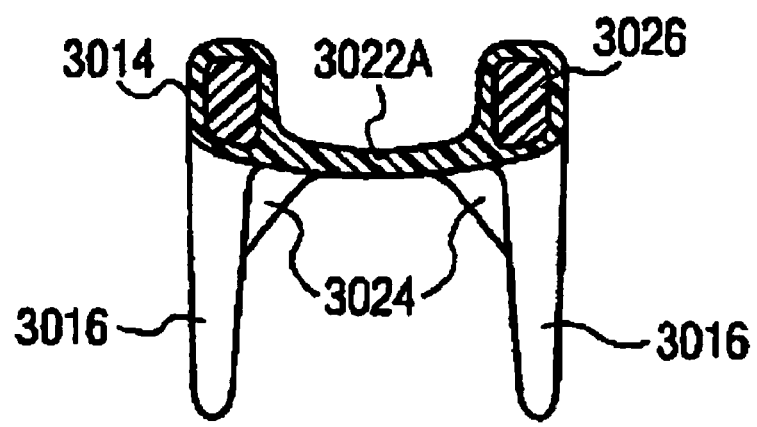
FIGS. 30 and 31 are cross sectional views of the fingers with ribs interconnecting the fingers to a flexible portion of the toothbrush head.
Figure 31:
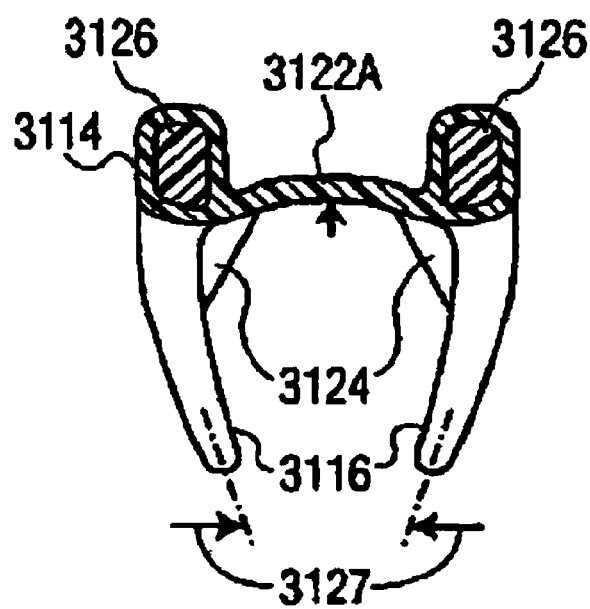

Another manner of imparting movement to the fingers 3016, 3116 is illustrated in FIGS. 30 and 31. As illustrated, fingers 3016, 3116 are physically linked to a flexible face 3022A, 3122A of head 3014, 3114 by angled rib 3024, 3124. Rib 3024, 3124 can be integrally molded into head 3014, 3114 and finger 3016, 3116 during the manufacture of toothbrush 1710. It can also be formed of a more rigid (than elastomeric) material such as polypropylene in order to enhance lateral movement of fingers 3016, 3116. Flexible face 3022A, 3122A of head 3014, 3114 in this embodiment can be molded around frame members 3026, 3126 forming the outer periphery of head 3014, 3114. These frame members 3026, 3126 of head 3014, 3114 may be attached to handle 1712 of toothbrush 1710 in a known manner.

The role of ribs and the flexible head in imparting lateral movement to the fingers is illustrated in FIGS. 18-21. FIG. 18 illustrates the location of fingers 1816 and ribs along outer edges of flexible face 1822 of head 1814. Other groups of bristles or cleaning/treating elements 1817 are arranged inboard of fingers 1816 as illustrated in FIG. 18. Fingers 1816 on the outer edge of head 1614 are closest to the gum line when the user holds the toothbrush in a normal position, i.e., with the longitudinal axis perpendicular to the axis of the user's teeth. Ribs 1824 extend from the side of finger 1816 to the face 1822 or 1822A of flexible head 1814. These ribs can have a triangular, trapezoidal or like shape that interconnects the finger 1816 to the face of flexible head 1814. This interconnection assures lateral movement of finger 1816 as the face 1822 or 1822A deflects outward or inward along the longitudinal axis when in use as described below.

Figure 19:
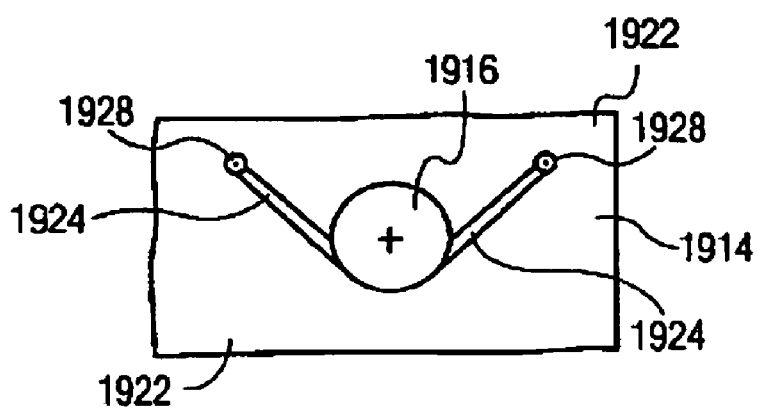
FIG. 19 is a fragmental plan view of single finger connected by ribs to an unflexed toothbrush head of the toothbrush of FIG. 17.
Figure 20:
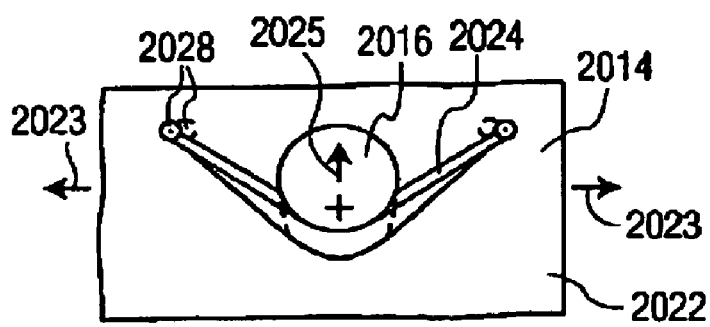
FIGS. 20 and 21 are fragmental plan views of a single finger connected by ribs to a flexible head in flexed positions caused by movement of the flexible head of the toothbrush of FIG. 17.
Figure 21:
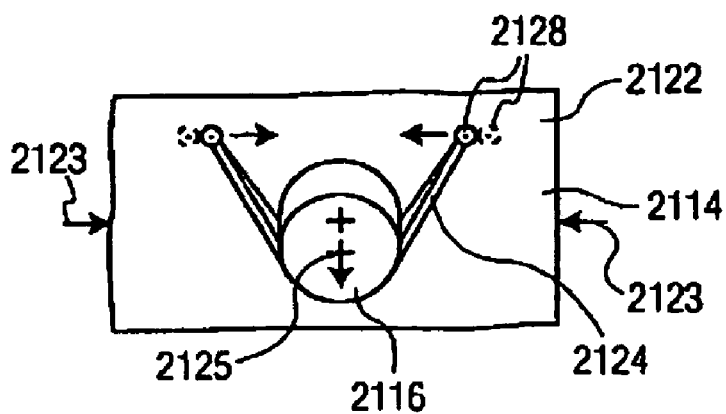

The lateral movement of finger 1816, 1916, 2016, 2116 is illustrated in the sequence shown in FIGS. 19-21. The fingers 1816, 1916, 2016, 2116 have ribs 1824, 1924, 2024, 2124 that terminate in ends 1828, 1928, 2028, 2128. In FIG. 19 there is no deflection of face 1922 or 1924 of flexible head 1914. FIG. 20 represents a deflection of face 2022 that stretches that face as shown by the arrows 2023 at the edge of this fragmental view. When so stretched the ends 2028 of rib 2024 anchored to face 2022 move away from each other. That movement exerts a lateral force on finger 2016 causing it to move laterally toward the outside periphery of head 2014 as indicated by the arrow 2025 in FIG. 20. Conversely, when deflection of face 2122 or 2122A of head 2114 causes that face to compress, the ribs 2124 push finger 2116 laterally in the opposite direction as indicated by the arrow 2125 in FIG. 21 as indicated by the arrow 2125 in FIG. 21. Thus, as various forces are transmitted to flexible face 2122 or 2122A of head 2114 during use, that head moves in compression or expansion. That movement causes fingers 2116 to move in a lateral direction thereby promoting tooth cleaning and gum stimulation.

Another embodiment of the invention illustrated in FIGS. 30 and 31 shows ribs 3024, 3124 oriented approximately 90 degrees to the longitudinal axis of toothbrush 1710 versus approximately 45 degrees shown in FIGS. 18-21. In the former embodiment, movement of the flexible face 3022A in an upward direction (FIG. 30) causes lateral inward movement of fingers 3016 as illustrated by the arrows 3127 in this Figure. Conversely, downward movement of flexible face 3022A would cause lateral movement of fingers 3016 away from each other toward the outside of head 3014 (not illustrated).

Figure 22:
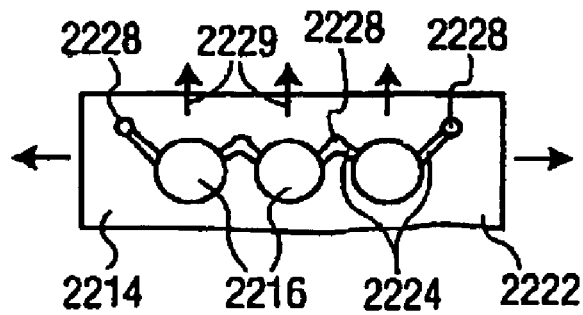
FIGS. 22-24 are fragmental plan views of multiple fingers interconnected to each other and to a flexible toothbrush head in accordance with FIG. 17 by ribs forming a web between the fingers.
Figure 23:
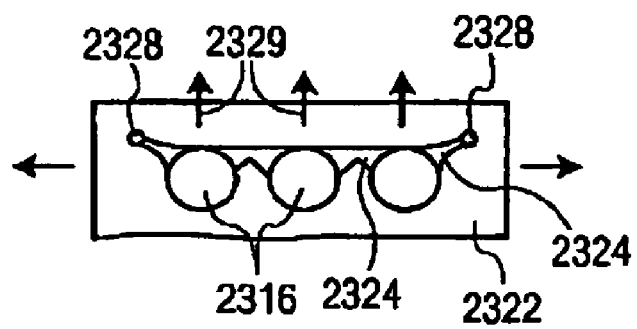
Figure 24:
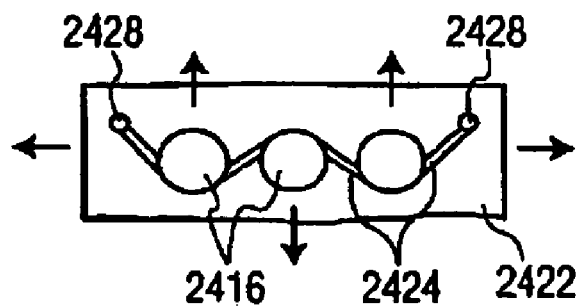
Figure 25:
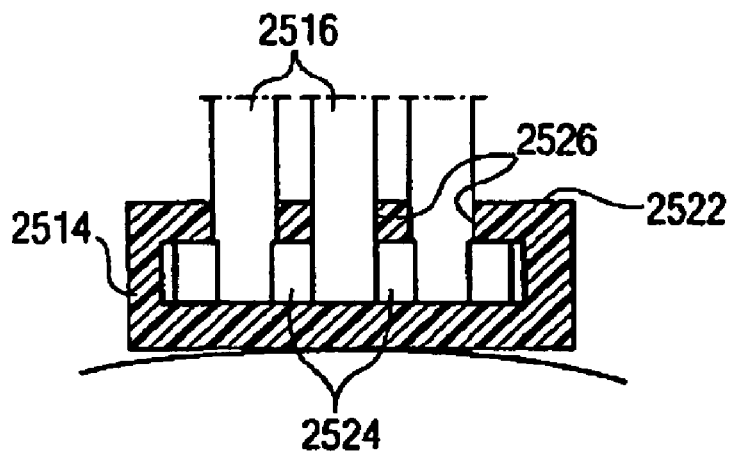
FIG. 25 is a fragmental cross-sectional view in elevation of the fingers mounted in a flexible toothbrush head in accordance with FIG. 17.

Other arrangements of ribs 2224, 2324, 2424 and their attachment to fingers 2216, 2316, 2416 are illustrated in FIGS. 22-24. The ribs 2224, 2324, 2424 terminate in ends 2228, 2328, 2428. The arrangements are located on flexible faces 2222, 2322, 2422. As illustrated, multiple fingers 2216, 2316, 2416 are interconnected by a continuous rib 2224, 2324, 2424. FIG. 22 illustrates the interconnecting ribs 2224 on one side of fingers 2216. Thus, upon deflection of flexible face 2222 of head 2214 all fingers 2216 move in the same direction as indicated by the arrows 2229, 2329 in FIGS. 22 and 23. If it were desirable to have the fingers 2416 move in different directions the arrangement of ribs 2424 shown in FIG. 24 can be utilized.

It is to be understood that the specific illustration of the cleaning/treating element is merely for exemplary purposes. The invention can be practiced with various combinations of the same or different cleaning/treating element configurations (such as stapled or in-molded technology bristles, etc.) and/or with the same bristle or cleaning/treating element materials (such as nylon bristles, spiral bristles, rubber bristles, etc.). Similarly, while FIG. 18 illustrates the cleaning/treating elements to be generally perpendicular to head 1814, some or all of the cleaning/treating elements may be angled at various angles with respect to the outer surface of head 1814. It is thereby possible to select the combination of cleaning/treating element configurations, materials and orientations to achieve specific intended results to deliver additional oral health benefits, like enhanced cleaning, tooth polishing, tooth whitening and/or massaging of the gums. This technology may also be used in manually powered toothbrushes.

Figure 32:
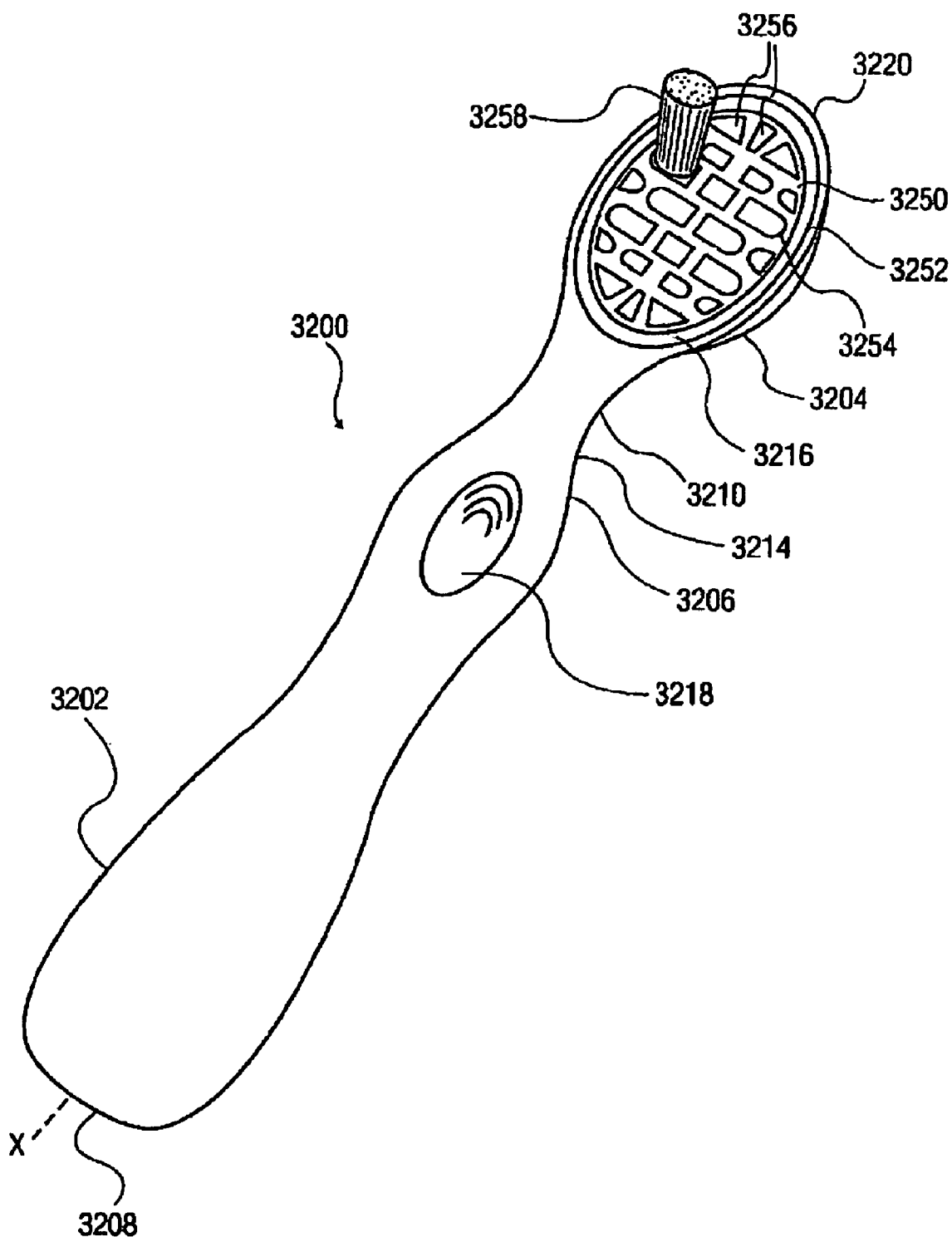
FIG. 32 is a perspective view of the toothbrush of FIG. 29 including a head constructed in accordance with another embodiment of the invention.
Figure 33:
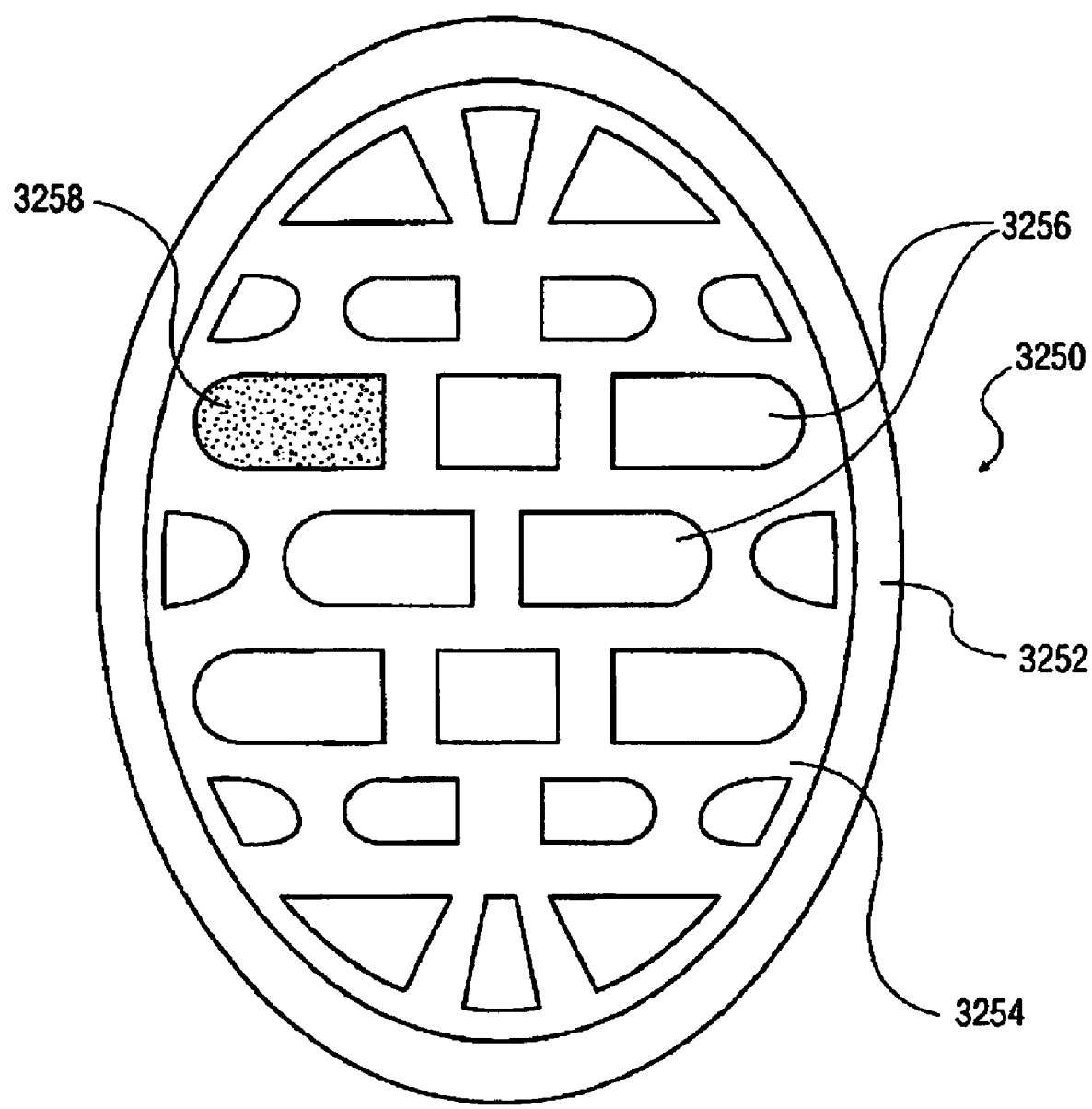
FIG. 33 is a top plan view of the head of FIG. 32.

Referring to FIGS. 32 and 33, an exemplary toothbrush including a head plate according to the invention is illustrated and generally indicated at 3200. Toothbrush 3200 includes a handle 3202 at a proximal end thereof, and a brush section 3204 that is defined by a neck 3210 that terminates in a head 3220 at a distal end of toothbrush 3200. Handle 3202 has a free proximal end 3208 and an opposite neck end 3206. Neck 3210 generally includes a first end 3214 and a second end 3216 with first end 3214 being located at neck end 3206 of handle 3202 and the second end 3216 being located at head 3220. In other words, neck 3210 is the portion of toothbrush 3200 that extends between handle 3202 and head 3220. Head 3220 is preferably generally aligned with the longitudinal axis x-x of toothbrush 3200.

Neck 3210 and handle 3202 may be constructed as a unitary member by forming neck 3210 integral to handle 3202 at neck end 3206 of handle 3202, or may be formed detachable from handle 3202 at the neck end 3206. In accordance with this detachable embodiment, the combined neck 3210 and head 3220 can be removed from handle 3202 to permit cleaning, servicing and/or interchanging of either handle 3202 or the combined neck 3210 and head 3220 (brush section 3204). When neck 3210 is formed to be detachable from handle 3202, first neck end 3214 preferably includes a connector linkage (not shown) detachably joined to handle 3202 using traditional techniques. It will also be appreciated that the point of detachment may be between head 3220 and neck 3210 such that head 3220 is of a refill head type.

It will further be appreciated that the illustrated shapes of handle 3202 and neck 3210 are merely exemplary in nature and handle 3202 and/or neck 3210 can be formed to have any number of shapes. Preferably, the shapes of handle 3202 and neck 3210 are ergonomically pleasing to a user of toothbrush 3200 and provide a toothbrush that is easily gripped and held and easily manipulated by a user. For example, handle 3202 may include a slightly recessed finger section 3218 which is formed on handle 3202. The recessed finger section 3218 is designed to receive the thumb of one hand to thereby assist a user in proper placement of toothbrush 3200 in a user's hand. Recessed finger section 3218 may include ribs or another type of roughened surface to assist a user in gripping toothbrush 3200 at recessed finger sections 3218. Of course other patterns for providing recessed finger sections may be employed.

The head plate for the bristles is formed with a solid perimeter and defines a field of variously shaped and sized holes within this perimeter. Fibers that are to form the tufts are then placed in the holes in the field of the head plate, and the backs of the tufts are melted together to fix their position relative to one another.

The tufted head plate is then inserted into a predefined receiving portion of the head portion of a toothbrush handle and is sonically welded into place. The brush is then end rounded and packaged for sale as a traditional toothbrush.

As is shown in FIGS. 32 and 33 of the present invention, a head plate 3250 is provided, and is fixed to head 3220 of toothbrush 3200, preferably by sonic welding, although any other appropriate attachment technique may be employed. Head plate 3250 is famed of at least two materials. A first rigid material is used to form the perimeter portion 3252 of the head plate. Such a material, such as for example polypropylene, is easily sonically welded. A tuft field 3254 is formed of a flexible elastomer (preferably having a hardness of 90 Shore A or less).

A process known as "Anchor Free Tufting" (AFT) is used in the formation of head 3250. In such an AFT process, head plate 3250 is used for holding toothbrush bristles in their proper orientation. When the bristles are placed in their proper orientation through the corresponding holes in the head plate 3250, the head plate 3250 is placed in the head plate cavity formed in the front face of the head section 3204 of the brush, and for insertion into a toothbrush.

As is best shown in FIG. 32, head plate 3250 is formed with a solid perimeter and defines a field of variously shaped and sized apertures or holes 3256 within the flexible elastomer tuft field 3254. Fibers that are to form one or more bristle tufts 3258 are then placed in the holes in field 3254 of head plate 3250, and the backs of tufts 3258 are melted together to fix their position relative to one another. Thus, such a head plate is able to flex, thereby allowing the tuft field and bristles to move under normal brushing conditions, while providing a perimeter of structural rigidity that is able to be sonically welded. Therefore, the head plate and bristles move or flex under the pressure of normal brushing. While bristles 3258 are shown, elastomeric members may also be used in place of these 31 tufts. Furthermore, while a particular tuft field pattern is shown, any desirable tuft field pattern may be employed. Furthermore, the bristle material need not be the same for all of the tufts, and indeed varying materials for performance color or indication of life remaining in the brush head, may be used exclusively, or in combination as desired.

Figure 34:
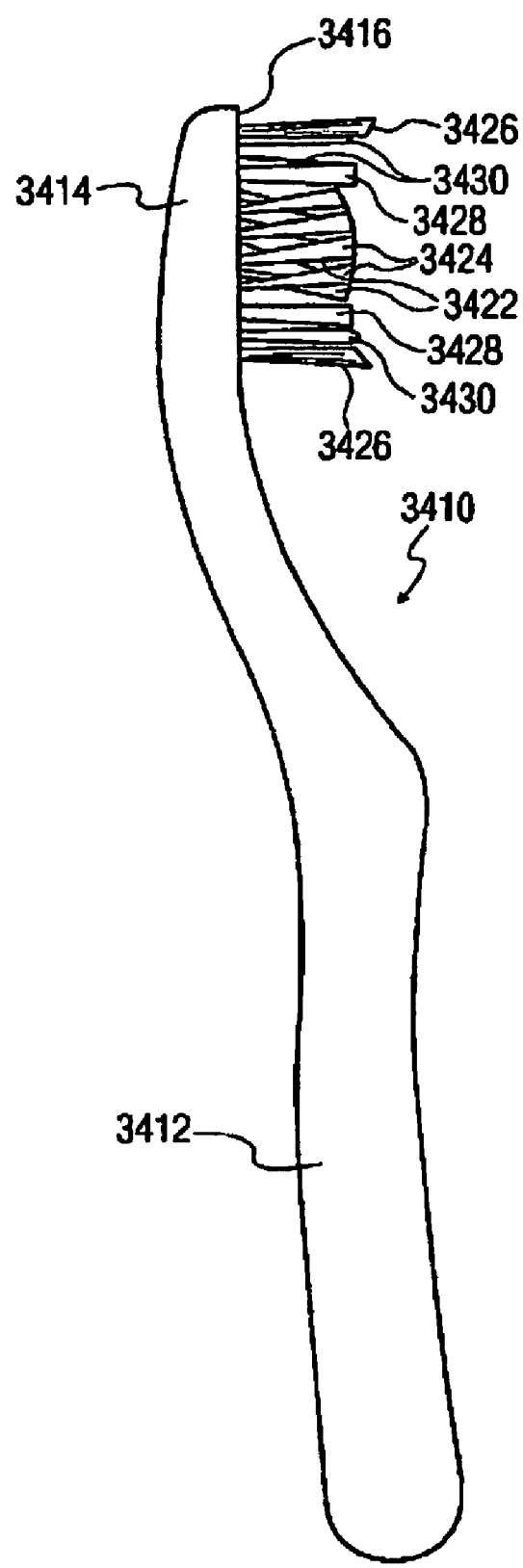
FIG. 34 is a side elevational view of a further toothbrush embodiment in accordance with this invention.

FIG. 34 illustrates a toothbrush 3410 which could be of generally typical structure in the sense of having a handle 3412 at one end connected to a cleaning head 3414 which has an outer surface 3416 from which a plurality of cleaning/treating elements extend.

In a preferred embodiment, toothbrush 3410 includes a mechanical vibratory device as described above (not shown in FIG. 34) which causes the cleaning head to vibrate. The mechanical vibratory device is preferably located in the head or in a region adjacent to the cleaning head and operatively connected to an electric power source.

In accordance with this invention the cleaning head 3414, as shown in FIG. 35, may include a peripheral frame 3518. A resilient membrane 3520 is secured across frame 3518 so that membrane 3520 is free to move in a direction toward and away from the outer surface 3416. The membrane 3520 could be recessed below outer surface 3416 or could be flush with the outer surface. Because membrane 3416 is mounted across frame 3418 when pressure is applied to membrane 3520 the membrane would move in a direction away from the outer surface 3416 and would return in the opposite direction upon release or diminution of pressure.

Head 3414 may be completely open in the area of frame 3518, except for membrane 3520, or may include a rear wall spanning the frame and spaced from membrane 3520 to permit inward movement of membrane 3520.

An embodiment of the present invention is preferably directed toward making use of the movement that results from resilient membrane 3520 in combination with various specialized types of cleaning/treating elements, particularly such elements wherein some of the elements have physical characteristics which differ from other of the elements so that an enhanced cleaning or treatment results from the combination of the actual cleaning/treating elements performing their specialized functions and the movement of the resilient or flexible membrane 3520. Membrane 3520 may be considered as defining a cleaning field in which the various cleaning/treating elements are located.

FIG. 34 illustrates some examples of cleaning/treating elements wherein the various elements are in the form of different types of bristles. The bristle pattern of FIG. 34 is disclosed in U.S. Pat. No. 6,643,886 to Moskovich et al. filed on Feb. 21, 2001, which is hereby expressly incorporated by reference. As illustrated, the cleaning/treating elements include angled bristles 3422, 3424 which may also be arranged to crisscross each other. Other bristles could include generally straight or inclined bristles having slanted or pointed ends, respectively, and other straight bristles 3428 having flat ends. The slanted end bristles 3426 have their outer surface taper from one side to another, while the pointed portion of the bristles 3430 is located at the center of the bristles. As shown in FIGS. 34 and 38 the various combinations of bristles could also result in multi-level bristles.

The bristles could be secured to membrane 3520 in any suitable manner such as by anchor-free tufting or by any other conventional techniques. Instead of having individual tufts of bristles the bristles could be located closely together to form an elongated bristle wall 3832 such as shown in FIG. 38. Such bristle wall 3832 could be included on the same cleaning field as various of the previously described tufts of bristles. The wall 3832 could be straight, curved, sinusoidal or of any desired shape.

The invention may be practiced where the cleaning/treating elements are elastomeric elements rather than tufts of bristles of FIGS. 34 and 38 made of nylon fiber or the like. It is also contemplated that the invention may be practiced where the cleaning/treating elements include a combination of bristle elements and non-bristle elements. The non-bristle elements include, for example, a tongue-cleaning structure, elastomeric fingers, elastomeric walls and prophy cups. As noted above, this kind of head could be used as a manual or powered toothbrush.

FIGS. 36-37 show some examples of the incorporation of elastomeric cleaning/treating elements. As shown in FIG. 36 a plurality of rubber or elastomeric fingers 3634 are mounted to membrane 3520. The fingers could be of any suitable size and shape such as being oval at their base and tapering uniformly inwardly toward their free end to generally end in a point or narrow line type structure at their free end. The size of the individual elastomeric fingers 3634 could vary as illustrated in FIG. 36. FIG. 37 shows other forms of elastomeric cleaning/treating elements. Such other forms include prophy cups 3736, elastomeric walls 3738 and elastomeric fingers 3740 which would be conically shaped to function as massage elements. The elastomeric walls could be straight, arcuate, sinusoidal or of any other desired shape. The size and number and location of these elastomeric elements could vary. FIG. 37 also shows the combination of elastomeric elements and bristles. As shown therein, various tufts of bristles 3742 are located in a ring-like pattern around a central portion of bristles 3744. It is to be understood that any combination of the bristles and/or elastomeric elements mounted to membrane 3520 could be used within the spirit of this invention. Similarly, as illustrated in FIG. 39, the frame 3518 of head 3414 could be of sufficient size so as to accommodate cleaning/treating elements such as spaced tufts of bristles 3946 secured directly to the rigid material such as conventionally used in the toothbrush head and handle. These fixed cleaning/treating elements 3946 would be in combination with the movable elements on the cleaning field formed by membrane 3520. As previously noted, any of the disclosed heads could be used in manual or powered toothbrushes.

The toothbrush and particularly the cleaning head 3414 could also be provided with various forms of structure to achieve tongue cleaning. Thus, FIG. 38 illustrates tongue cleaning structure 3848 at the backside of head 3414 while FIG. 39 illustrates the tongue cleaning structure 3950 at the tip of cleaning head 2414 remote from the handle. The tongue cleaning structure could be stiff or flexible fingers or walls, made from a suitable elastomeric material. The various cleaning/treating elements could also be located to provide for interproximal cleaning. Further, any of the tongue cleansers disclosed herein can be used on any of the heads, in conjunction with manual or powered toothbrushes, or used as a separate oral care implement.

In the preferred practice of the invention the resilient membrane 3520 has mounted to it a plurality of various types of cleaning/treating elements with different physical characteristics. Such physical characteristics could be of the types previously described with regard to size, shape and structure of the cleaning/treating elements or could be the result of different internal characteristics such as differing degrees of stiffness.

The present invention thus makes it possible to select the combination of cleaning/treating element configurations, materials and orientations to achieve specific intended results to deliver additional oral health benefits such as enhanced cleaning, tooth polishing, tooth whitening and/or the massaging of gums. These results are enhanced by mounting the various cleaning/treating elements on the resilient cleaning field so that in addition to the benefits from the specific physical characteristics of the individual cleaning/treating elements there is also a movement imparted to the cleaning/treating elements when pressure is applied to the elements such as by contacting the teeth thereby causing the resilient membrane to move in response to the pressure.

Figure 40:
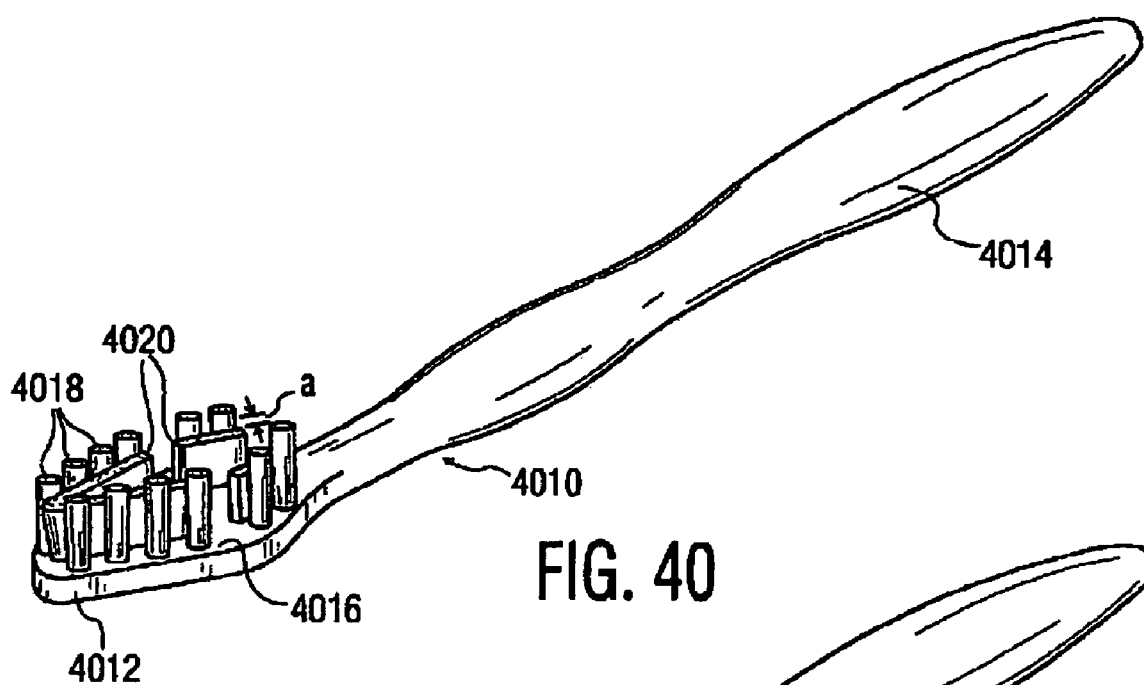
FIG. 40 is a perspective view of a further embodiment of a toothbrush of the present invention wherein the bristle bars are generally in the form of parallelepipeds.

Referring now to FIG. 40 of the drawings, a toothbrush 4010 of this invention includes a body formed of an elongated member with a head 4012 on one end and a handle 4014 on the other. The handle 4014 may be conventional in shape. The head 4012 has a flattened bristle mounting surface or face 4016, from which extend a plurality of bristles having proximal ends attached to the face 4016 and distal ends extending outwardly from the head 4012. As seen in FIG. 40, there are two types of bristle groups, the first type being peripheral bristle tufts 4018, located about the periphery of the head 4012. These peripheral bristle tufts 4018 are generally symmetrical in cross-section, i.e. circular, square, or, if oval or rectangular, having a larger cross-sectional dimension less than about 1.3 times the shorter cross-sectional dimension. Further, these peripheral bristle tufts 4018 have a cross-sectional diameter or larger dimension of from about 1.0 mm to about 2.0 mm, preferably from 1.4 mm to about 1.9 mm, and more preferably from about 1.5 mm to about 1.7 mm. The second type of bristle group shown are bristle bars 4020, which are generally elongated in shape and which are located adjacent to the peripheral bristle tufts 4018 and internal to the head 4012 of the peripheral bristle tufts 4018. Bristle bars 4020 have a cross-sectional length of at least 2.5 mm, preferably at least 3.0 mm and more preferably at least 4 mm. The bristle bars may also be formed as elastomeric walls of rubber or other elastomeric material (e.g., SEBS).

In a preferred embodiment, toothbrush 4010 includes a mechanical vibratory device as described above (not shown in FIG. 40) which causes the head to vibrate. The mechanical vibratory device is located in the head or in a region adjacent to the head and operatively connected to an electric power source. The bristle tufts and bristle bars are moved by the mechanical vibratory device and/or independently of the mechanical vibratory device in a manner so as to provide an enhanced scrubbing action of the teeth and gums. Nevertheless, the head could be driven by other means or used as a manual brush.

Figure 41:
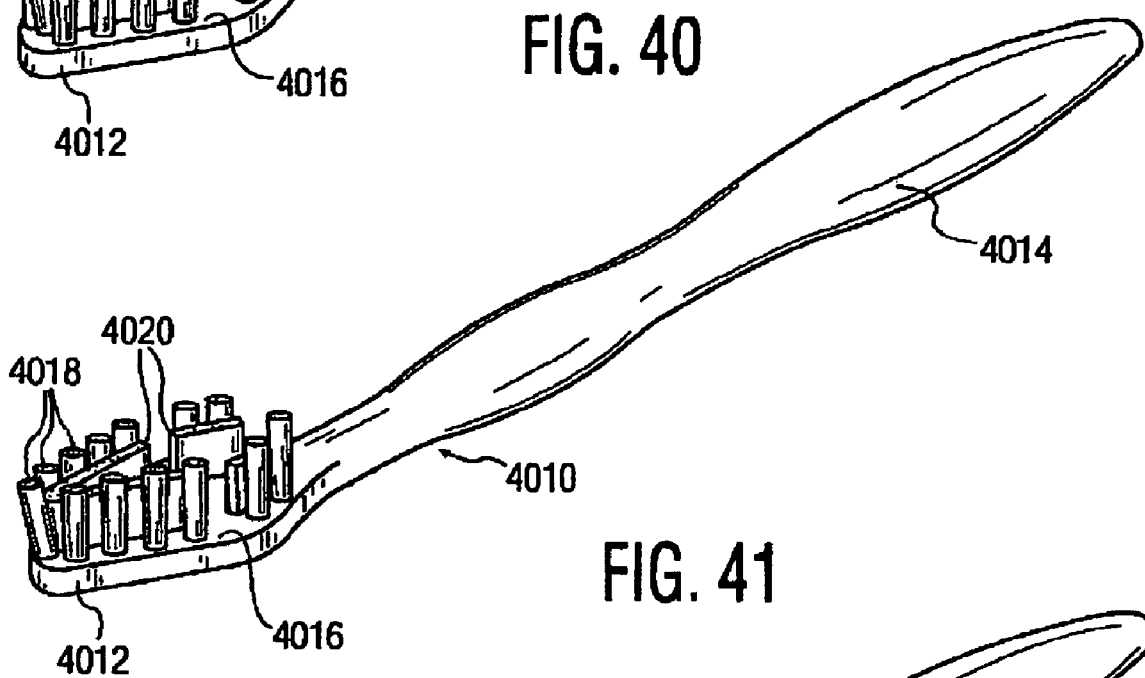
FIG. 41 is a perspective view of another embodiment of a toothbrush of the present invention, wherein the bristle bars have generally curved foot-prints.

As illustrated in FIGS. 40 and 41 the bristle bars 4020 of the present invention can be shaped in a variety of geometric forms, such as substantially parallelepipeds; or alternately having curved foot-prints to conform to the curvature of the toothbrush head 4012; or combinations thereof. The peripheral bristle tufts 4018 can preferably be taller, i.e., in height from the face 4016, than the bristle bars 4020 or any other bristle tufts on the toothbrush. Peripheral bristle tufts 4018 having such extra height over any other bristle tufts within the head 4012 will penetrate into the interproximal areas between teeth for enhanced cleaning therein without interference by such other shorter bristle tufts. It is preferred that the peripheral bristle tufts are from about 9.0 mm to about 13.0 mm in height about the face 4016 of the toothbrush, preferably from about 11 mm to about 12 mm in height. Further, the bristle bars 4020 are preferably at least about 50% to about 85% of the height of the peripheral bristle tufts 4018, so as to provide the desired support to the peripheral bristle tufts 4018.

U.S. Pat. No. 5,511,275 to Volpenhein discloses that in addition to the stiffness characteristics of the bristles, the more tightly bristles are packed together in tufts, the more additional support they will lend each other to enhance their overall stiffness and cleaning ability. Volpenhein further discloses as a measure of this effect a Buttress Factor defined as the cross-sectional area taken up by the bristles divided by the total cross sectional area of the tuft at its base, i.e., from 0 to 1. The higher the Buttress Factor, the greater the stiffness and cleaning ability of the bristles. While Volpenhein discloses toothbrushes having Buttress Factors of from 0.8 to 0.96, the bristle tufts 4018 and bristle bars 4020 in the present invention surprisingly only require a Buttress Factor of from about 0.6 to about 0.75. Preferably the Buttress Factor of both the bristle tufts 4018 and the bristle bars 4020 of the present invention is from about 0.65 to about 0.7, and most preferably about 0.68. This Buttress Factor range is further advantageous in equating closely with DuPont Polymers recommended optimum bristle wear performance packing factor range of 0.63 to 0.74, defined similarly as filament cross-sectional area divided by tuft hole opening. See, DuPont Polymers, Wilmington, Del. 19898 publication Z-1737.

Figure 42:
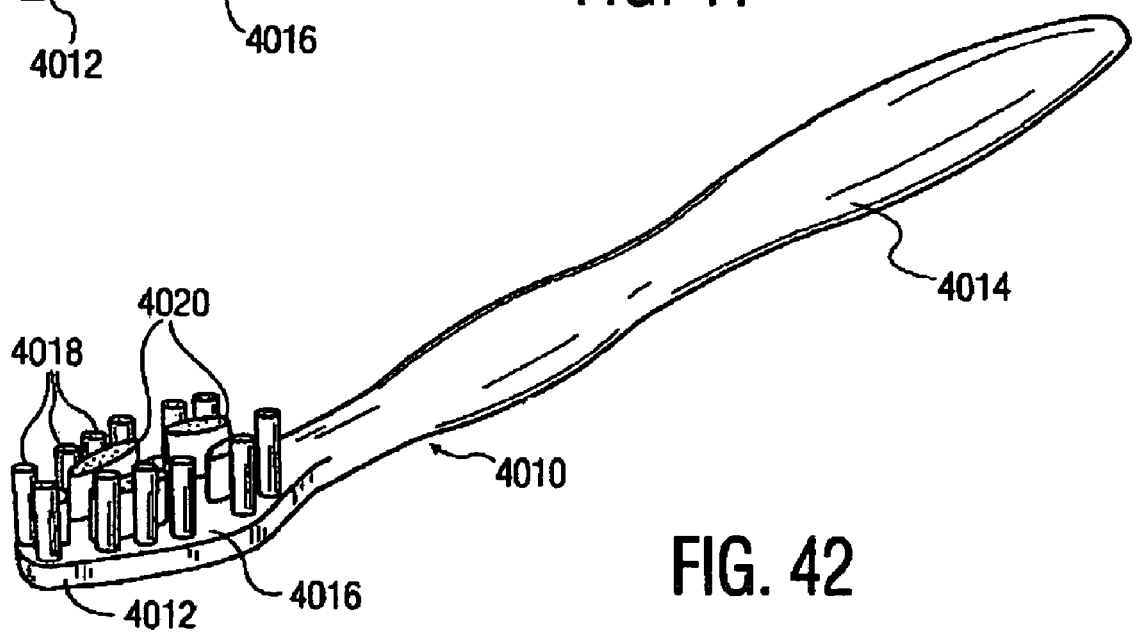
FIG. 42 is a perspective view of a further embodiment of a toothbrush of the present invention, wherein the bristle bars have generally oval footprints.
Figure 43:
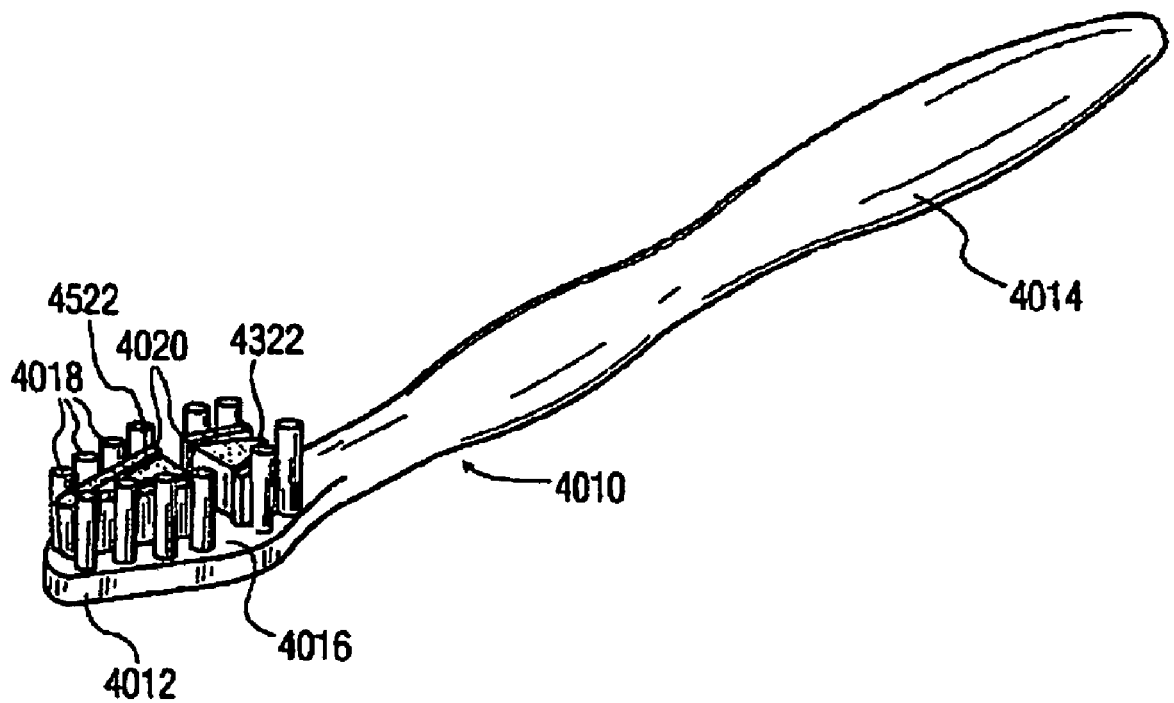
FIG. 43 is a perspective view of an alternative embodiment of the toothbrush shown in FIG. 40, wherein there are additional bristle bars located central to the toothbrush head.

As shown in FIGS. 41, 42 and 43 the bristle bars 4020 may generally have rectangular, curved, or oval foot-prints. The general shape of the bristle bars 4020 is not critical, so long as the bristle bars are of sufficient dimension to provide the adjacent peripheral tufts support during tooth brushing. Considering the simultaneous brushing movement of toothbrushes from the front to the rear of the mouth and up and down; the bristle bars 4020 are preferably of such a length and such a spacing from the peripheral bristle tufts 4018, to provide support to each adjacent peripheral bristle tuft 4018 when the adjacent peripheral bristle tuft is deflected toward the particular bristle bar 4020 at any angle up to 20 degrees from the perpendicular therebetween, preferably up to 30 degrees, more preferably up to 40 degrees and most preferably up to 50 degrees or more.

The width of the bristle bars 4020, shown as dimension "a" in FIG. 40, is preferably at least about "1.0 mm, more preferably at least about 1.5 mm. Further, the narrowest transverse space between each peripheral tuft 4018 and the supporting bristle bar 4020 therefore, are preferably not greater than about 1.5 mm, more preferably not greater than 1.0 mm and most preferably not greater than about 0.7 mm.

Referring again to FIGS. 40 and 41, it can be seen that in each figure a transverse opening is provided between the bristle tufts 4018 and extending through the bristle bars 4020, toward the center of the head 4012; this opening being located middle way up the head 4012. This opening may be provided to enhance the users ability to clean the toothbrush of toothpaste and debris accumulated during brushing, by providing a clear channel for rinse water to the interior" of the head 4012. Alternatively, additional openings can be provided as is illustrated in FIG. 42, to further enhance the ease of cleaning.

Another embodiment of the present invention, as illustrated in FIG. 43, has a head 4012 having extending from its face 4016 the same peripheral tufts 4018 and adjacent bristle bars 4020 internal thereto as the afore-described embodiment; however, in addition to these sets of bristle tufts 4018 and bars 4020, there is a set of additional bristle bars 4522 located central to the head ("central bristle bars"). These central bristle bars, illustrated as wedges in FIG. 43, provide not only additional bristle area for cleaning, but also, enhanced support for the now intermediate within the head located bristle bars 4020, to enhance the overall stiffness and cleaning ability of the toothbrush 4010. These central bristle bars 4522 play have cross-sections other than wedges, such as ovals, egg shapes, or rectangular.

Figure 44:
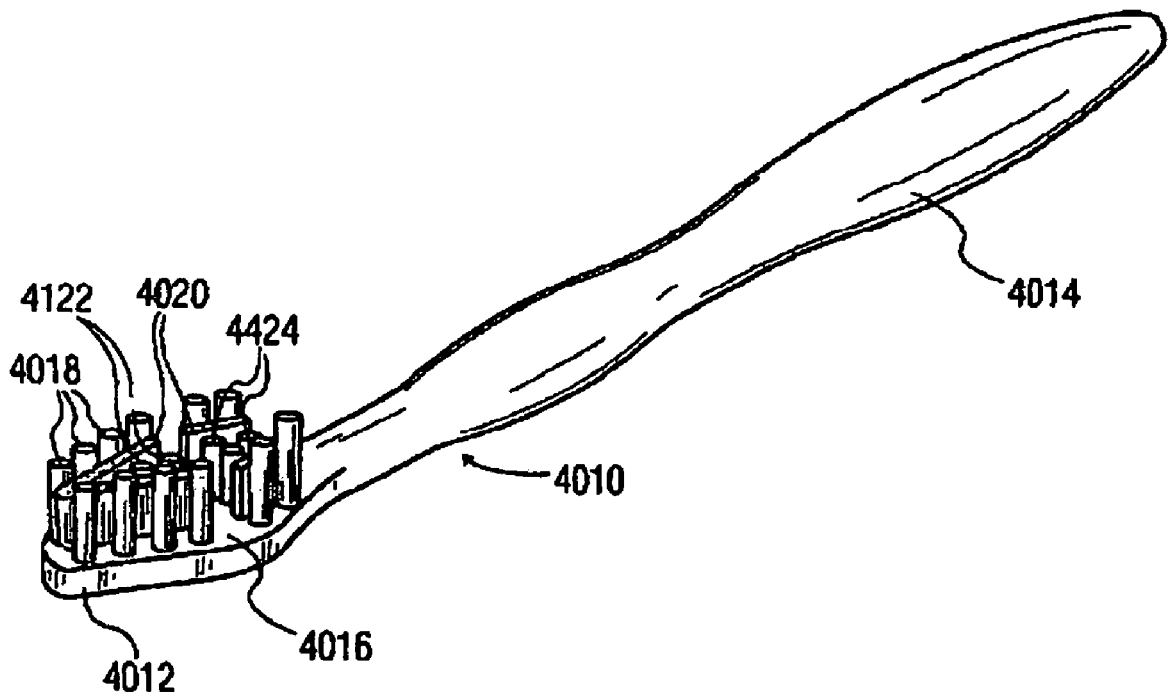
FIG. 44 is a perspective view of an alternative embodiment of the toothbrush shown in FIG. 40, wherein there are additional bristle tufts located central to the toothbrush head.

An alternative embodiment of the present invention shown in FIG. 44 is similar to the embodiment disclosed above for FIGS. 40 and 41, except the central bristle bars 4322 can be replaced by a plurality of central bristle tufts 4424, similar to the individual, peripheral bristle tufts 4018. The height of any such central bristle tufts 4024 above the brush face 4016 can be equal to or less than that of the now intermediate within the head located bristle bars 4020.

Figure 45:
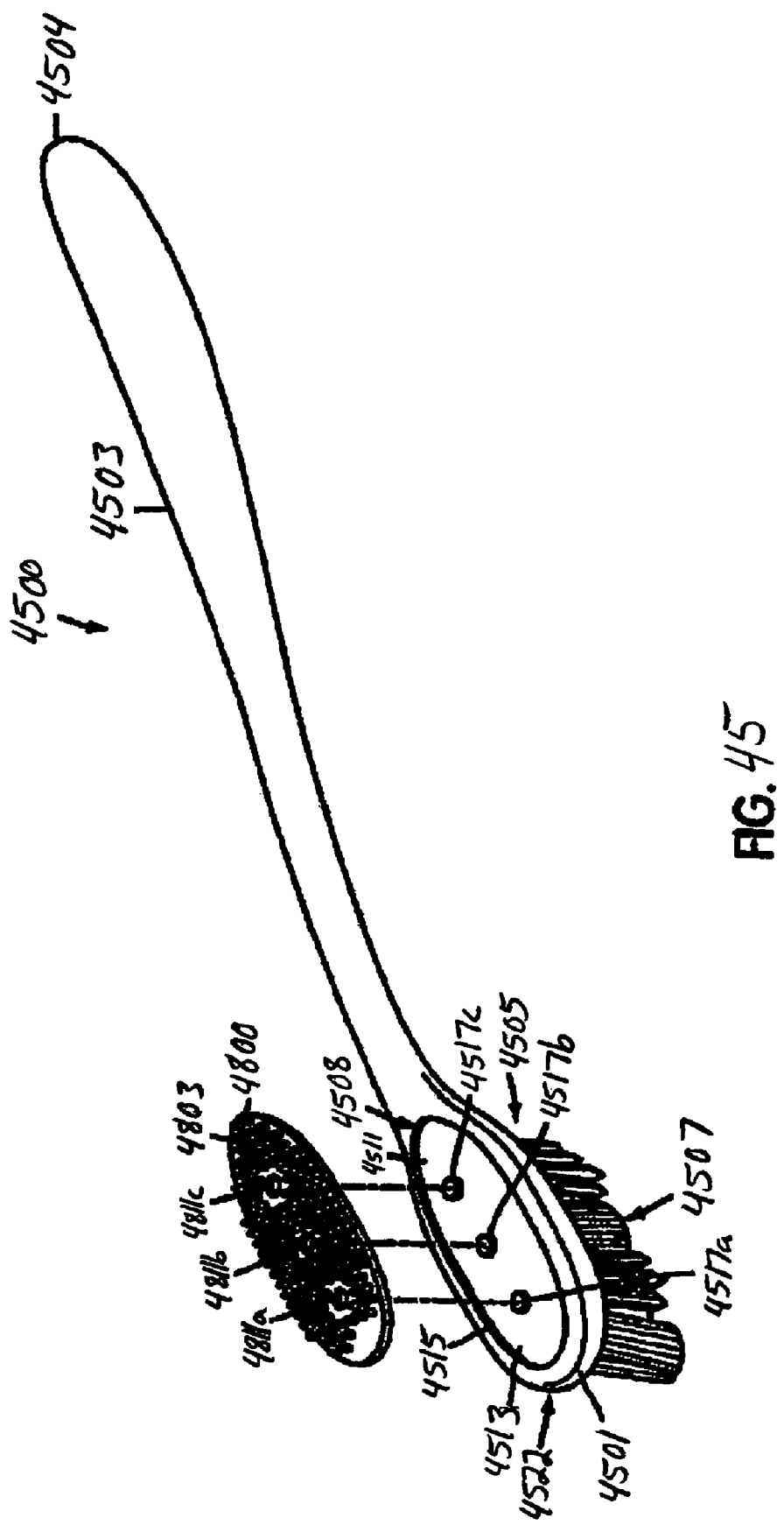
FIG. 45 is an exploded assembly perspective view of an oral care implement according to one or more aspects of an illustrative embodiment.
Figure 52:
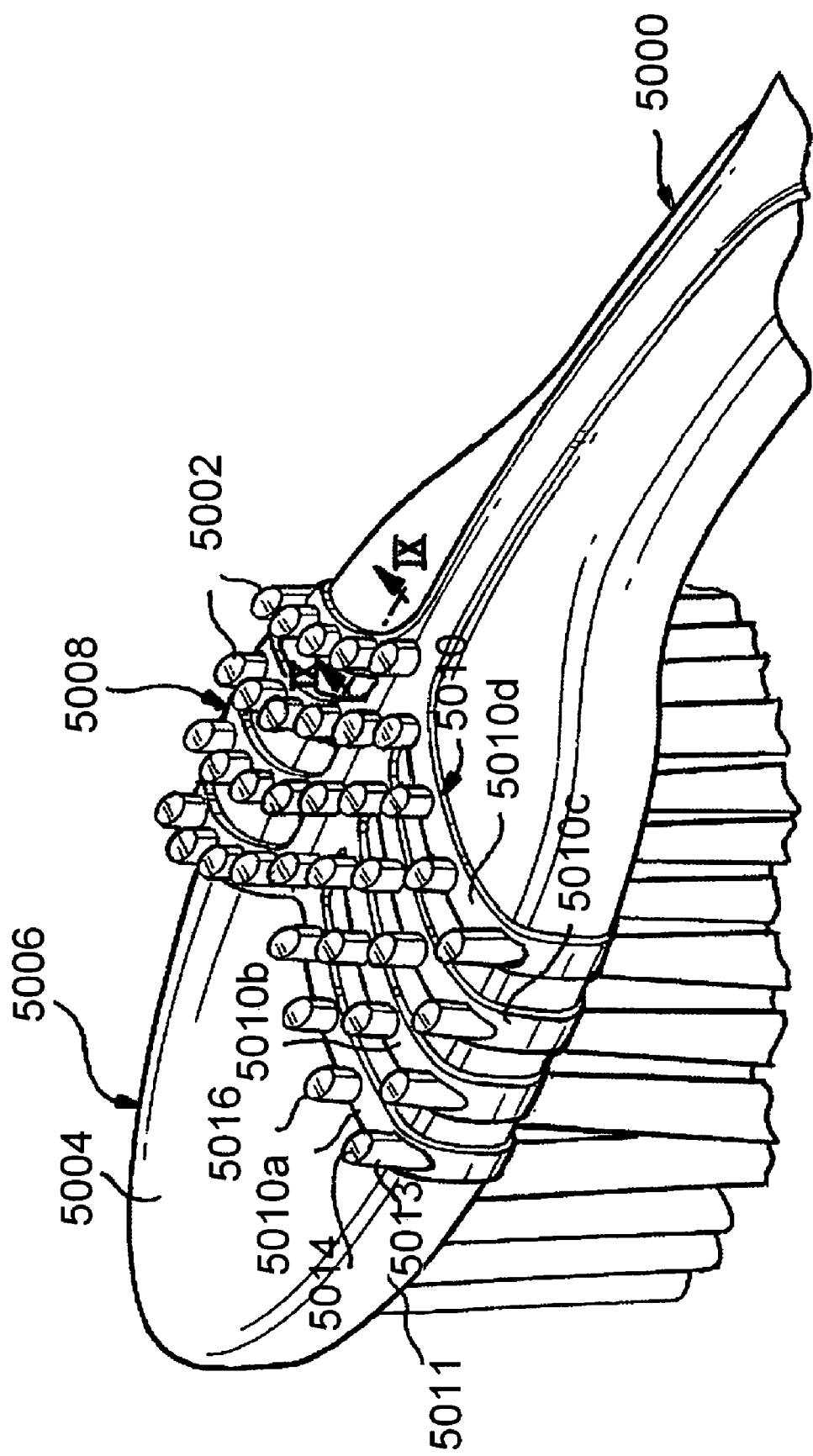
FIG. 52 is a perspective view of a head of a further embodiment of the invention.

FIGS. 45 and 52 show additional embodiments of the invention that are discussed in terms of a toothbrush. For example, toothbrush 4500 is shown as one embodiment in FIG. 45, and toothbrush 5000 as an alternative embodiment in FIG. 52. Nevertheless, the invention could be used in other oral care implements including simply a tissue cleansing implement. They also could be as powered brushes.

Figure 46:
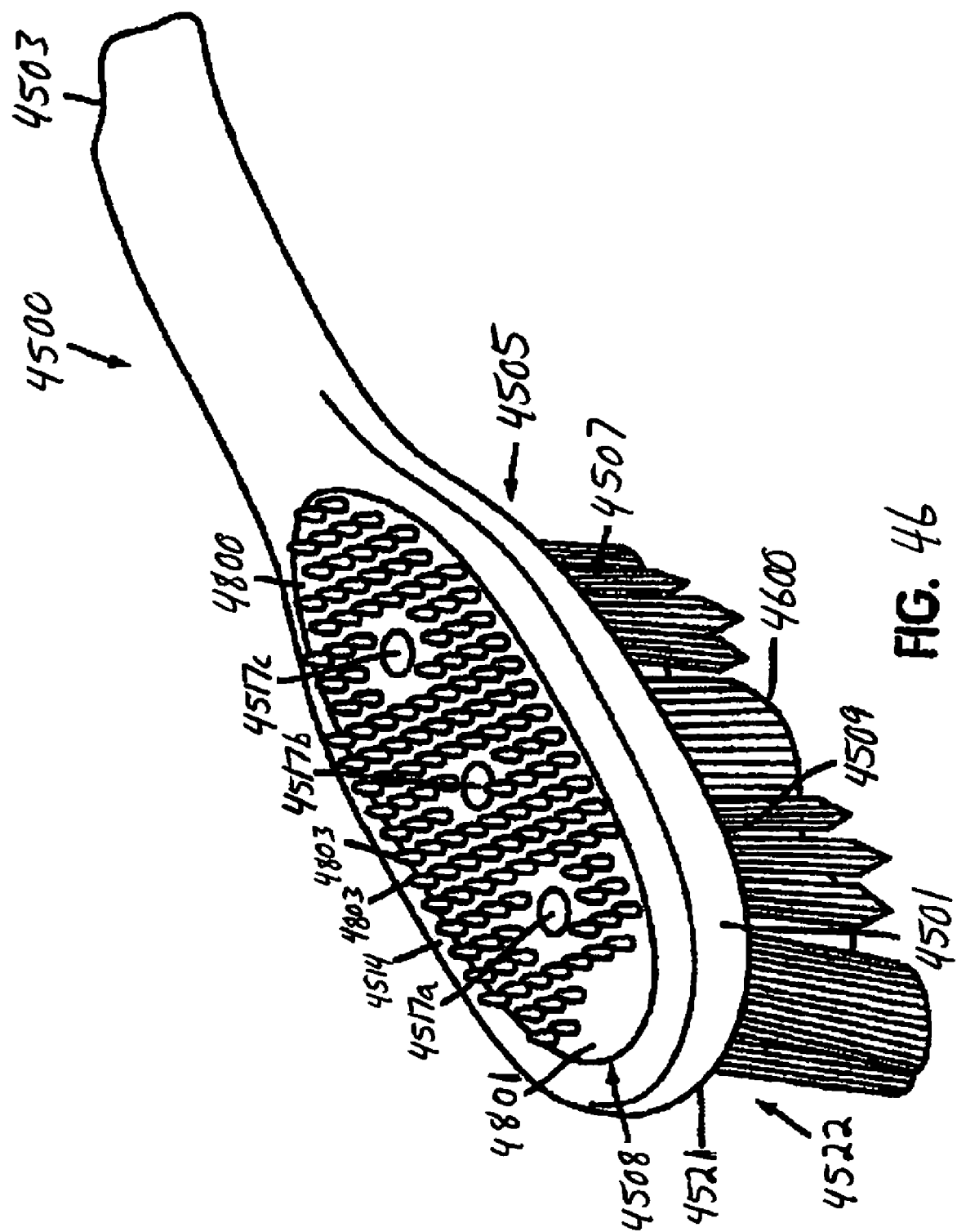
FIG. 46 is an enlarged perspective view of a head of an oral care implement of FIG. 45.

As seen in FIGS. 45-51, an oral care implement in the form of a toothbrush 4500 includes a handle 4503 and a head 4505 which may be used for cleaning the teeth and soft tissue in the mouth, such as the tongue, interior surfaces of the cheeks, lips or the gums. Handle 4503 is provided for the user to readily grip and manipulate the toothbrush, and may be formed of many different shapes and constructions. While the head is normally widened relative to the neck of the handle, it could in some constructions simply be a continuous extension or narrowing of the handle. In one construction, head 4505 has a first face 4506 that supports tooth cleaning elements 4507 (FIGS. 49 and 51) and a second face 4508 that supports a tissue cleanser 4800 (FIGS. 46 and 47). The first and second faces 4506, 4508 are preferably on opposite sides of head 4505. Nevertheless, tissue cleanser 4800 may be mounted elsewhere, such as at the proximal end 4504 of handle 4503. The tissue cleanser 4800 or portions of it may also be located on the peripheral sidewall surface 4501 of head 4505 or extend farther towards the proximate end 4504 of handle 4503 than illustrated.

The elastomeric material of tissue cleanser 4800 may be any biocompatible resilient material suitable for uses in an oral hygiene apparatus. To provide optimum comfort as well as cleaning benefits, the elastomeric material preferably has a hardness property in the range of A8 to A35 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used.

Tissue cleanser 4800 is preferably configured with a multiplicity of tissue engaging elements 4803 (FIGS. 45-48), which in a preferred construction are formed as nubs. Alternative nub constructions 5002, as discussed below, are also illustrated in alternative constructions in FIGS. 52-56. As used herein a "nub" is generally meant to include a column-like protrusion (without limitation to the cross-sectional shape of the protrusion) which is upstanding from a base surface. In a general sense, the nub, in a preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

Such tissue engaging elements 4803 are designed to significantly reduce a major source of bad breath in people and improve hygiene. Nubs 4803 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, nubs 4803 of elastomeric tissue cleanser 4800 provide for gentle engagement with the soft tissue while reaching downward into the recesses of adjacent papillae of the tongue. The elastomeric construction of tissue cleanser 4800 also enables the base surface 4801 to follow the natural contours of the oral tissue surfaces, such as the tongue, cheeks, lips, and gums of a user. Moreover, the soft nubs 4803 are able to flex as needed to traverse and clean the soft tissue surfaces in the mouth along which it is moved.

As seen in FIGS. 46 and 48, in one preferred arrangement of tissue cleanser 4800, nubs 4803 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. With reference to FIG. 48, the base portion 4805 of each conically shaped tissue engaging element 4803 is larger than the corresponding tip portion 4807. In this conically shaped configuration, the base portion 4805 has a wider cross-sectional area to provide effective shear strength to withstand the lateral movement of the tissue cleanser 4800 along the surface of the tongue or other soft tissue surface. The smaller width or diameter of the tip portion 4807 in conjunction with the length of the conically shaped nub 4803 enable the nubs to sweep into the recesses of the tongue and other surfaces to clean the microbial deposits and other debris from the soft tissue surfaces. In the preferred construction, nubs 4803 are able to flex and bend from their respective vertical axes as lateral pressure is applied during use. This flexing enhances the comfort and cleaning of the soft tissue surfaces. In a preferred construction, the thickness or width of the base of the nub in 0.64 mm, and preferably within the range from about 0.51 mm to about 2.00 mm. Tip 4807 of the nubs is 0.127 mm and preferably within a range from about 0.10 mm to about 0.75 mm for optimal penetration between the recesses of papillae of a user's tongue. The length or height of nubs 303, as measured from base surface 301 to tip 307, is preferably 0.91 mm and preferably within range from about 0.5 mm to about 2.5 mm, and most preferably range between 0.75 mm to 1.5 mm. Nevertheless, nubs of other sizes and shapes outside the given ranges can be used.

Alternatively, the tissue cleaning elements 4803 may have other shapes. As one example, the tissue cleanser may have a grated form such as described in co-pending U.S. patent application Ser. No. 10/601,106, incorporated herein by reference.

In a preferred construction, nubs 4803 are disposed on the base surface 4801 of tissue cleanser 4800 in a high density pattern. Each nub 4803 is preferably spaced apart from adjacent nubs 4803 between a range of about 0.5 mm to about 3 mm; more preferably the spacing ranges between 0.7 mm to 2.5 mm, and most preferably between 1 mm to 2 mm. Nevertheless, other spacing ranges are possible. The surface density of the nubs 4803 on base surface 4801 ranges preferably from about 100 to about 600 nubs per square inch. In a more preferred construction of the tissue cleanser, the surface density may range from 200 to 500 nubs per square inch, and most preferably between 300 to 450 nubs per square inch. In one preferred example, tissue cleanser 300 includes about 400 nubs per square inch of surface area. The surface density features in conjunction with the height of the nubs 4803 enables the tissue cleanser to provide enhanced cleaning of the soft tissue surfaces with improved comfort. Nonetheless, other surface densities are possible.

As seen in FIG. 47, nubs 4803 are preferably disposed in longitudinal rows in a direction generally parallel to the longitudinal axis a-a. Further, nubs 4803 are disposed in transverse rows R1, R2 on an axis parallel to base surface 4801 and generally perpendicular to the longitudinal axis a-a. In one preferred construction, adjacent nubs 4803 are provided on the base surface 4801 in a staggered arrangement. For example, adjacent transverse rows of nubs R1 and R2 have nubs 4803 that are not directly behind each other. A first nub is said herein to be "directly behind" second nub when it is located within the lateral bounds of the second nub extending in a longitudinal direction. This configuration enables improved cleaning of the soft tissue surfaces by facilitating the removal of microflora and other debris, and especially from the recesses of adjacent papillae of the tongue. Nonetheless, the nubs could be arranged randomly or in a myriad of different patterns.

Tongue cleanser 4800 is preferably formed by being molded to head 4505, although other manufacturing processes could be used. With reference to FIGS. 45 and 47, tissue cleanser 4800 is preferably molded within a basin or a receiving cavity 4511 in face 4508 of head 4505. The receiving cavity 4511 has a lower base surface 4513 and a peripheral sidewall 4515 extending away from the lower base surface 4513. In one mounting arrangement, nubs 4803 of the tissue cleanser 4800 are exposed for use with the base surface of the tissue cleanser 4800 being flush or recessed relative to the surface 4514 of the head. Nevertheless, other orientations are possible. Also, base surface 4801 of the tissue cleanser could be embedded in head 4505 or covered by another layer with nubs 4803 projecting through appropriate openings.

As can be seen in FIGS. 45 and 47, face 4508 also preferably includes one or more peg members 4517a-c disposed within basin 4511. Peg members 4517 form anchor points against the opposing mold to prevent the head from moving under the pressure of the injection molding. As a result, tissue cleanser 4800 preferably includes one or more complementary apertures 4811a-c which exposes the tops of peg members 4517a-c. Although, the pegs are illustrated in alignment along the centerline of the head (e.g., longitudinal axis a-a), the pegs could have many different positions. Further, the pegs and basin are preferably both included with head 4505, but either could be used without the other.

Alternatively, basin 4511 and peg members 4517a-c may be provided to position and hold a previously molded tissue cleanser, although these constructions are not necessary to use such a previously molded tissue cleanser.

Peg members 4517a-c may take on a variety of shapes and lengths. With continued reference to the FIGS. 45 and 47, head 4505 includes peg members 4517a-c extending away from the lower base surface 4513 of basin 4511 to the height of the peripheral sidewall 4515. The peg members 4517a-c are shaped in the form of a cylinder, but other shapes and lengths of the peg members 4517a-c are possible. While the molding process would preferably bond the tissue cleanser to the head, the tissue cleanser could be performed and attached by adhesive or other known means.

As shown in FIGS. 45-47, tissue cleanser 4800 is preferably formed as a pad composed of a soft and pliable elastomeric material for comfortable cleaning and effective removal of bacteria and debris disposed on the surface of the tongue, other soft tissue in the mouth and even along the lips. The tissue cleanser 4800 also provides effective massaging, stimulation and removal of bacteria, debris and epithelial cells from the surfaces of the tongue, cheeks, gums or lips.

In the construction of FIGS. 45-51, tissue cleansers 4800 may rub against the inside surfaces of the cheeks or lips, and on the sides of the tongue while the user brushes his or her teeth, and thus provide a desired massaging, stimulation and cleaning of various soft tissue surfaces within the mouth. For example, during brushing of the facial tooth surfaces, tissue cleanser 4800 is disposed on the outer face 4508 of head 4505 to naturally rub against the oral surfaces of the cheek. As a result, enhanced cleaning is attained without additional cleaning steps. Further, some users may sense a stimulating tingle on the cheek surfaces that leads to a positive user reaction, and even enjoyment of the comfortable feel of the tissue cleanser along the soft tissues surfaces in the mouth. Tissue cleanser 4800 may also be additionally rubbed on the cheeks, tongue, etc., as desired for further cleaning aside from the contact that may occur while brushing the teeth.

Figure 49:
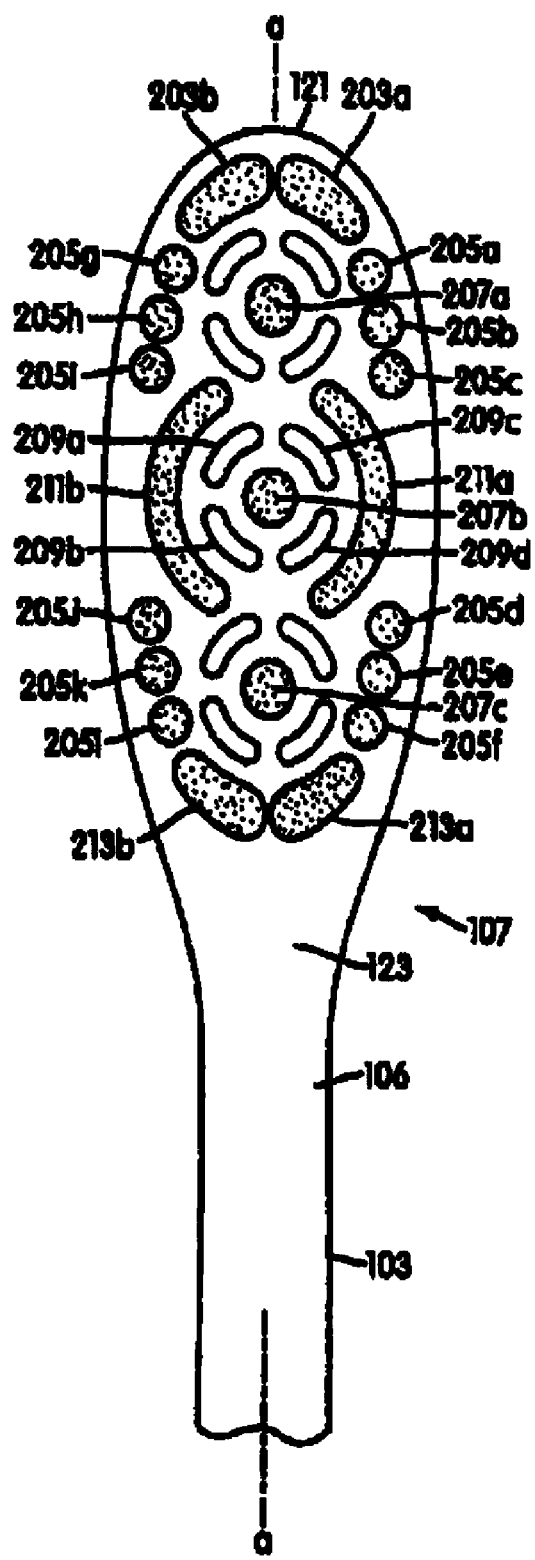
FIG. 49 is a plan view of the oral care implement of FIG. 45 illustrating at least one tooth cleaning configuration.
Figure 50:
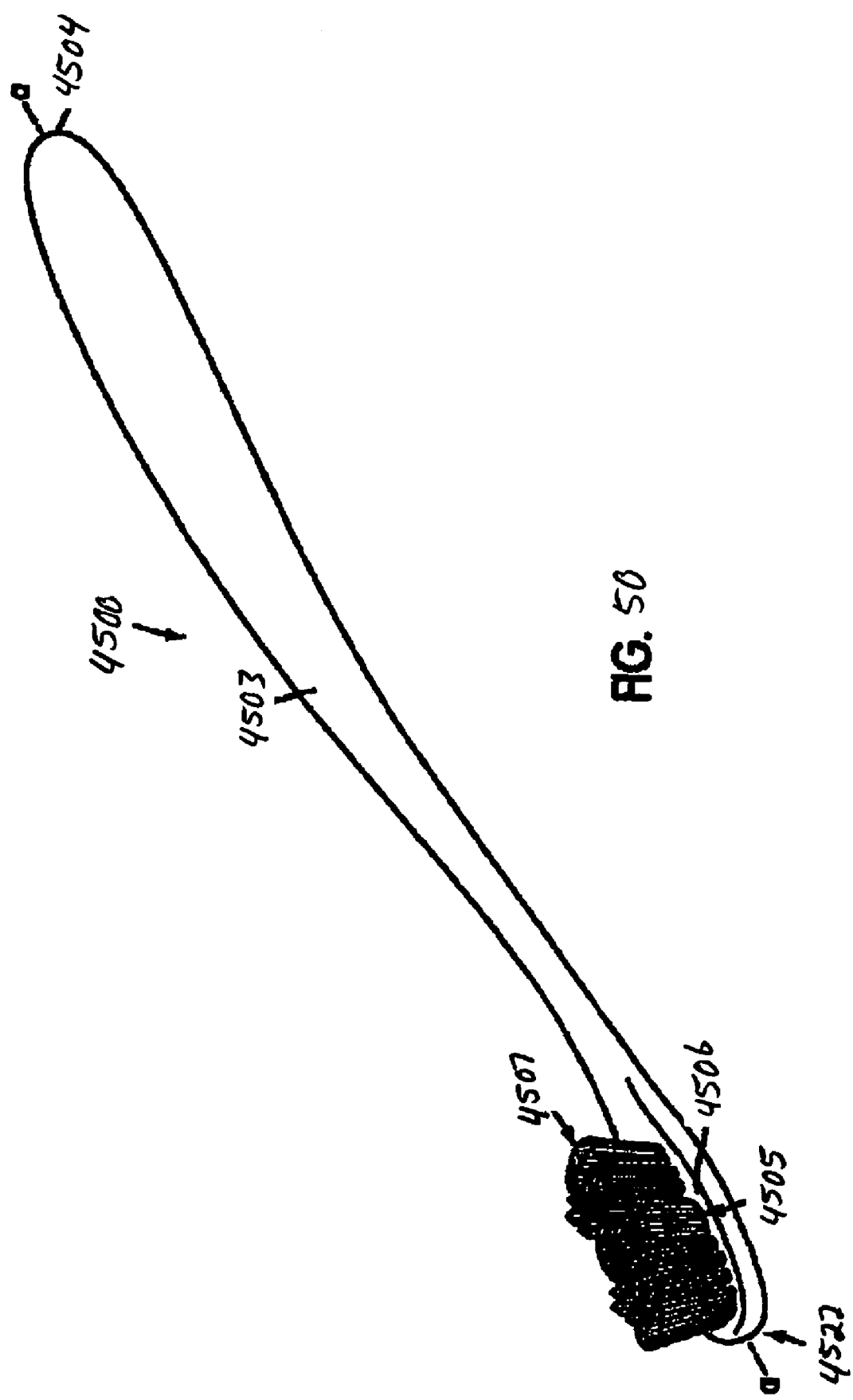
FIG. 50 is another perspective of the view of the oral care implement of FIG. 45.

Referring to FIGS. 49 and 50, the tooth cleaning elements 4507 of head 4505 may include a variety of tooth cleaning elements which can be used for wiping, cleaning and massaging the user's teeth and gums. Any suitable form of tooth cleaning elements may be used. The term "tooth cleaning elements" is used in a generic sense which refers to filament bristles or elastomeric fingers or walls that have any desirable shape. In the illustrated example of FIG. 49, tooth cleaning elements 4507 include distal tooth cleaning elements 4603a-b disposed at a distal tip 4521 of head 4505, peripheral tooth cleaning elements 4605a-l, longitudinal tooth cleaning elements 4607a-c disposed along longitudinal axis a-a, arcuate tooth cleaning elements 4609a-d and 4611a-b, and proximal cleaning elements 4613a,b. Tooth cleaning elements 4605, 4607, 4611 and 4613 are preferably provided as tufts of bristles whereas tooth cleaning elements 4609 are preferably formed as elastomeric walls. Nevertheless, other forms and types of tooth cleaning elements may be used.

Figure 51:
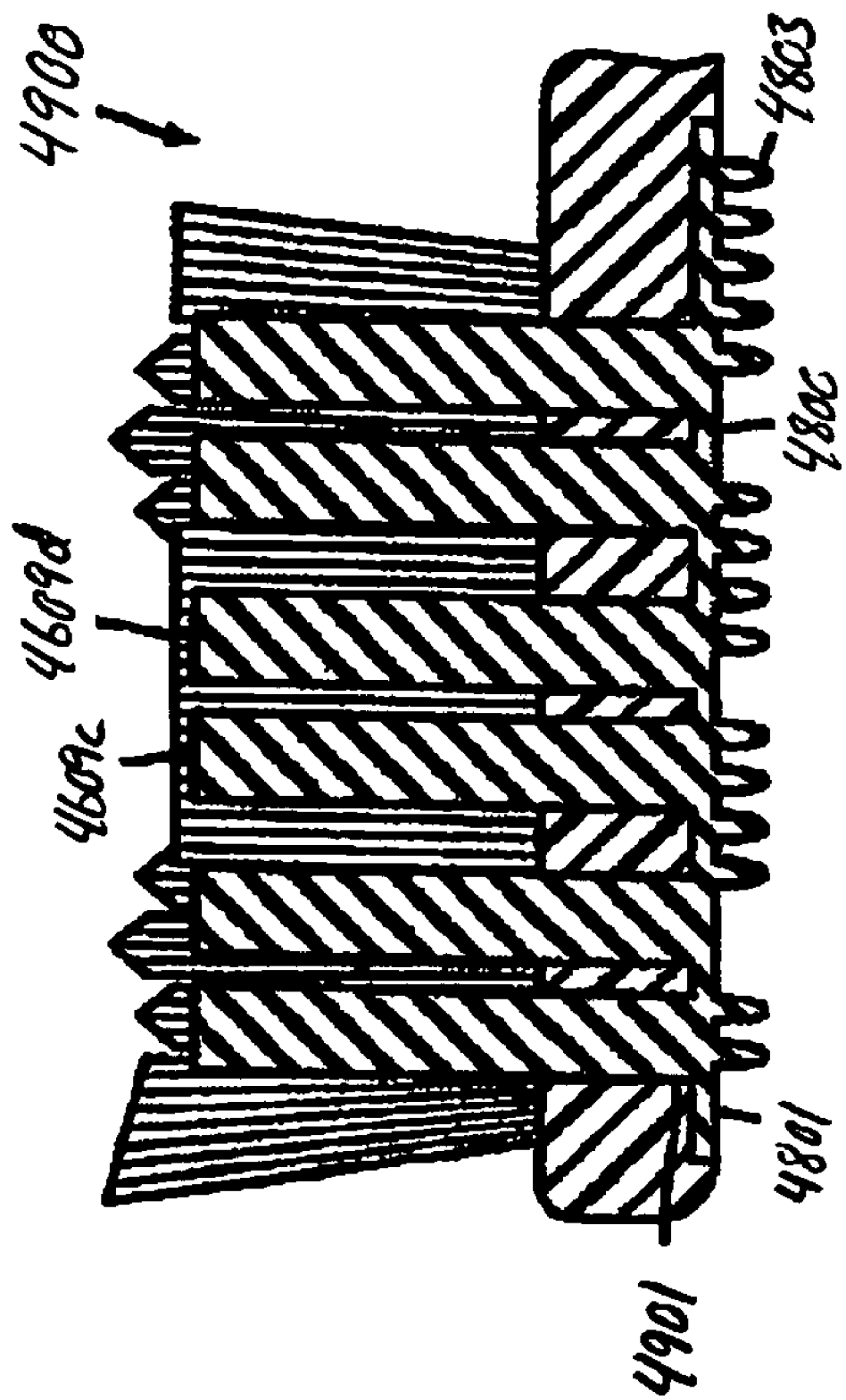
FIG. 51 is a section view of an alternative construction of the head of the oral care implement of FIG. 45.

FIG. 51 illustrates a sectional view of an alternative arrangement of a head 4900 of a toothbrush. Head 4900 is similar in construction to head 4505, except that tooth cleaning elements 4609a-d are integrally formed with tissue cleanser 4800. To accomplish the alternative construction, head 4900 has appropriately sized ports or openings 4901 to allow the elastomeric material to flow through the head during an injection molding process. In this construction, tooth cleaning elements 4609a-d and tissue cleaner 4800 are formed with the same elastomeric material. Thus, head 4900 may include at least one elastomeric tooth cleaning element formed as a unitary member with tissue cleanser 4800.

In FIG. 52, toothbrush 5000 includes a plurality of nubs or other projections 5002 protruding from a back side 5004 of head 5006 as a cleanser 5008 of soft tissue in the mouth. Teeth cleaning elements 5016 preferably extend from a front side 5005 of head 5006. The projections 5002 are preferably arranged seriatim along at least one narrow base or pad in the form of a strip 5010 fixed to the head 5006. In the illustrated example, a plurality of generally parallel strips 5010a, 5010b, 5010c, 5010d are fixed in a generally concave shape facing away from the handle. In this one construction, the strips extend along back side 5004 of head 5006 and each sidewall 5011, although extensions along the sidewalls are not necessary. Any number of strips could be included. The strips could define virtually any shape or orientation on the head. For example, strips 5010 could have any of the shapes disclosed for the ridges in co-pending U.S. patent application Ser. No. 10/989,267, filed Nov. 17, 2004, entitled "Oral Care Implement," which is incorporated herein by reference. In the illustrated construction, strips 5010 are interconnected by an axial stem 5012 which extends into the handle and forms a part of the grip for the user. Further, this handle extension or even the stem is of course not necessary.

Figure 53:
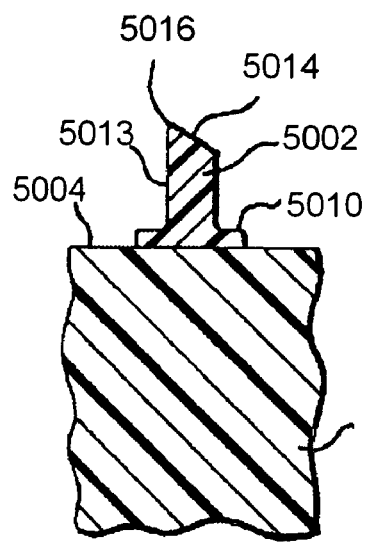
FIG. 53 is a partial cross-sectional view taken along line IX-IX in FIG. 52.
Figure 54:
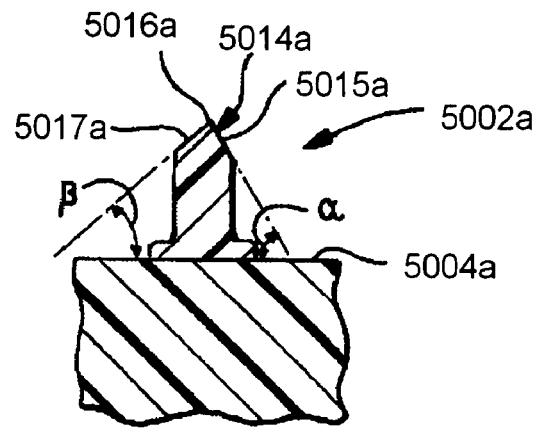
FIG. 54 is a partial cross-sectional view of another embodiment of the invention taken along line IX-IX in FIG. 52.

In one construction, each projection 5002 is generally columnar and formed with a width W of about 1.1 mm and a height H of about 1.7 mm (FIG. 53). The projections are spaced apart from each other along strip 5010 a distance of about 1.0 mm. These height, width and spacing dimensions could, however, vary widely. In the illustrated embodiment, projections 5002 each includes a peripheral wall 5013 protruding outward from base 5010, and an inclined distal end surface 5014 at an angle of about 50 degrees to side surface 5004 of head 5006. The inclined end surface 5014 defines a narrow top edge 5016 along a portion of peripheral wall 5013, which is advantageous for cleansing the tongue and other soft tissue. Although the end surfaces 5014 are shown to be inclined in the same direction, they could be inclined in different directions.

In an alternative construction (FIG. 57), head 5006 is additionally formed with at least one elongate ridge 5025. With this arrangement, the user is provided with a cleanser that obtains a beneficial dual cleaning effect by moving the discrete projections 5002 and the ridge 5025 across the tongue or other tissue. In the illustrated example, ridge 5025 is a curved, elongate projection protruding generally outward along the outer edge of the remote end 5027 of the head. Nevertheless, other arrangements, locations and shapes are possible. Additional ridges could also be provided. In one preferred construction, ridge 5025 is molded as one-piece with the head and formed of a relatively hard plastic such as polypropylene. The ridge, however, could be formed separately from the head and/or composed of other materials that are compatible for oral care implements.

In one construction, ridge 5025 is, as noted above, formed of a relatively hard material (e.g., polypropylene), while projections 5002 are formed of a relatively soft material (e.g., a thermoplastic elastomer). This use of dual materials enables the benefits of both materials to be gained. The cleanser includes the firm engagement of the relatively hard scraper blade in ridge 5025 and the relatively soft discrete projections that flex and turn as they dig into the tongue or other tissue.

Figure 57:
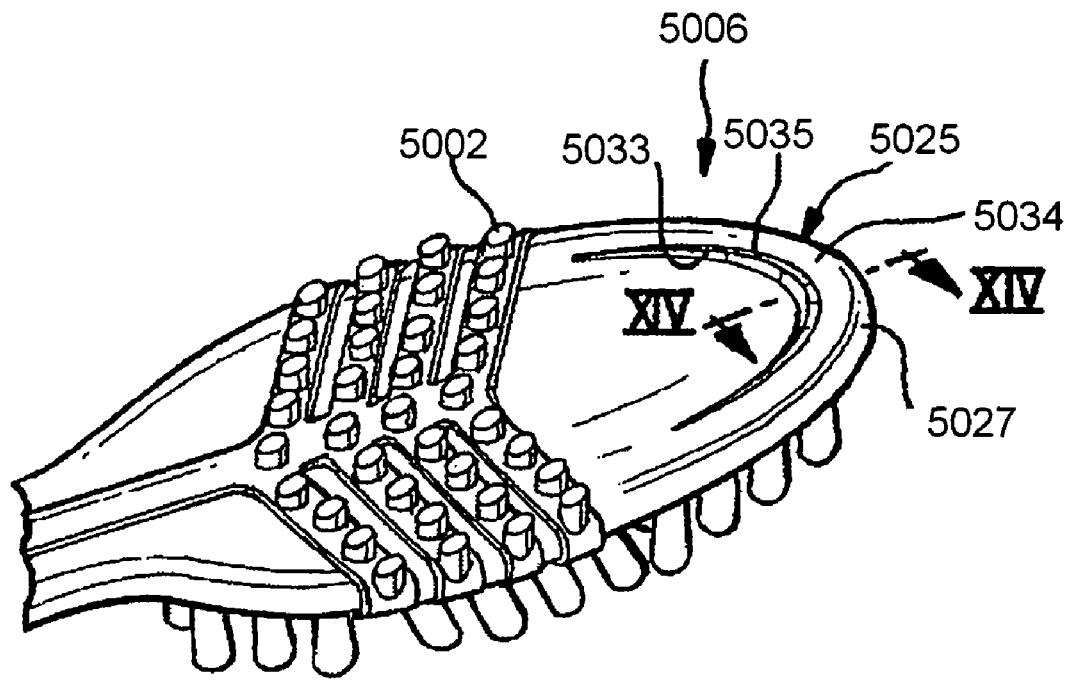
FIG. 57 is a partial perspective view of yet another oral care implement in accordance with the present invention.
Figure 58:
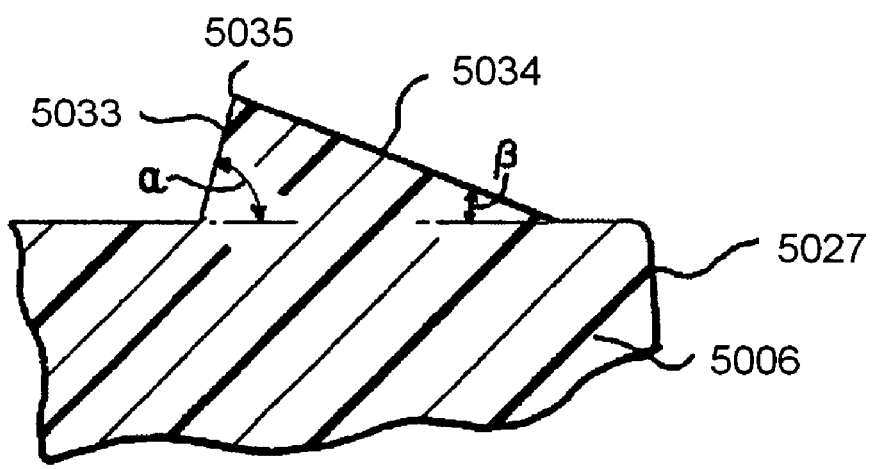
FIG. 58 is a partial cross-sectional view taken along line XIV-XIV in FIG. 57.

As seen in FIGS. 57 and 58, ridge 5025 is defined by a pair of opposite sidewalls 5033, 5034 which meet to form a scraper edge 5035. While edge 5035 is relatively narrow in this construction, it could be substantially widened. In one embodiment, sidewalls 5033, 5034 are formed with different slopes relative to side 5004 of head 5006, though they could have the same slope. In one preferred construction, sidewall 5033 is formed with a steeper slope than sidewall 5034 to define a more aggressive scraping action as the head is pulled across the tongue by the user. The shallower slope of sidewall 5034 facing generally away from the handle, makes the ridge less prone to pushing the tongue biofilm farther back in the throat as the ridge is pushed back toward the throat. In a preferred embodiment, sidewall 5033 is oriented at an angle α of 62 degrees relative to side 5004, whereas sidewall 5034 is oriented at an angle β of 43 degrees. Other angles could also be used for both sidewalls.

In another alternative construction (FIG. 54), each projection 5002a is provided with an end surface 5014a having two inclined end face portions 5015a, 5017a and a top edge 5016a. As with ridge 5025, end face portion 5015a, generally facing toward the handle, is preferably inclined at a steeper angle relative to side 5004a than end face portion 5017a, although other arrangements including end face portions having the same inclination can be used. As one example, end face portion 5015a is oriented at an angle α of 62 degrees relative to side 5004a, and end face portion 5017a is oriented at an angle β of 43 degrees. The steeper angle of end face portion 5015a provides a more aggressive scraping action as the head is dragged out of the mouth. The shallower angle of end surface 5017a makes the projection less prone to pushing the tongue biofilm farther back in the throat.

Of course, other projections can be used. For example, each projection could include a non-inclined distal end or an end that tapers to a pointed tip. The projections could have a wide variety of shapes beyond the cylindrical shape shown in FIG. 52. For example, the projections could have a conical shape, irregular cross sections, or be inclined to the back side 5004. Moreover, the projections may also be ridge shaped to extend entirely or partially along the length of strip 5010.

In a preferred construction, projections 5002 and strip 5010 are formed as a one piece member molded or otherwise secured to head 5006. The projections and strip are preferably formed as a one-piece member of a resilient thermoplastic elastomer such as styrene-ethylene/butylene-styrene block copolymer (SEBS) manufactured by GLS Corporation, but could be composed of other resilient materials, hard materials, or a combination of materials such as disclosed in U.S. patent application Ser. No. 11/011,605, filed Dec. 15, 2004, entitled Oral Care Implement, incorporated herein by reference. The projections and strips could also be formed of the same substance as head 5006 (e.g., polypropylene), but have a different color or the like to define it a different material from the head and thereby create at least a visually appealing brush.

Figure 55:
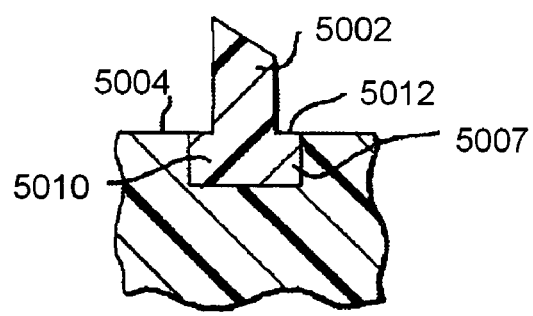
FIG. 55 is a partial cross-sectional view of a further embodiment taken along line IX-IX in FIG. 52.
Figure 56:
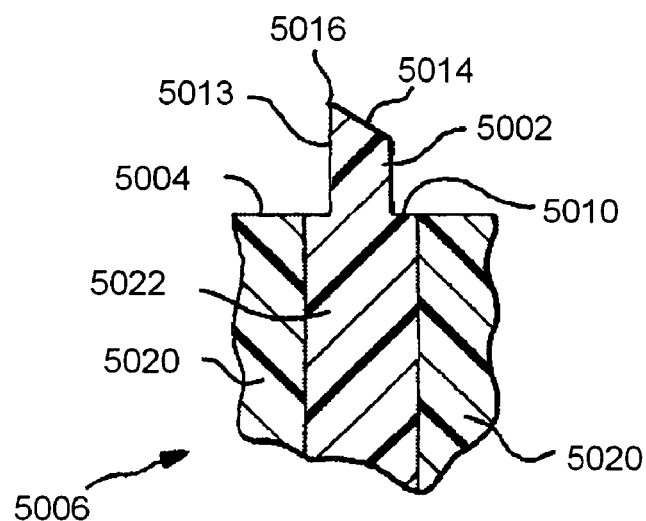
FIG. 56 is a partial cross-sectional view of an additional embodiment taken along line IX-IX in FIG. 52.

In one construction, strips 5010 are molded to overlie a generally planar surface 5004 of head 5006 (FIG. 53). Nevertheless, channels 5007 could be formed in side 5004 to receive strips 5010 therein so that side 5004 and the outer surfaces 5012 of strips 5010 having projections 5002 are generally co-planar (FIG. 55). Additionally, the strips of resilient material could be formed as an integral part of the head construction (FIG. 56). More specifically, in this alternative construction, the head includes a plurality of first members 5020 joined together by a resilient second member 5022 that acts as a living hinge to permit the first members to move relative to each other during use of the toothbrush. The second member also forms the base 5010c of soft tissue cleanser 5006 provided with projections 5002. Additionally, as discussed in regard to toothbrush 4900, projections 5002 or 5002a can be integrally formed as a one-piece member with elastomeric tooth cleaning elements extending in an opposite directions from the head.

The following examples are set forth as representative of the improved operation of the present invention. These examples are not to be construed as limiting the scope of the invention.

EXAMPLE 1

The performance nature of a toothbrush can be measured using known oral malodor assessment methods. A study was conducted to evaluate the performance of a toothbrush provided with an elastomeric tissue cleanser having conically shaped nubs, such as the preferred construction of toothbrush 4500 discussed above. Human test subjects participated in the study. There was a washout or normalization period prior to testing of about 7 days in which the test subjects brushed twice a day with a fluoride dental cream (see Table 1). After the washout period, the test subjects were asked to refrain from any oral hygiene (brushing, rinsing, and flossing), eating and drinking prior to oral testing. A baseline volatile sulfur compound (VSC) sample was taken from each of the test subjects. In the study for overnight odor control, the test subjects brushed their teeth for one minute with a fluoride dental cream (see Table 1) using toothbrush 4500 provided with the above noted tissue cleanser 4800. Subsequently, the subjects cleaned their tongue surface with the tissue engaging elements of the toothbrush for ten seconds. The test subjects slept overnight and returned for post treatment. VSC samples were taken at the ten-hour time point from the previous day cleaning. In the illustrative example, use of the toothbrush reduced oral VSC about 60% verses brushing the teeth alone as measured from a baseline ten hours after use. The VSC readings were obtained by gas chromatography.

EXAMPLE 2

In another study of the above-noted toothbrush 4500, there was a washout or normalization period prior to testing of about 7 days which the test subjects brushed twice a day with a fluoride dental cream (see Table 1). The test subjects were asked to refrain from any oral hygiene (brushing, rinsing, and flossing), eating and drinking before testing. After the washout period, the test subjects provided a baseline tongue bacteria sample by swabbing a side of the back of the tongue with a sterile cotton swab. The test subjects brushed their teeth with a fluoride dental cream (see Table 1) for one minute with the toothbrush having the above-noted tissue cleanser. Subsequently, the test subjects cleaned their tongue surface with a preferred construction of the tissue engaging elements 4800 of the toothbrush 4500 for ten seconds. Two hours after the cleaning of the tongue surface, a tongue bacteria sample was taken from a side of the back of the tongue with a cotton swab. In the illustrative example, use of the tissue engaging elements controlled more odor causing tongue bacteria than simply brushing the teeth alone. Use of the tissue cleanser 4800 demonstrated a tongue bacteria log reduction of over 0.8 Log colony forming units/ml two hours after use on the tongue.

EXAMPLE 3

In another study of the above-noted toothbrush, a MTT assay was used to examine the viability of the epithelial cells collected from the oral cavity prior to and after the use of the toothbrush with the noted tissue cleanser. The MTT Assay was based on the enzymatic reduction of the tetrazolium salt MTT [3-(4,5-dimethylthiazol-2-yl)-2,5-diphenyl-tetrazoliumbromide ++ +] in living, metabolically active cells. The reaction was carried out in situ in test tubes, and the reaction product, a purple-colored formazan soluble in dimethylsulfoxide, was measured colormetrically using a multiwell plate reader. Advantageously, the MTT Assay offers a high degree of precision, ease of use, and suitability for the purpose for large scale chemosensitivity testing.

Following a 7-day washout period, the test subjects reported to a test site without prior eating, drinking, or performing oral hygiene. The test subjects provided salivary rinse samples by rinsing their oral cavity with 9 ml of sterile water for 10 seconds and then discharging the water from the rinse into a tube containing 10× sterile phosphate buffered saline (PBS) solution. The samples were refrigerated for approximately 30 minutes before the MTT Assay was run. The test subjects brushed their teeth under supervision for one minute using a fluoride dental cream (see Table 1) followed by 10 seconds of tongue cleaning with the tongue cleanser 4800 of the preferred construction. Approximately 30 minutes after brushing and tongue cleaning, the test subjects provided a rinse sample in the manner described previously.

The pre-rinse samples and post-rinse samples were centrifuged for 15 minutes at about 3000 RPM. The supernatant, e.g., clear liquid, was removed and the pellet was resuspended in 2.5 mL of PBS. The samples were vortexed for 5 seconds, then 2.5 ml of MTT Solution was added. The samples were subsequently incubated in a gently shaking waterbath set at 37° C. for 2 hours. Following the 2 hour incubation period, the samples were centrifuged for 15 minutes at about 3000 RPM. The supernatatant was siphoned out and 3 mL of detergent (0.04 N Acid Isopropanol) was added to dissolve purple crystals. An increase or decrease in MTT conversion was spectrophotometrically quantified. From each sample, 200 µl of each was added to 96 well plates and the optical density was measured at 570 nm and compared to a negative buffer control. In the illustrative example, one minute of brushing followed by 10 seconds of use of the tissue cleanser reduced oral epithelial cells about 72% as determined by a MTT assay protocol.

EXAMPLE 4

In another study, human test subjects provided baseline VSC samples via a Halimeter™ (i.e., a sulfide meter). A Halimeter™ uses an electrochemical, voltammetric sensor which generates a signal when it is exposed to VSC such as, sulfide and mercaptan gases and measures the concentration of hydrogen sulfide gas in parts per billion. The test subjects brushed their teeth under supervision for one minute with the preferred construction of a toothbrush having the above noted tissue cleanser. Then, the test subjects used the noted toothbrush to provide six strokes on the tongue surface. A subsequent VSC sample was taken from the test subjects two hours after the brushing stage. In this illustrative example, use of a toothbrush with the tissue cleanser reduced the measured VSC in the mouth odor over 35% from a baseline measured two hours after use.

EXAMPLE 5

In one other study, after a washout period, human test subjects rinsed their mouths with sterile water to provide a baseline sample for viable epithelial cell analysis with the MTT assay. The subjects brushed their teeth under supervision for one minute with the preferred construction of the toothbrush having the above-noted tissue cleanser. Then, the test subjects used the tissue cleanser to provide six strokes on the tongue surface. The test subjects provided a post rinse sample for analysis. The samples were tested and analyzed in the manner as discussed with respect to Example 3. In this example, use of the toothbrush reduced oral epithelial cells by about 92% from a baseline as determined by MTT assay protocol.

In the above noted examples, the subjects brushed their teeth using a fluoride dental cream with the formulation in Table 1.

TABLE 1

| % wt. | Ingredient |
|---|---|
| 48.76% | Dicalcium Phosphate Dihydrate |
| 22.0063% | Water |
| 22.00% | Glycerin |
| 4.138% | SO3 Sodium Lauryl Sulfate base - 29% |
| 1.000% | Sodium CMC - 7MF - Food Grade |
| 0.89% | 105 Dental Cream Flavor |
| .76% | Sodium Monofluorophosphate |
| .25% | Tetrasodium Pyrophosphate |
| .20% | Sodium Saccharin |

An oral care implement in accordance with the present invention is further illustrated in the form of a toothbrush 6010 including a head 6012 and a handle 6014. Although discussed in terms of a toothbrush, it is understood that the device could be in the form of other oral care implements including simply a tissue cleansing implement.

An oral care implement in accordance with the present invention is illustrated in the form of a toothbrush 6010 including a head 6012 and a handle 6014. While FIG. 59 only illustrates the connection of the handle to the head, the handle is preferably an elongate member to be grasped by the user. The handle 6014 could have any known shape adapted for the manipulation needed to clean the teeth and/or tongue of a user.

The head 6012 with a pair of opposite sides 6016, 6017 is shown with a generally oblong shape, although other known shapes could be used. A plurality of teeth cleaning elements 6020 extend from one side 6016 of the head 6012. The teeth cleaning elements could be bristles and/or elastomeric members of various shapes and sizes. Any form or combination of elements 6020 suitable for cleaning a user's teeth could be used.

The other side 6017 of head 6012 includes at least one ridge and preferably a plurality of elongate ridges 6022 to cleanse the tongue and other soft tissue of the mouth (e.g., the inner surfaces of the cheeks). While the ridges are preferably formed on a head also provided with teeth cleaning elements, they could also be formed on other implements or other parts of the toothbrush. A head of the implement is simply meant to be the operative portion of the implement that is inserted into the mouth for cleaning of the tongue, and does not refer to a particular shape or structure of the head.

Figure 60:
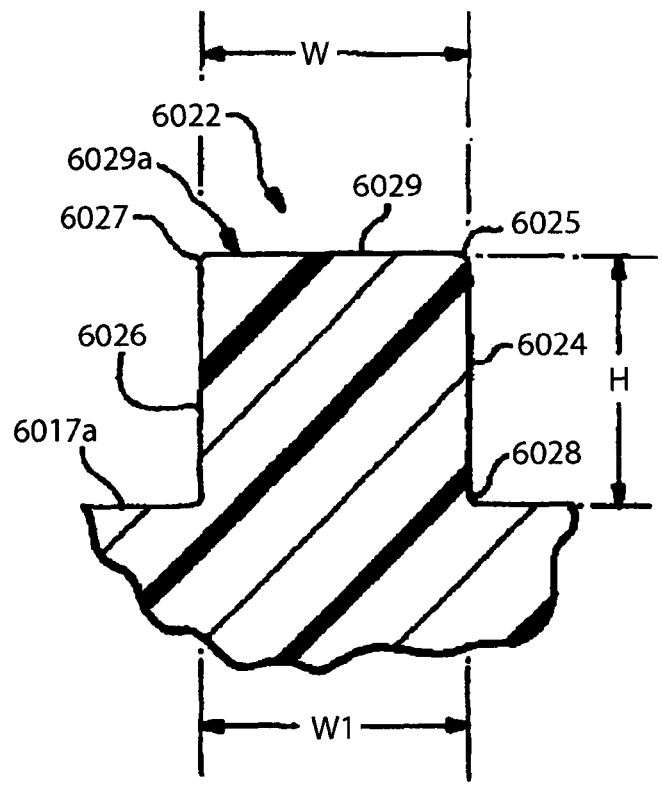
FIG. 60 is a partial cross-sectional view taken along line II-II in FIG. 59.

In one construction of the invention, each ridge 6022 projects orthogonally from a back surface 6017a of the head and has a generally square-like cross-sectional configuration (FIG. 60). The ridge includes a distal end 6029 remote from surface 6017a that forms a contact region 6029a adapted to contact and clean the tongue or other soft tissue in the mouth. In this embodiment, the contact region 6029a is defined between and includes protruding corners or edges 6025, 6027. As can be appreciated, the contact region 6029a has a width W extending transverse to the extension of the ridge across surface 6017a. The width W of ridge 6022 is at least as large as the height H of the ridge (i.e., the distance the ridge extends from surface 6017a). With this width to height relationship, the risk of the ridge cutting or injuring the soft tissue of the tongue or other parts of the mouth is reduced. A narrow ridge that extends outward from head 6012a distance greater than its width has an increased risk of cutting or otherwise injuring the user as compared to a similarly narrow ridge (i.e., one with the same width) that extends from the head a distance less than the width of the ridge; such a ridge will not tend to cut or hurt the user. The tongue and other soft tissue in the mouth will give and bend some distance around the ridge so long as the ridge is not too tall for the width of the ridge engaging the tissue. In one exemplary embodiment, ridges 6022 have a width W that is preferably about 0.8 mm and a height H about 0.6 mm. Nevertheless, a wide range of relative sizes are possible.

Additionally, ridge 6022 also includes a base 6028 where the ridge is fixed to surface 6017a. In a preferred construction, base 6028 defines a width W1 that is at least as large as the height H of the ridge. In this way, the ridges do not experience undue bending as they are dragged over the tongue. Rather, ridges 6022 are stably supported so that they tend to remain generally in a protruding orientation. As a result, edges 6025, 6027 are stably supported to dig into recesses in the tongue to effectively remove bacteria and debris.

Figure 61:
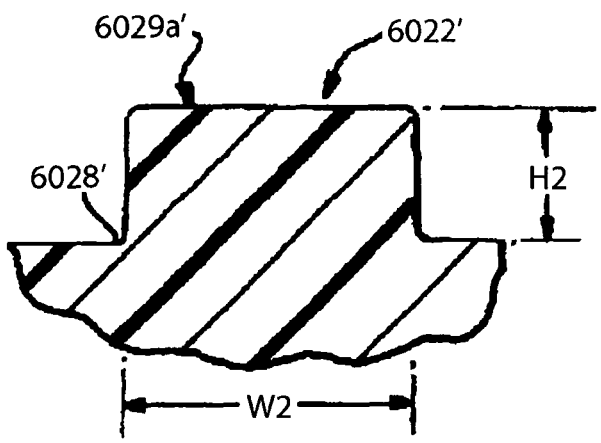
FIG. 61 is a partial cross sectional plan view of an alternative structure taken along line II-II of FIG. 59.

Alternatively, the ridges could have other shapes. For example, FIG. 61 illustrates ridges 6022' that are substantially wider than they are tall, i.e., base 6028' and contact region 6029a' each has a width W2 that is substantially greater than the height H2 of the ridge. In one example, the width is about twice the distance of the height. The increased width to height ratio of ridge 6022' provides for a stiffer, smaller ridge to effectively cleanse the tongue. Such ridges are beneficial in that they reduce the size of the head, which is preferred by some users. A shorter, wider ridge also further reduces the prospect of users injuring themselves. Moreover, such ridges can be made of softer materials without losing the desired stability.

Figure 61A:
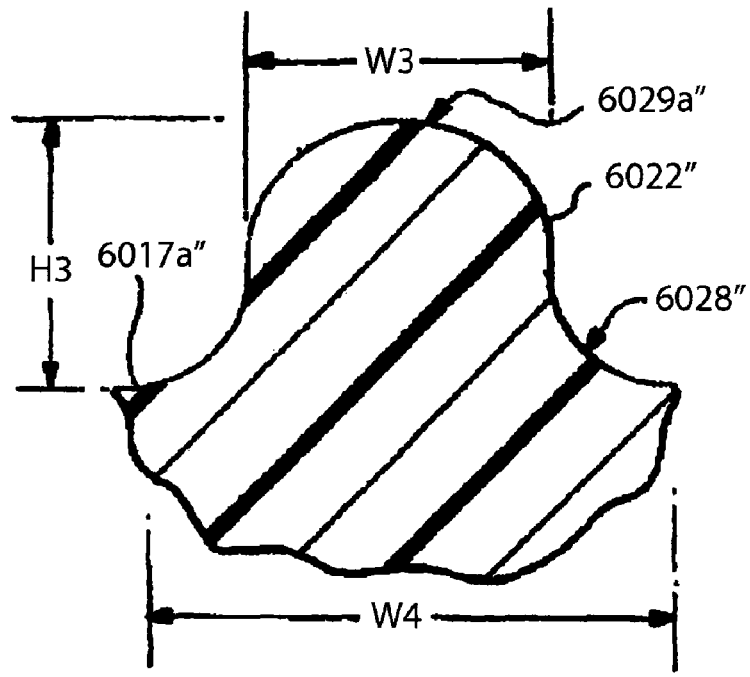
FIGS. 61a and 61b are partial cross-sectional views of alternative ridge shapes for the embodiment of FIG. 59.
Figure 61B:
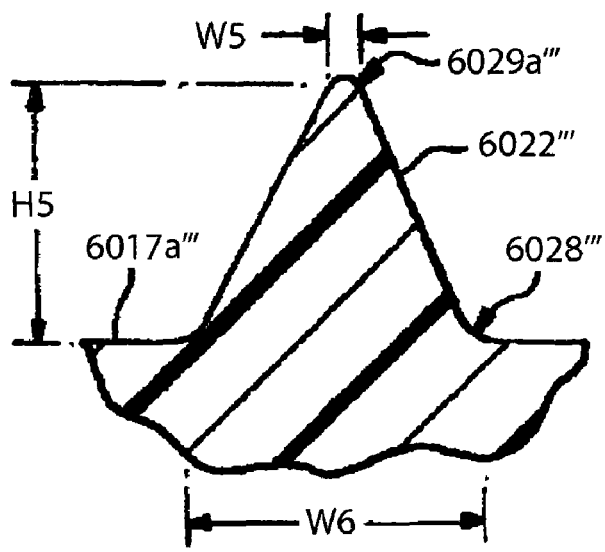

In another example (FIG. 61a) ridge 6022" has a rounded distal end. Accordingly, the contact region 6029a" has an arcuate, convex surface to engage the tongue or other soft tissue. In this example, the contact region 6029a" (i.e., the surface adapted to engage the tongue) has a width W3 that is at least as large as the height H3 of the ridge. In this embodiment, the base 6028" of ridge 6022" also has a width W4 that is at least as large as height H to present a stable ridge. Of course, numerous variations may be formed in the shape of the ridge while maintaining the benefits of the invention.

In addition, the ridges may be formed to gain only some of the benefits of the invention. For instance, ridge 6022''' can be formed to taper to a narrowed distal end 6029''' (FIG. 3b). In this instance, contact region 6029a''' has a width W5 that is less than the height H5. However, the base 6028''' of ridge 6022''' has a width W6 that is at least as large as the height to form a stable ridge construction.

Although the illustrated ridges have all been shown to extend generally perpendicular from surface 6017a, they could be inclined relative to surface 6017a. A perpendicular extension is preferred to provide effective cleaning regardless of whether the tongue cleaner is pushed or pulled over the tongue. The sides 6024, 6026 could also be inclined, curved, angular, irregular or otherwise shaped. Additionally, the ridges could project from a non-planar surface. As one example, surface 6017a and ridges 6022 could have an undulating configuration.

Regardless of the cross-sectional shape of the ridge, each ridge 6022 is preferably curved to define a concave side 6024 facing toward handle 6014 and a convex side 6026 facing in the opposite direction. Although ridges that are continuously curved are preferred (FIG. 59a), such concave-shaped ridges could be defined by non-continuous ridges (FIG. 59b) or angular ridges (FIG. 59c). Further, in one preferred construction, ridges 6022 are progressively less curved as they are formed farther from handle 6014. In one illustrated construction (FIGS. 59 and 59a), the ridges are generally concentric to each other curving generally about a common point near the connection of handle 6014 to head 6012.

In use, the user grips the handle and typically pulls the tongue cleanser repeatedly over the tongue from back to front so that the concave sides 6024 are scraped against the tongue to effectively gather and remove bacteria and debris on the tongue. Alternatively, the user may also commonly move the tongue cleanser forward and backward over the tongue. In either event, the different curvatures of the ridges enable aligned segments of the ridges (i.e., along lines generally parallel to longitudinal axis 6030) to engage the tongue surface at different angles for effective cleaning of the tongue. Nevertheless, the tongue cleansing ridges can be moved over the tongue in a number of ways to clean the tongue.

Figure 62:
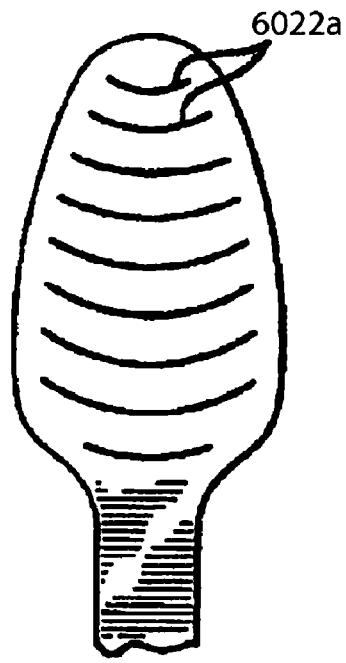
FIGS. 62-75 are each a top plan view of the head illustrating an alternative ridge construction for the embodiment of FIG. 59.
Figure 63:
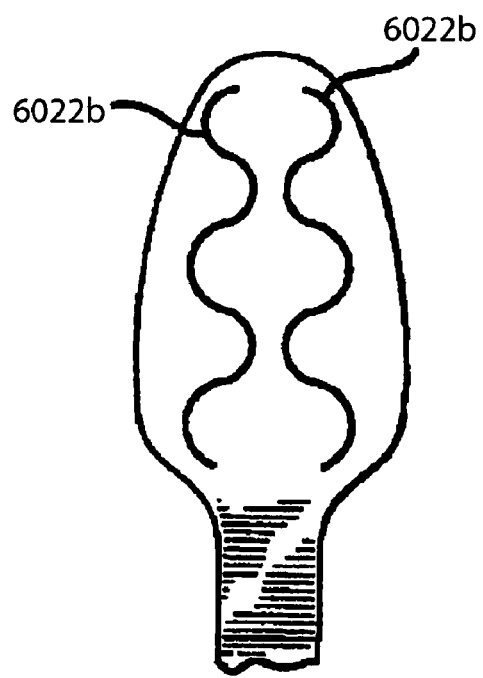
Figure 64:
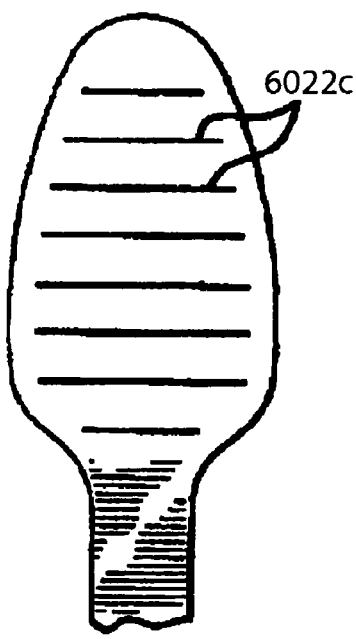
Figure 65:
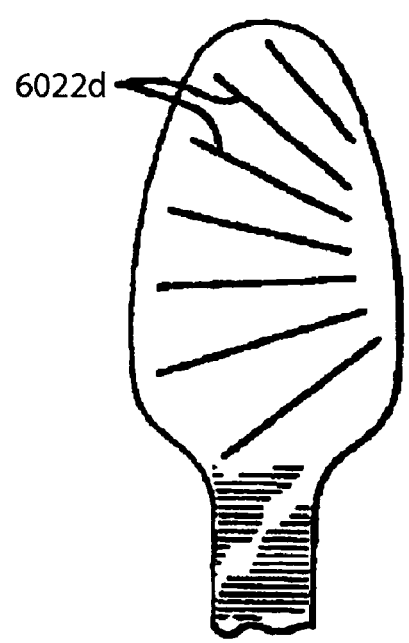
Figure 66:
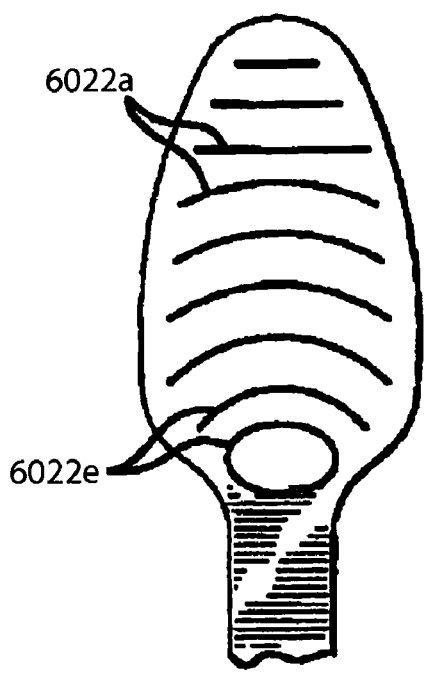
Figure 67:
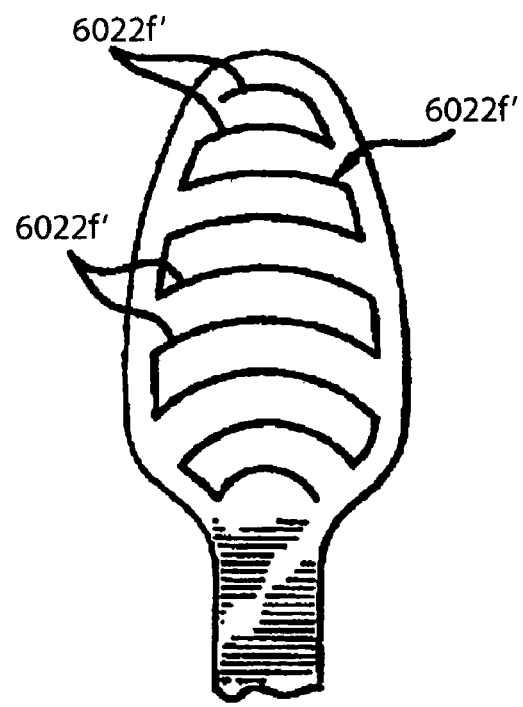
Figure 68:
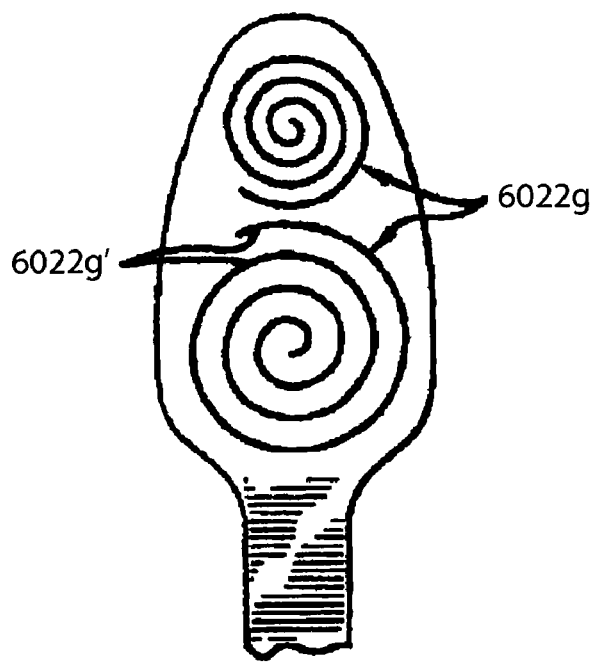
Figure 69:
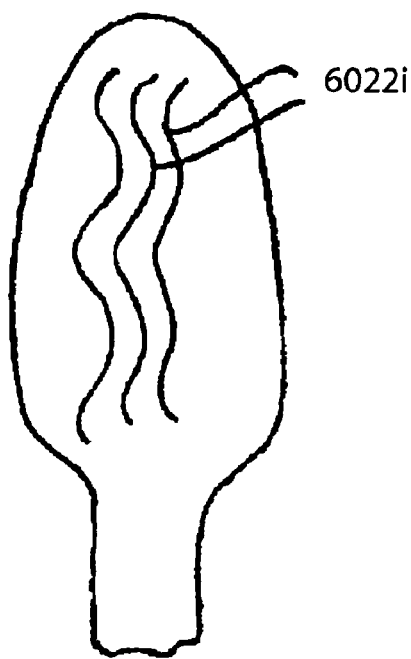
Figure 70:
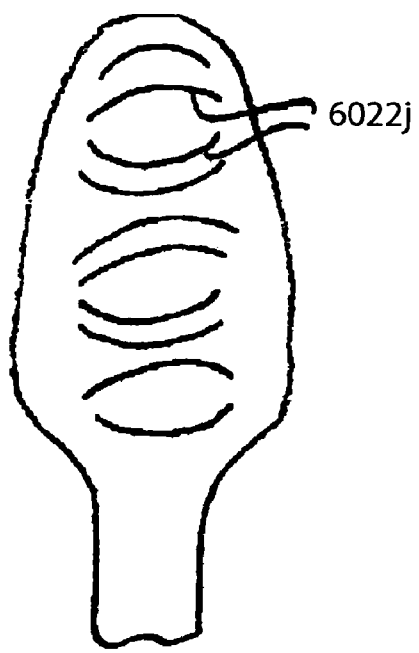
Figure 71:
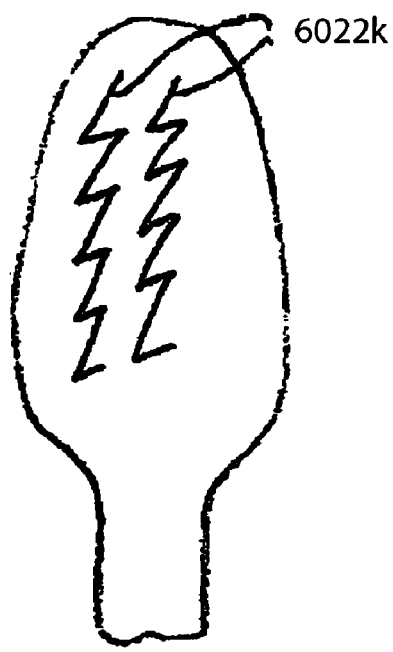
Figure 72:
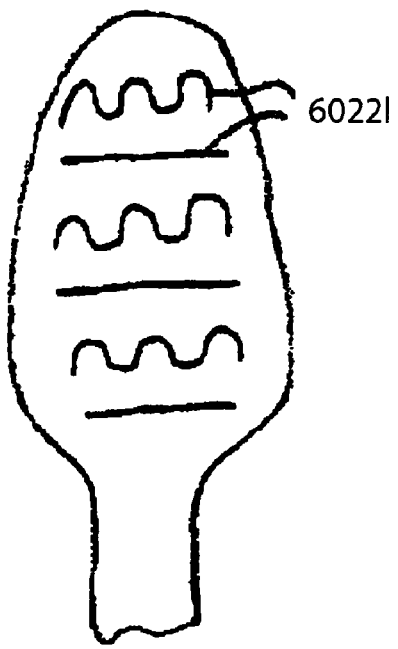
Figure 73:
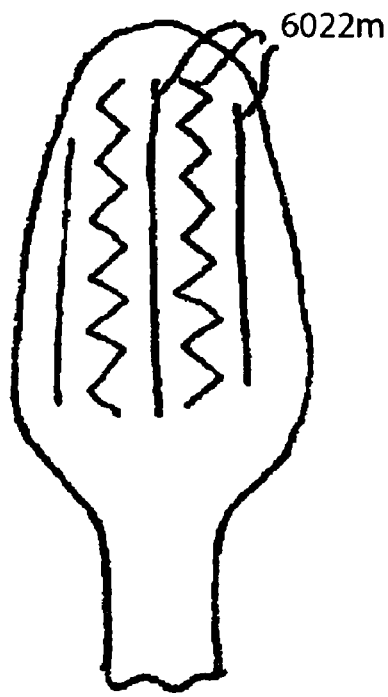
Figure 74:
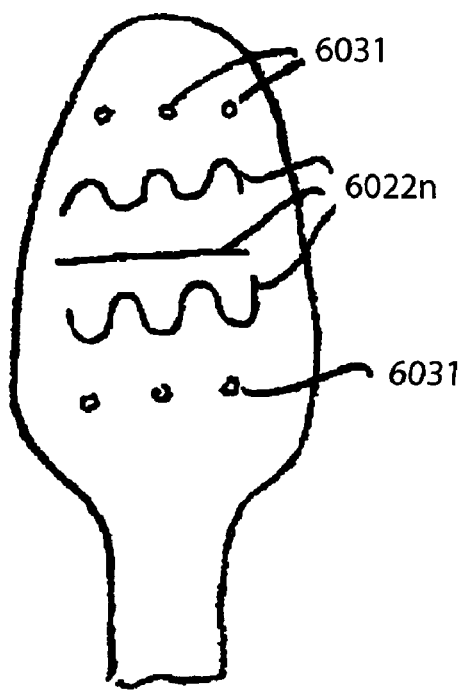
Figure 75:
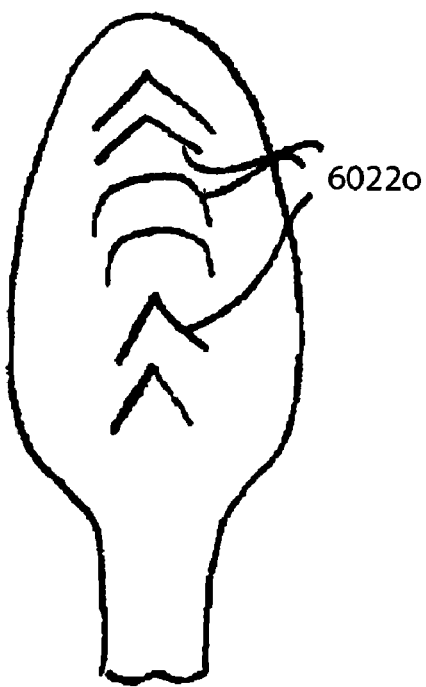
Figure 76:
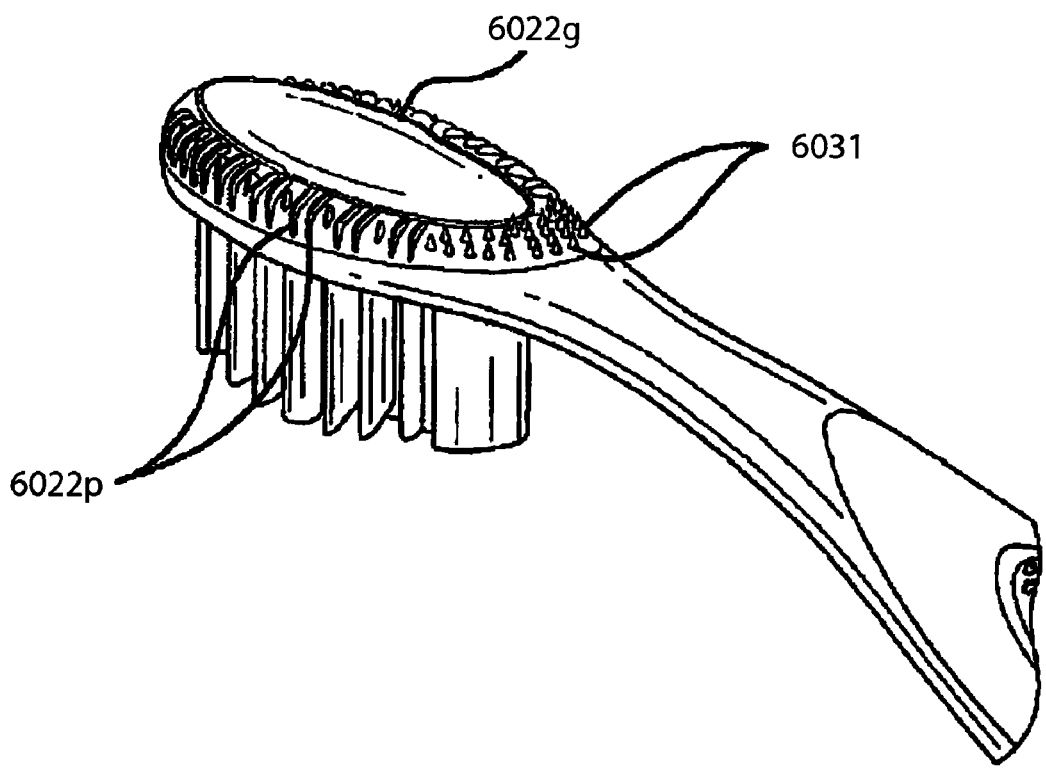
FIGS. 76-80 are each a perspective view of a further embodiment of a head of an oral care implement in accordance with the invention.
Figure 77:
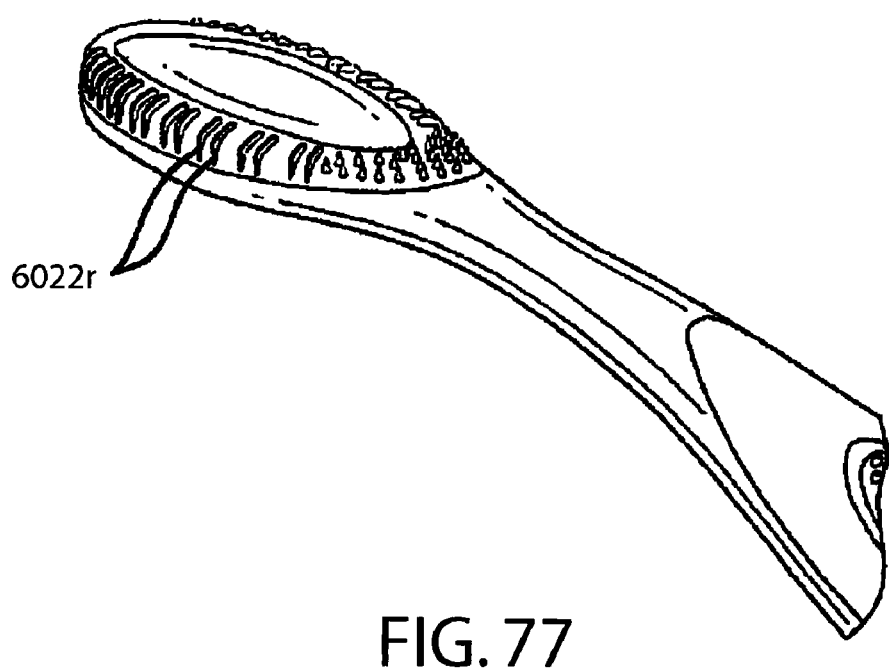
Figure 78:
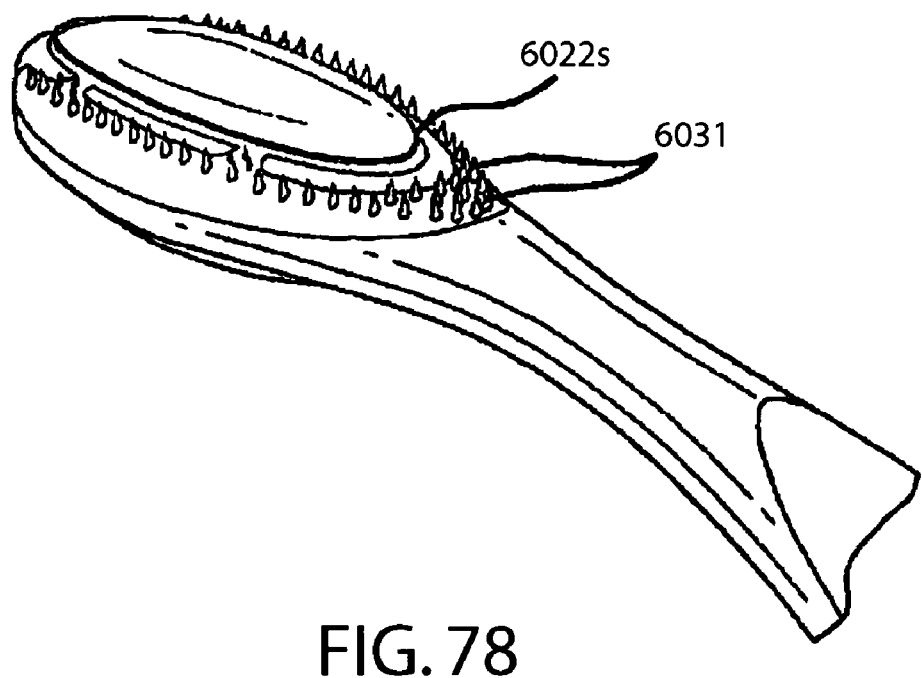
Figure 79:
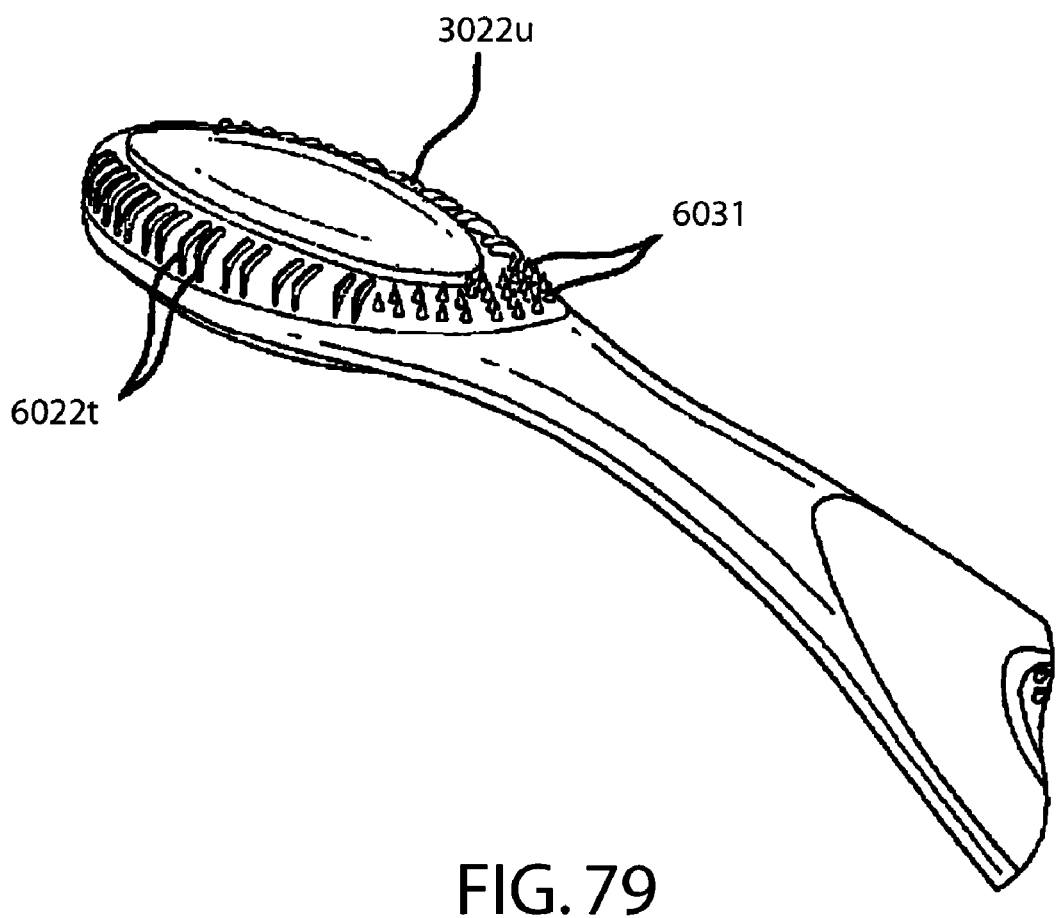
Figure 80:
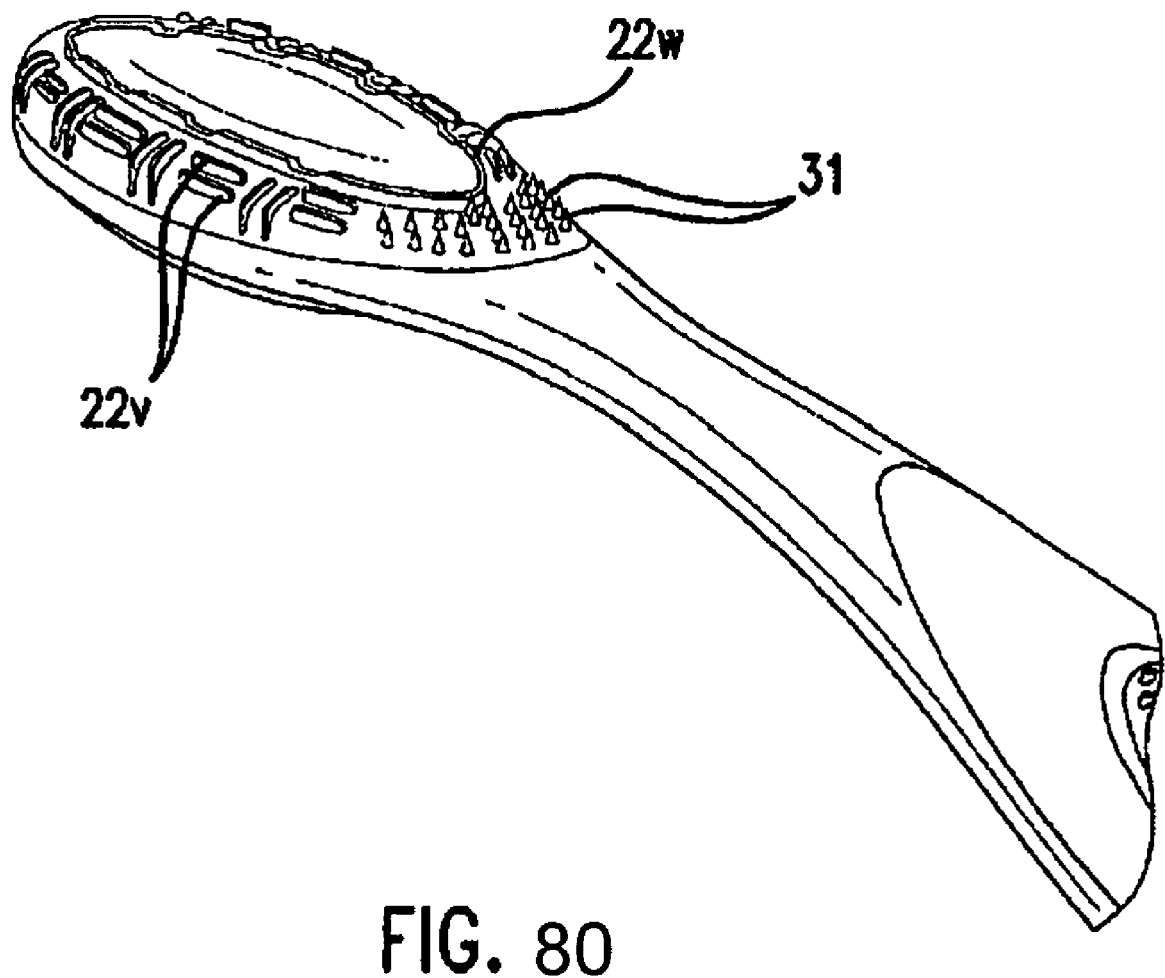

Further, other ridge constructions could be used. For example, the oral care implement could include ridges 6022a that are reversed so that the concave sides face away from the handle (e.g., FIG. 62), ridges 6022b, 6022g, 6022i, 6022j, 6022s with different curved shapes (e.g., FIGS. 63, 68-70, and 78), ridges 6022c, 6022d, 6022k and 6022r that are linear (e.g., FIGS. 64, 65, 71 and 77), ridges 6022e, 6022l, 6022m, 6022n and 6022o that include a mixture of curved and linear ridges (e.g., FIGS. 66 and 72-75), or one continuous ridge member 6022f, 6022g forming successive ridges 6022f, 6022g', (e.g., FIGS. 67 and 68). The ridges could be non-concentric or curved at all the same radius of curvature. While the ridges preferably extend substantially across the entire side 6017 of head 6012, they could extend only part way across the head. For example, ridges 6022p, 6022r, 6022t, 6022v could be provided only along the sides of surface 6017a (FIGS. 76-77 and 79-80). Ridges along the sides of head 12 could also be used with central ridges; i.e., side ridges 6022p, 6022t, 6022v could be used with a central ridge(s) such as an oval or partially oval ridge 6022q, 6022u, 6022w (FIGS. 76, 79 and 80), any of the ridge patterns illustrated in FIGS. 59a-c and 62-75, or another ridge pattern. Any of the ridges could also be used with various projections, e.g., conical projections 6031 (see, e.g., FIGS. 74 and 76-80). Regardless of whether the ridge 6022 each form a continuous segment across the head (e.g., FIG. 59*a*) or is defined by aligned ridge sections 6022*h* separated by gaps 6023 (e.g., FIG. 59*b*), they are in this application each considered a ridge. Also, regardless of whether successive ridges 6022 are separated (e.g., FIG. 59*a*) or interconnected to define a single ridge member 6022*f* (e.g., FIG. 67), the successive sections extending laterally across the hand are each considered to be a ridge. Concepts of this invention can be used in connection with ridges having virtually any shape or orientation along surface 6017*a*.

Figure 59:
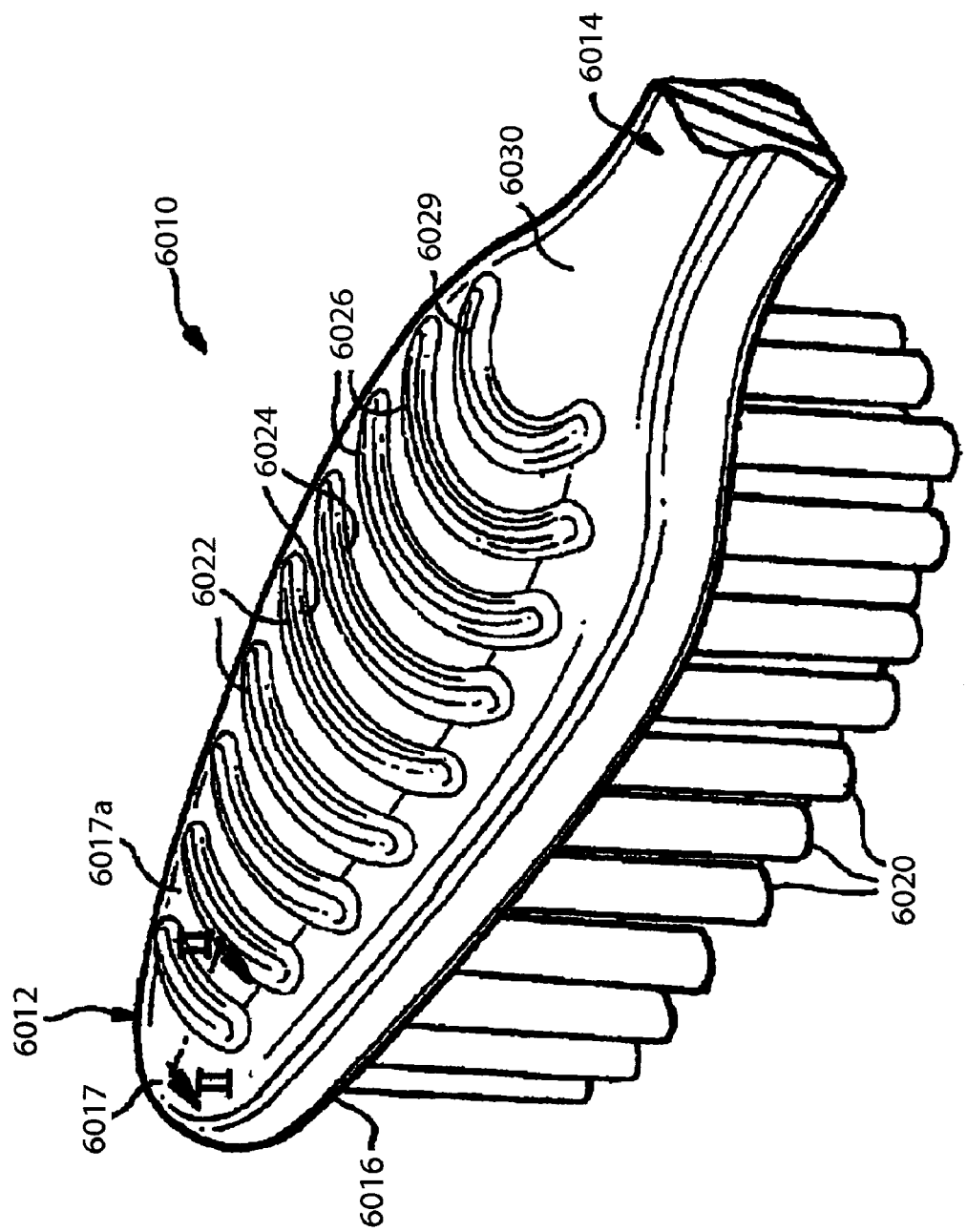
FIG. 59 is a perspective view of a head of a further toothbrush embodiment in accordance with the present invention.
Figures 59A, 59B:
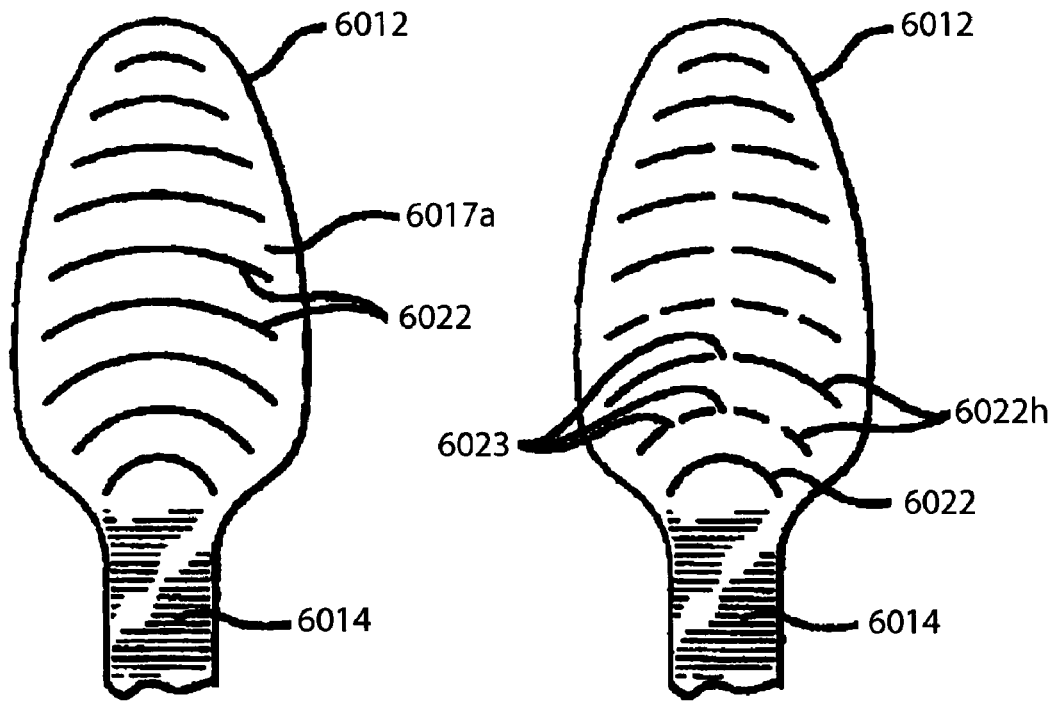
FIG. 59a is a top plan view of the head of FIG. 59.
FIGS. 59b and 59c are top plan views of the head illustrating alternative concave-shaped ridges for the head of FIG. 59.
Figure 59C:
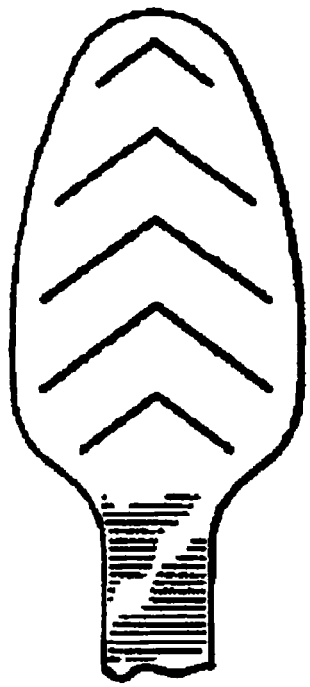

As shown in FIGS. 59 and 60, head 6012, handle 6014 and ridges 6022 can be molded together as a one-piece member of the same material, for example, polypropylene. Nonetheless, other arrangements are possible. For example, head 6012 could be detachable from handle 6014. Further, ridges 6022 could be separately molded, glued or otherwise attached to side 6017 of head 6012. The ridges as well as the head and the handle could each be made from a material different from the other parts. Soft materials, such as TPE or the like, can be fixed to head 6012 to form the ridges (see, e.g., FIGS. 76-80). The ridges could be made of virtually any known material used to make oral care implements.

FIGS. 81-89 illustrate an oral care implement in the form of a toothbrush 8100 having an improved handle 8103 and a head 8105 with bristles or other tooth engaging elements extending form surface 8107. While reference is made to a toothbrush with an improved handle, other oral care implements, such as inter-proximal picks, flossing tools, plaque scrapers, tongue and soft tissue cleansers/massagers and the like, may use the same handle.

Handle 8103 is provided for the user to reliably grip and manipulate the toothbrush. Handle 8103 includes ergonomic features which provide a high degree of control for the user while maintaining comfort. In a preferred construction (FIGS. 81-89), handle 8103 includes a base 8300, a grip body 8403, and a gripping member 8407. These components cooperatively form a grip portion 8400 by which the user holds and manipulates the toothbrush. For optimum comfort and control, grip portion 8400 includes three segments 8111, 8113, 8115. A rear segment 8115 forms a portion that generally fits comfortably within the palm of the user. A front segment 8111 forms a portion that generally fits comfortably between the user's thumb and index finger. A narrow transition segment 8113 connects the front and rear segments 8111, 8115.

In a preferred construction, front segment 8111 is inclined relative to rear segment 8115 to define an inclined portion positioned for comfortable gripping and to facilitate a desired offset positioning of the head relative to the palm gripping region 8115. The angle θ of the incline is preferably 23 degrees, but may range approximately between 5-40 degrees. This feature allows improved control of the handle during brushing in which the head 8105 can be more desirably positioned within the mouth to engage the tooth cleaning elements 8200 against the teeth.

In the preferred embodiment, front and rear segments 8111, 8115 are widened sections that are joined by a narrowed portion 8113 to form an undulating structure which is more reliably and comfortably held within the user's hand. Further, this wide construction of the palm and finger gripping regions 8111, 8115 requires less fine motor control by the user and is, hence, easier to hold and manipulate. In addition, front segment 8111 transitions into neck 8116 which, in turn, supports head 8105. In a preferred embodiment, base 8300 includes a gripping region 8301 that corresponds to grip portion 8400, the neck 8116, and the head 8105 to define an oral engaging region.

Under a normal use position, grip portion 8400 is grasped by a user with the fingers engaging the handle 8103 so that the thumb is on one side and the index finger and other fingers are positioned on the opposite side. Front segment 8111 of grip portion 8400 includes grip body 8403 having opposing sides 8405, 8404 preferably for engaging the thumb and index finger of a user. Grip portion 8400 further includes a rear segment 8115 which enables reliable gripping of the toothbrush 8100 with the third through the fifth fingers of the user's hand in a normal use position. While a normal use position is discussed, the features of the toothbrush could be employed by a user having less fingers or a user which holds the toothbrush in other ways.

Figure 81:
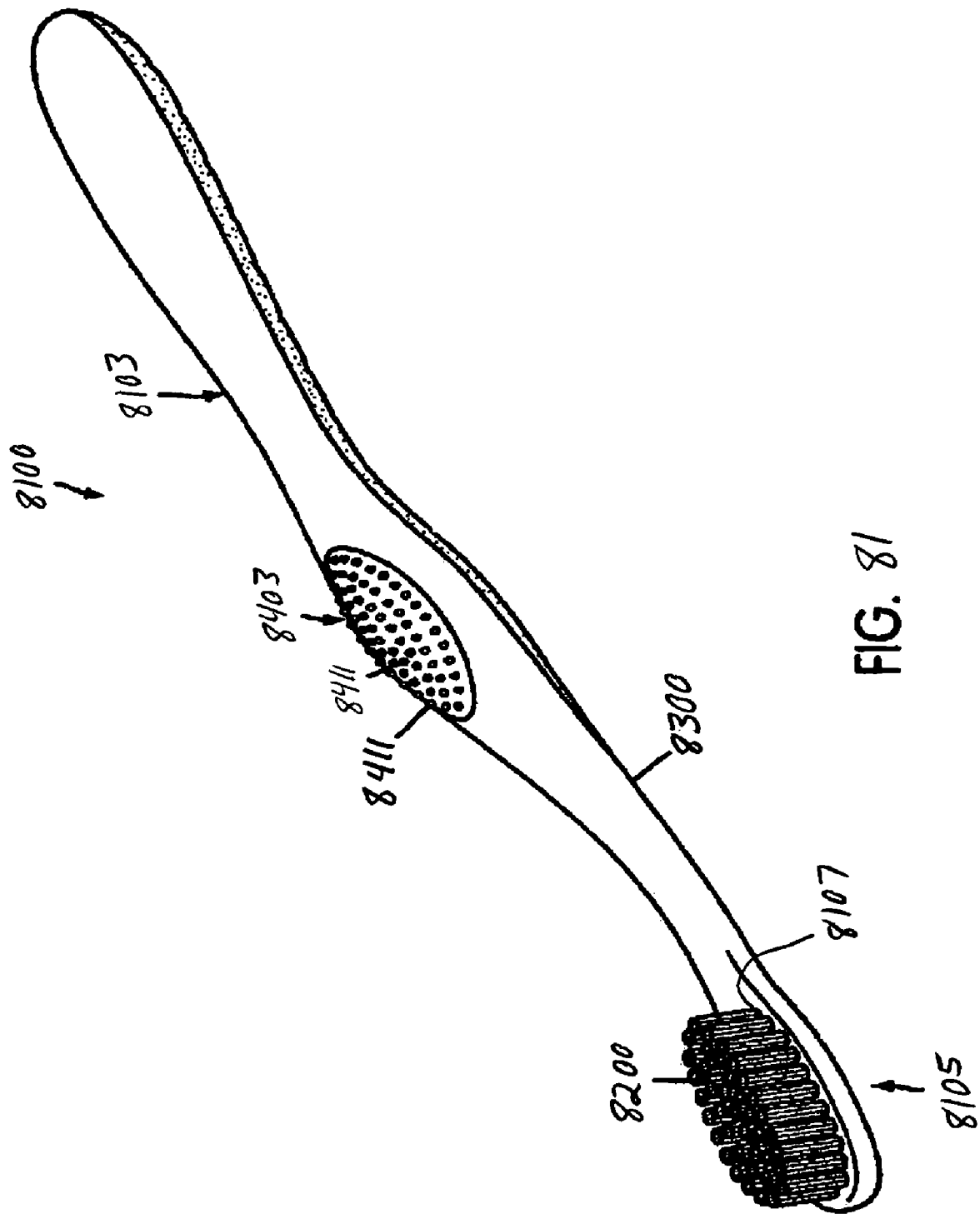
FIG. 81 is a perspective view of an oral care implement according to one or more aspects of another embodiment of the present invention.
Figure 84:
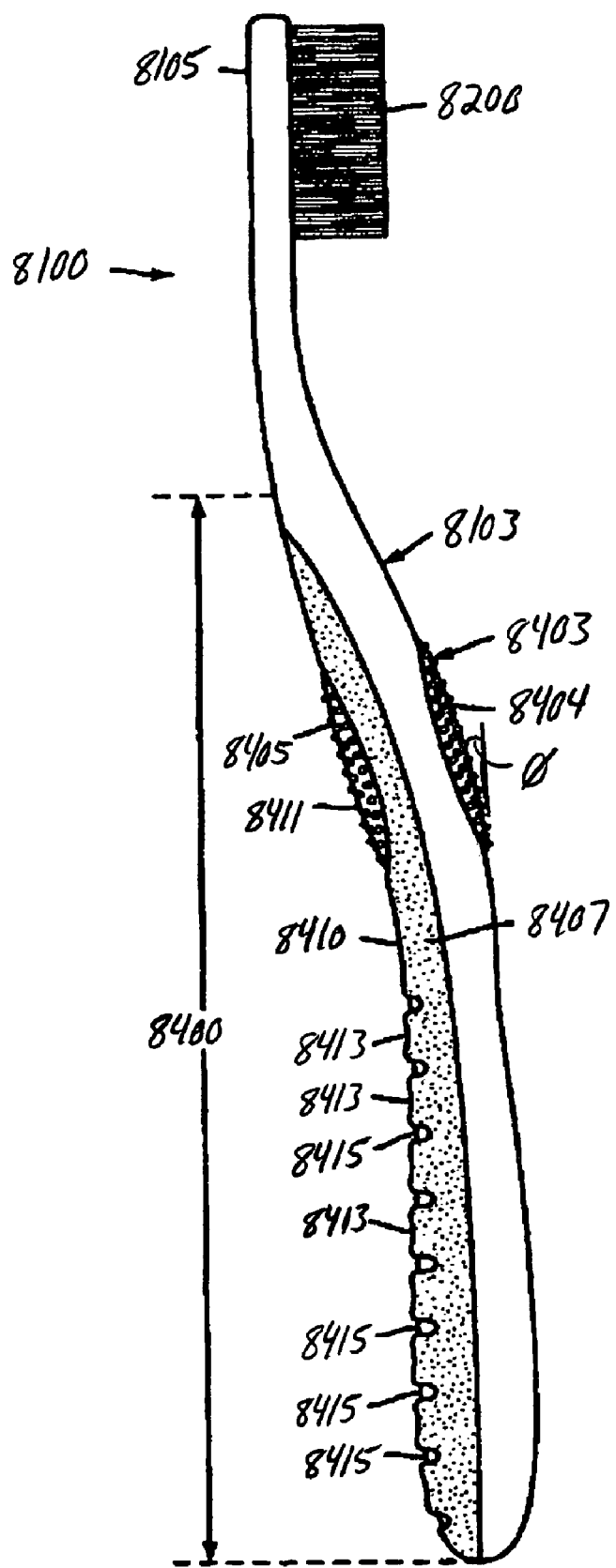
FIG. 84 is a side view of the oral care implement of FIG. 81.
Figure 88:
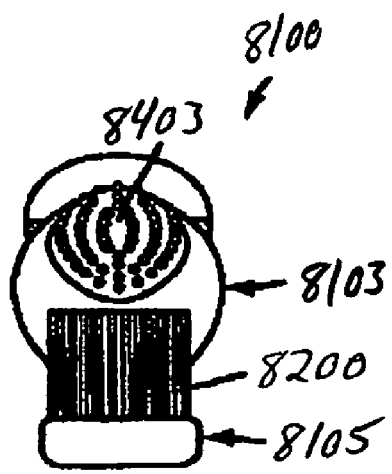
FIG. 88 is a forward axial view of the oral care implement of FIG. 81.
Figure 89:
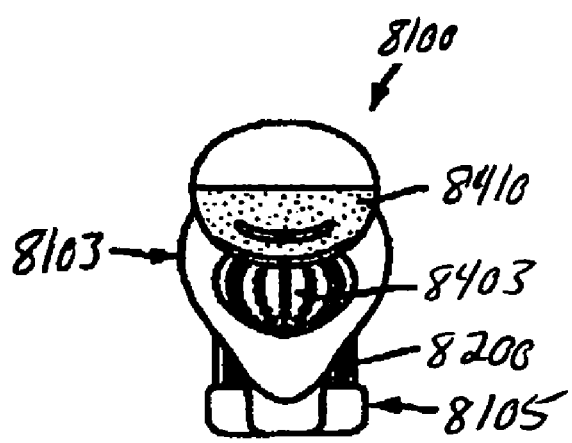
FIG. 89 is a forward axial view of the oral care implement of FIG. 81.

In one preferred construction, front section 8111 includes a soft, resilient grip body 8403 fixed within aperture 8303 of base 8300. As shown in FIGS. 88 and 89, front section 8111 has the widest transverse dimension of any other part of handle 8103. As shown in FIGS. 81 and 84, aperture 8303 occupies more than one-half of the transverse dimension across front section 8111 of handle 8103. Nevertheless, other constructions are possible. As an example only, grip body 8403 may occupy a smaller portion of the transverse dimension, such as one-third of the transverse dimension of front section 8111. Nevertheless, the width and length of aperture 8303 may be adjusted as desired and other parts of handle 8103 may be as wide as or wider than front segment 8111.

Referring to FIGS. 86-87, in one construction, aperture 8303 extends through base 8300 to mount grip body 8403. Aperture 8303 includes a sidewall geometry 8305 for the retaining and dynamic positioning of the resilient grip body 8403 during use of the toothbrush. While grip body 8403 is preferably molded into aperture 8303, it could be premolded and mounted into aperture 8303. In a preferred construction, grip member 8403 is a soft, resilient element formed of a thermoplastic elastomer (TPE) which fills the aperture 8303. To provide optimum comfort as well as control benefits, the elastomeric material preferably has a hardness durometer measurement ranging between A11 to A15 Shore hardness. Nevertheless, the hardness of the elastomer could also range between A8 to A24 Shore hardness. Other materials outside this hardness range could also be used. As an example, one preferred elastomeric material is styrene-ethylene/butylene-styrene (SEBS) manufactured by GLS Corporation. Nevertheless, other manufacturers can supply the SEBS material and other materials could be used.

Referring to FIGS. 81-85, resilient grip body 8403 preferably has a generally bulbous shape that bulges out of aperture 8303 and which resembles an oval or elliptical shape. The bulbous shape of the resilient grip body 8403 enables the user to reliably roll and control the handle 8103 between the thumb and index fingers during use. Grip body 8403 could also be non-bulging or have any number of shapes, such as circular, a true oval shape and the like.

Referring to FIGS. 86-87, aperture 8303 preferably includes a peripheral shoulder or rim 8304 for supporting grip body 8403. Sidewall 8305 of aperture 8303 extends between opposing outer surfaces of base 8300 and includes inclined surfaces 8309, 8310 inside of the periphery 8306 of aperture 8303. The inclined surfaces 8309, 8310 extend from the outer surfaces towards a rounded edge surface 8311 which is the narrowest part of the aperture 8303. This construction, in conjunction with the soft, resilient nature of grip member 8403, provides a weight shifting feature which improves control of the handle 8103 during use.

Resilient grip body 8403 further helps attenuate the brushing force applied to the oral surfaces to prevent gum recession, loss of tooth enamel or to provide for a more comfortable brushing experience. When the toothbrush is used against the oral surfaces, such as the teeth, reaction forces are transferred to the resilient grip body 8403. The elastomeric material dampens the forces against the head 8105 which reduces the brush pressure applied to the teeth and soft tissue surfaces, such as the gums. In a preferred construction, elastomeric material of the resilient grip body 8403 is enabled to flow and shift within aperture 8303. Net pressure applied by the user's fingers is transferred to grip body 8403 so that the inclined surface 8309, 8310 enables the elastomeric material to flow to the narrowest portion of the aperture. Hence, some of the elastomeric material squeezes past rounded edge surface 8311 to the other side of the aperture while under pressure. The shifting of the material to the other side of the aperture causes a slight shift in the mass centroid of the resilient member 8403 to counter balance the brushing forces. Thus, grip body 8403 balances handle 8103 enabling it to "float" in the hand of the user and reduce the brushing forces applied by the head 8105.

In one preferred construction, grip body 8403 has a multiplicity of finger grip protrusions 8411 (FIGS. 81-85). Finger grip protrusions 8411 provide a tactile feature to increase the friction on the user's finger surfaces and thus enhance the user's ability to grip the handle, particularly under wet conditions. Finger grip protrusions 8411 are preferably provided in a desired conical or frusto-conical shape for improved grip performance. Of course, other roughened surfaces could be used.

Referring to FIGS. 86 and 87, rear segment 8115 is preferably formed by base 8300 and gripping member 8407. In one preferred embodiment, base 8300 defines a relatively rigid support structure which is at least partially overlain by an elastomeric gripping member 407. While gripping member 8407 is shown as a single unitary member or layer, it could be formed by separate independent parts or sections.

Base 8300 along rear segment 8115 includes at least one projection, and preferably a plurality of spaced projections. While the projections could have virtually any shape, they are preferably in the form of spaced, elongate, transverse projections or ribs 8315. In the preferred embodiment, ribs 8315 are generally parallel with respect to each other and generally symmetrical in relation to the longitudinal axis a-a of rear segment 8115. The projections 8315 are preferably linear and span laterally between the longitudinal sides 8313, 8314 of handle 8103, although they may have different transverse lengths. The transverse length of each projection 8315 generally matches the width at the longitudinal location along the handle 8103; although the ribs are preferably slightly short of the actual width of handle segment 8115 at any one location so as to be covered on the sides by gripping member 8407. Since ribs 8315 span the width of segment 8115, they each have varying lengths due to the variations in the width of handle segment 8115. While nine projections are shown, the inventive aspects may be obtained by other numbers of projections.

In a preferred arrangement, a receiving region 8317 is defined between each of the adjacent transverse projections 8315. The receiving regions 8317 are configured to retain and hold a layer of suitable gripping member 8407, such as a thermoplastic elastomer (TPE) or other similar materials used in oral care products. In a preferable construction, receiving regions 8317 have a transverse arcuate base surface 8319 with a transverse groove or depression 8321. The arcuate base surface 8319 extends between the longitudinal sides of base 8300. When a gripping member 8407 is applied to the base, grooves 8321 create concaved regions 8413 in grip surface 8410 to improve the tactile performance of the toothbrush handle (see FIG. 84). While horizontal or straight projections 8315 are illustrated, the projections 8315, alternatively, may be any number of shapes or orientations with respect to the longitudinal axis a-a. For example, the projections 8315 may be chevron shaped, circular, oval, elliptical, rectangular, or triangular or other shapes. The orientation of the projections 8315 may also be off-axis from the longitudinal axis a-a to form an asymmetrical relationship. The projections 8315 may be regularly or randomly spaced on base 8300 for the intended gripping performance. As shown in FIG. 87, a peripheral portion of base 8300 has a peripheral groove 8323 arranged to receive and hold a layer of the grip material for suitable use with the toothbrush.

Figure 85:
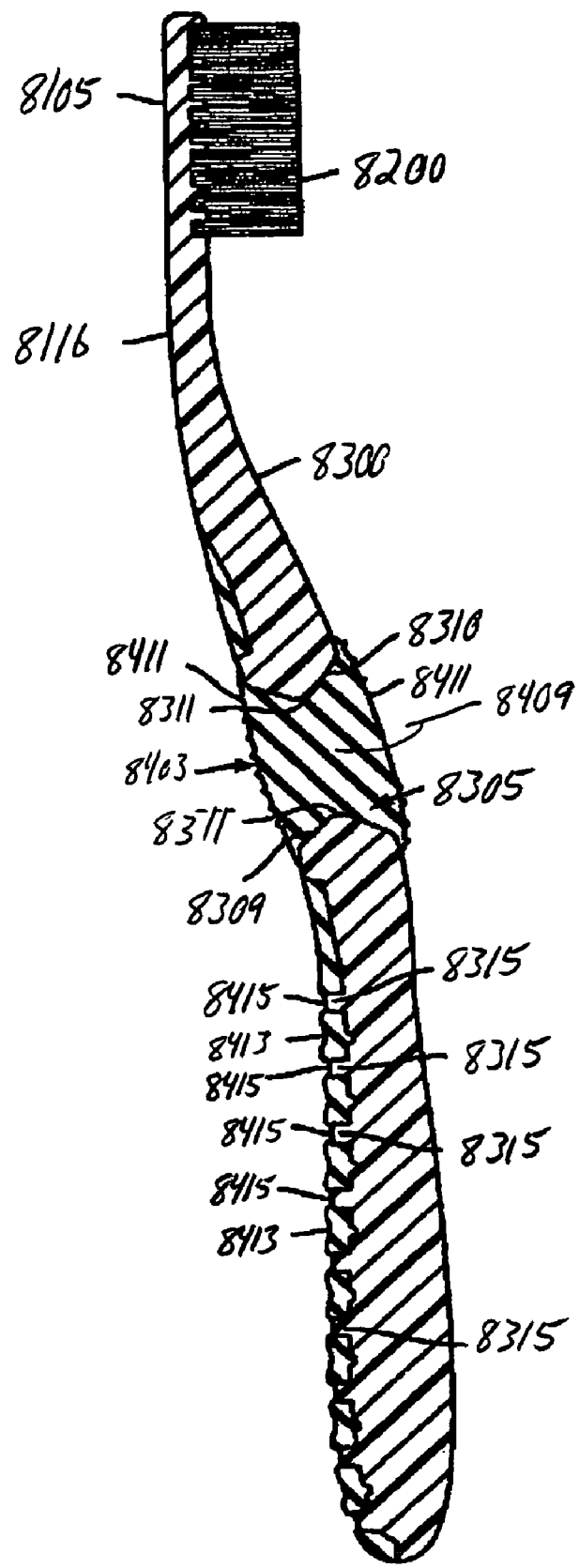
FIG. 85 is a section view of the oral care implement taken along line 85-85 in FIG. 83.

Referring to FIGS. 82, 84 and 85, gripping member 8407 is fixed to base 8300 to provide several gripping features to improve performance. In one aspect, gripping member 8407 has a grip surface 8410 with at least one and preferably a plurality of spaced openings, preferably in the form of elongate transverse slots 8415, which expose portions of base 8300. In this way, the outline shape of slots 8415 is formed by the peripheral shape of projections 8315 of base 300 (FIGS. 86 and 87). To form slots 8415, suitable injection molding equipment mates with the top surfaces of the projections 8315 to prevent overmolding of ribs 8315 and any undesired deflection of base 8300 during the molding process. This enables the top surfaces of the projections 8315 to be exposed after the molding process.

To provide comfort as well as control benefits, the elastomeric material of the grip surface 8410 may have a hardness durometer measurement ranging between A13 to A50 Shore hardness, although materials outside this range may be used. A preferred range of the hardness durometer rating is between A25 to A40 Shore hardness. While an injection molded construction is preferred, a suitable deformable thermoplastic material, such as TPE, may be formed in a thin layer and attached to base 8300 with an appropriate adhesive or by other means. Irrespective of the manufacturing process, ribs 8315 are preferably recessed relative to gripping surface 8410, i.e., a suitable thickness of elastomeric material is used to control the depth of the slot 8415 as measured from the top of the grip surface 8410 to the top of the projection (e.g., the exposed portion of base 8300). In a preferred construction, the depth of the slots along axis a-a is about 0.5 mm. These transverse slots 8415 prevent slippage of the handle 8103 by enabling portions of the user's fingers to slightly protrude into the depth of the slot 8415. Additionally, slots 8415 channel water away from the fingers tips during wet operational conditions. Air is also able to enter the slots during brushing to provide some evaporative effect.

In another aspect, the grip surface 8410 includes concaved regions 8413 between each slot 8415 to further improve the grip performance of handle 8103. The concaved regions 8413 are preferably created by a suitable thickness of the elastomeric material during the injection molding process filling into the transverse grooves 8321 in base 8300, but could be formed by other means (FIGS. 86 and 87). While base surface 8319 is preferably arcuate in a transverse direction, the base surface may be horizontal or take on other shapes.

In one preferred construction, resilient grip body 8403 has a different hardness as compared to the hardness of the grip surface 8410. Generally, the material of grip body 8403 is softer than the material forming the grip surface 8410. In this manner, the handle 8103 may be provided different grip features to complement the particular control need. For example, the handle 8103 may have a soft forward portion with a shock absorption advantage and a slightly harder aft portion with a comfort and control advantage. The material of the resilient grip body 8403 and grip surface 8410 are preferably each a thermoplastic elastomer.

The inventive aspects may be practiced for a manual toothbrush or a powered toothbrush. In operation, the previously described features, individually and/or in any combination, improve the control and grip performance of oral implements. Other constructions of toothbrush are possible. For example, head 8105 may be replaceable or interchangeable on handle 8103. Head 8105 may include various oral surface engaging elements, such as inter-proximal picks, brushes, flossing element, plaque scrapper, tongue cleansers and soft tissue massages. While the various features of the toothbrush 8100 work together to achieve the advantages previously described, it is recognized that individual features and sub-combinations of these features can be used to obtain some of the aforementioned advantages without the necessity to adopt all of these features in an oral care implement.

FIGS. 90-98 show additional embodiments of the invention that further illustrate the combinability of various aspects, features and functions disclosed herein into single oral care implement configurations. FIGS. 90-98 disclose oral care implement configurations that provide tongue cleanser functionality and include handle gripping features. As such, oral care implements 90-98 generally include the aspects discussed along with FIGS. 38, 39 and 45-81 pertaining to soft tissue cleansers (e.g., tongue cleansers), as well as the aspects discussed along with FIGS. 84-89 pertaining to handle features. Further, it is understood that other features may be used along with these configurations.

As an example of potential embodiments based on combinations of features disclosed herein, the mechanical drive features discussed along with FIG. 1-5 and/or tooth cleansing features discussed throughout the specification may be combined with the soft tissue cleansers of FIGS. 90-98. Thus, as illustrated in FIGS. 98A-C, embodiments of the invention include any one of heads 9014, 9214, 9414, 9614 and 9514 discussed hereafter in combination with handle 1 and neck part 4 shown in FIGS. 1-4 instead of bristle-carrying head part 3 shown in FIGS. 1-5. These embodiments provide powered oral care implement configurations that can provide enhanced cleansing benefits. For example, such combination devices can provide the functions of two devices in a single device. Further, these devices can simultaneously provide dual cleaning functionality. For instance, toothbrush features may be used to clean a user's teeth while the soft tissue cleanser features simultaneously clean soft tissues, such as the inside of a user's cheeks.

Figure 90:
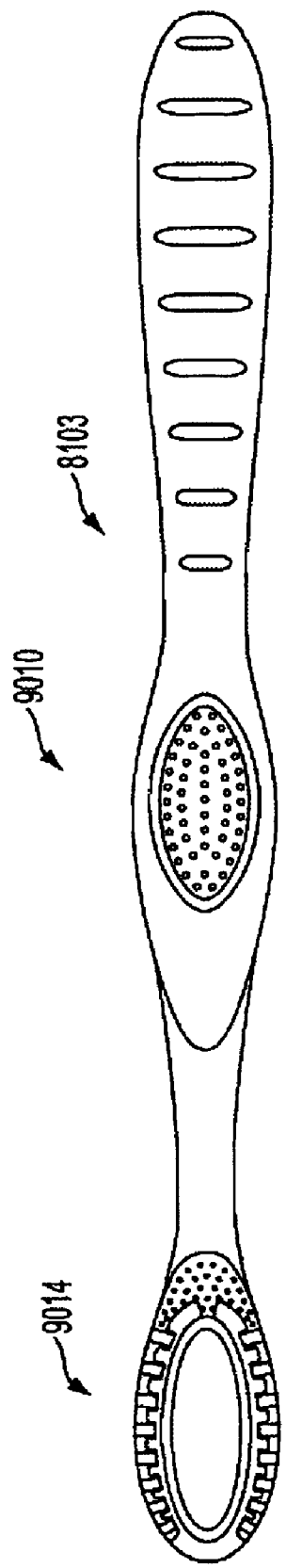
FIG. 90 is top plan view of a further oral care implement in accordance with the present invention.
Figure 91:
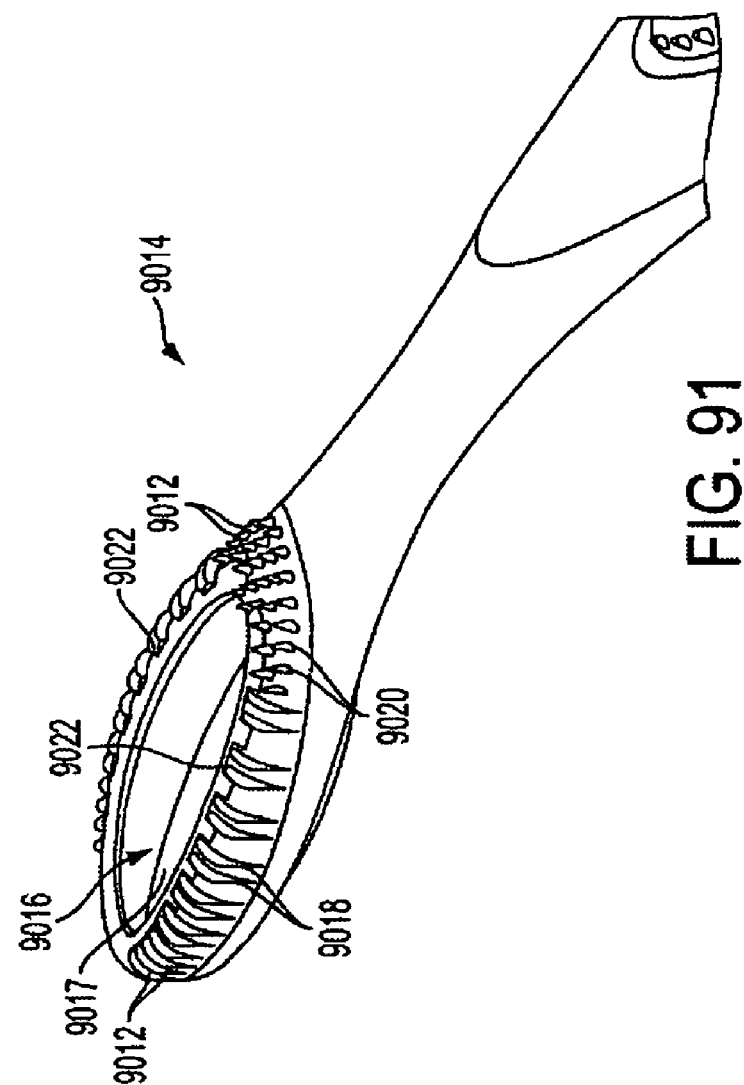
FIG. 91 is partial perspective view of a head portion of the oral care implement of FIG. 90.

FIGS. 90 and 91 disclose a soft tissue cleanser 9010 for removing microbial and other debris from the soft tissue of a user's mouth, such as the user's tongue and inside of their cheeks and lips. As shown, cleanser 9000 generally includes a handle 8103 attached to a head 9014. The head and handle may be molded together as a one-piece member of the same material, for example, polypropylene or another thermoplastic elastomer. In addition, the head may be detachable from the handle. In the configuration shown, handle 8103 is the handle of oral care implement 8100 discussed along with FIGS. 81-89.

In general, head 9014 includes a plurality of tissue engaging elements 9012 disposed about a central portion 9016 of the head. Elements 9012 include projections in the form of ridges 9018 and nubs 9020, which extend from the head to engage the soft tissue in a user's mouth. The ridges and nubs may be separately molded, glued or otherwise attached to head 9014. In addition, they may be integrally formed therewith. The ridges and nubs could each be made from a material different from each other and/or different from other parts. Soft materials, such as TPE or the like, can be fixed to head 9014 to form the ridges. However, a harder material or virtually any known material used to make oral care implements may be appropriate for the ridges and nubs. Ridges 9018 and nubs 9020 could have a variety of shapes, patterns, cross-sections, configurations, etc., as discussed along with FIGS. 38, 39 and 45-81.

Central portion 9016 is shown as a generally elliptically-shaped region on a face of head 9014 about which cleaning elements 9012 are disposed that has a bottom surface 9017 generally disposed below the tips of the ridges and nubs. It is understood, however, that the central portion may have a variety of shapes, sizes and depths. In the configuration shown, central portion 9016 is a relatively shallow depression that extends into the head about 10% to about 30% of the thickness of the head. In another configuration, the central portion may be shallow and may not extend into the head. For instance, the central portion may be formed by a surface 9017 of the head upon which the cleaning elements are disposed along with a ring of cleaning elements 9012 bounding the central portion. In such a configuration, the central portion would be a depressed region with respect to the protruding cleaning elements disposed about it, but would not otherwise extend into the head. In other configurations, the central portion may be depressed into the head about 0 to 10% of its thickness, or it may be depressed about 30% to 50% or more of its thickness.

As shown, surface 9017 may be continuous to provide a non-interrupted boundary for the central portion 9016 and it may be relatively smooth. In alternate configurations, surface 9017 may include interrupting or undulating features, such as one or more notches, contour features, or features to permit partial flow of materials therethrough, such as a mesh or screen. In addition, surface 9017 may include irregular features, such as cleaning elements, projections, etc.

Central portion 9016 and the ring of protruding cleaning elements 9012 cooperate to translate a downward force applied by the user into a concentrated force at the cleaning elements. Thus, the cleaning elements penetrate more deeply into the user's soft tissue than would be provided by a relatively uniform contact surface or a uniform field of cleaning elements, such as the configuration provided by tissue cleanser 4800 shown in FIG. 45. This permits ridges 9018 and nubs 9020 to more effectively penetrate the soft tissues. In an alternative construction in which the head includes toothbrush features on an opposite side thereof (see FIG. 98), the ring of protruding cleaning elements configuration can effectively engage soft tissues in the inside of a user's cheeks and lips without the user applying significant force in the direction of the ring, as may be the case when the user cleans their teeth via the toothbrush features. As further shown, central portion 9016 includes a bottom surface 9017 for contacting soft tissue during use. The bottom surface can act as a guide to limit the penetration depth of the nubs and ridges when excessive downward force is applied by the user. In addition, it can provide a collector for micro debris scraped during use of the oral care implement.

A variety of ridges, nubs, or other cleaning element configurations may be used. In the configuration shown for oral care implement 9010, ridges 9018 are generally oriented away from a center of central portion 9016 in a radial manner. Central portion 9016 is elliptically shaped and is aligned with a longitudinal axis of handle 8103. As such, ridges 9018 are oriented generally perpendicular to the longitudinal axis of the handle, which provide blades oriented transverse to the scraping direction for most users. When a user scrapes the oral care implement 9010 forward and backward in a direction substantially parallel to the longitudinal axis of handle 8103, ridges 9018 act as small blades to scrape micro debris from the soft tissue. As also shown in FIGS. 90 and 91, the ridges may be angled upward toward engagement with soft tissue during use. Thus, inner portions 9022 of ridges 9018 engage soft tissue when the user applies a light downward pressure, and the ridges more fully engage the soft tissue when additional pressure is applied. As such, variable cleaning and scraping functionality is provided as desired by the user via their selection of a downward force.

As further shown in FIGS. 90 and 91, nubs 9020 are provided along a portion of central portion 9016 disposed between handle 8103 and a distal end of head 9014. Nubs provide concentrated penetration into the user's soft tissue during use. In addition, in their location along central portion 9016 as shown in FIG. 91, they can encourage dislodged micro debris into central portion 9016 to be captured therein and removed by the user. It is understood that various nub configurations, positions and orientations, as well as ridge and central portion configurations, positions and orientations, can provide various advantages and functionality.

FIGS. 92 and 93 illustrate another possible configuration of cleaning elements in an example oral care implement 9210. Oral care implement 9210 generally includes the same aspects and features of oral care implement 9010, except that it additionally includes a narrow protrusion 9224 erected around the perimeter of central portion 9216. The narrow protrusion may be a semi-flexible, "blade-like" structure that assists with scraping a user's tongue or other soft tissue. In alternative constructions, it may be a rigid structure or relatively flexible structure. Narrow protrusion 9224 may be made from a flexible or semi-flexible, thermoplastic elastomer, a hard plastic structure or another rigid material, such as metal. As shown in FIGS. 92 and 93, blade-like protrusion 9224 may be continuous structure disposed about the central portion. In other configurations, it may a partial structure, such as an arc. It may also exist apart from or without the central portion, and it may include a truncated shape or shapes. The blade-like protrusion provides an effective blade for scraping micro debris from a user's soft tissue. In a continuous configuration, it may further encourage micro debris scraped from the user's soft tissue to be retained within central portion 9216.

FIGS. 94 and 95 illustrate another possible configuration of cleaning elements in an example oral care implement 9410. Oral care implement 9410 generally includes the same aspects and features of oral care implement 9210, except that cleaning elements 9412 only include nubs 9420 disposed about central portion 9416. The nubs provide concentrated penetration into the user's soft tissue, which can act to dislodge micro debris and thereby assist blade-like protrusion 9416 with scraping micro debris from the user's soft tissue.

FIGS. 96 and 97 illustrate another possible configuration of cleaning elements in an example oral care implement 9610. Oral care implement 9610 generally includes the same aspects and features of oral care implement 9010, except with respect to cleaning elements 9612 and blade-like structure 9624. As shown, cleaning elements 9612 include a combination of blades 9618 extending substantially radially from the center of central portion 9616, as well as blades 9630 oriented substantially perpendicular to blades 9618. The mixture of blades in alternating orientations can improve scraping effectiveness of the oral care implement. In addition, blade-like structure 9624 includes notches 9632 spaced about its blade, which can further improve the scraping effectiveness of the oral care implement.

Figure 98:
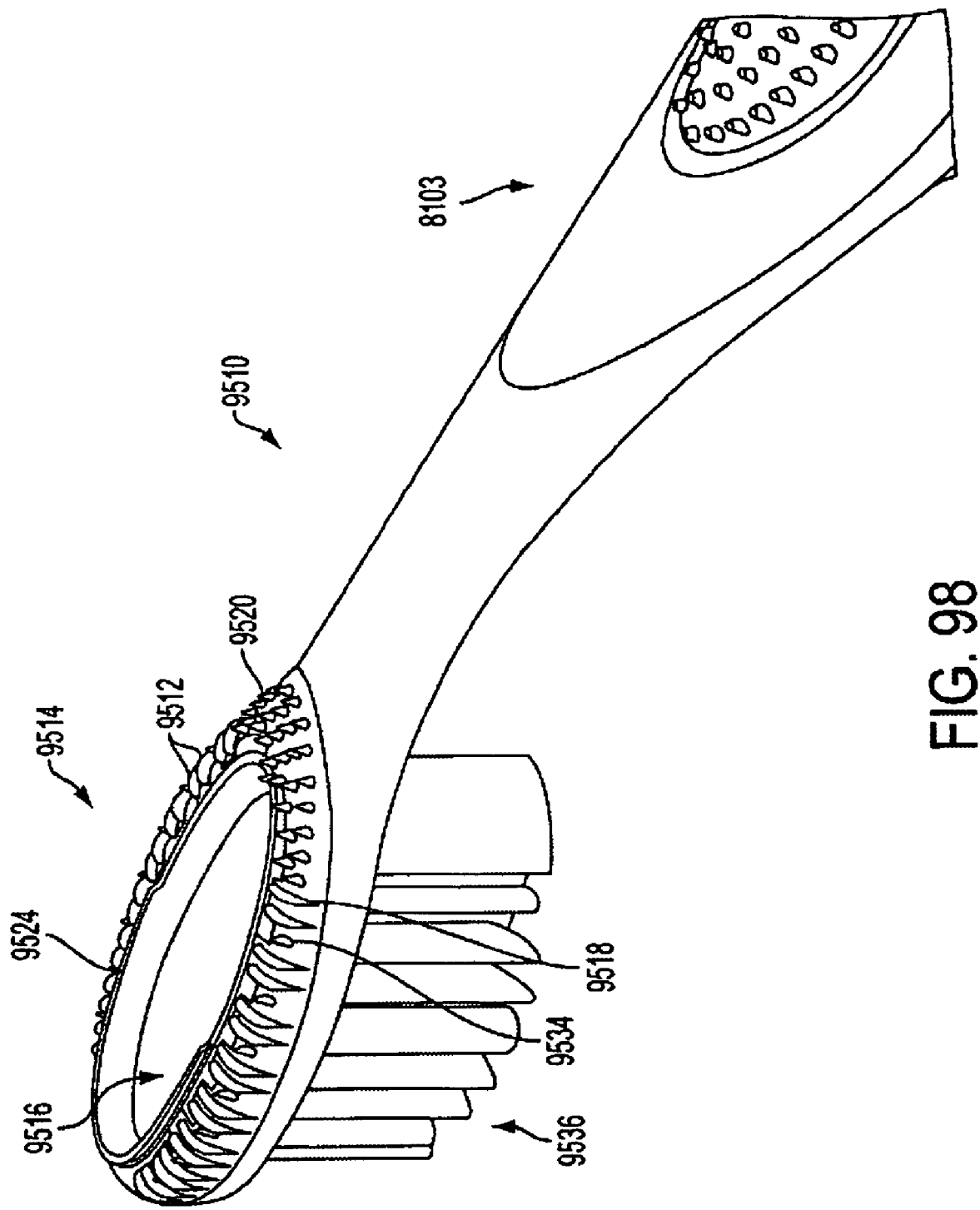
FIG. 98 is partial perspective view of a head portion of yet another oral care implement in accordance with the present invention.
Figure 98A:
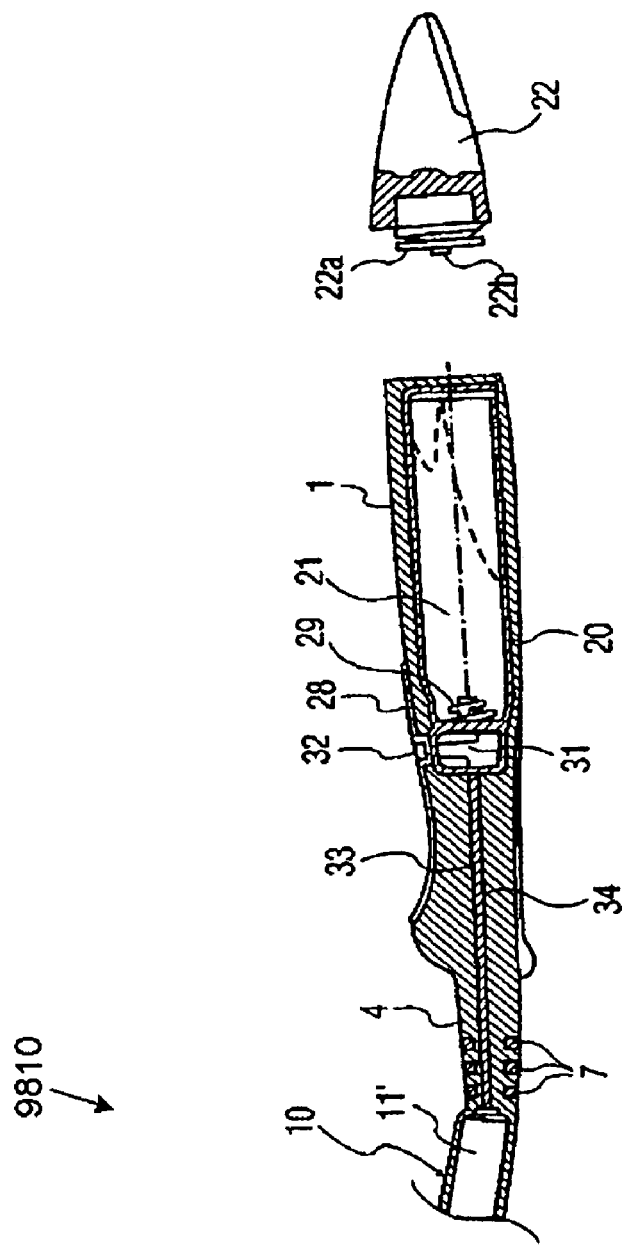
FIGS. 98A-C show an additional oral care implement in accordance with the invention.
Figure 98B:
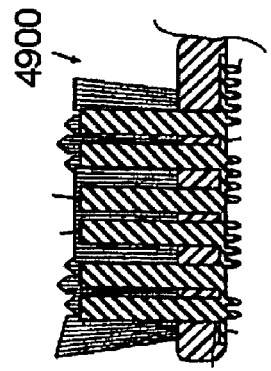
Figure 98C:
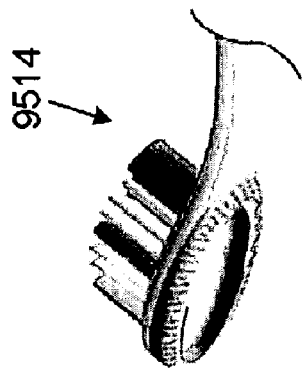

FIG. 98 illustrates a further possible configuration of an oral care implement. Oral care implement 9510 generally includes the same aspects and features of oral care implement 9210, except with respect to cleaning elements 9512 and blade-like structure 9524. As shown, cleaning elements 9512 include short blades 9534 interposed between pairs of longer blades 9518, which can further improve the scraping effectiveness of the blades. In addition, blade-like structure 9524 is truncated such that it only extends around a distal portion of central portion 9516, which can encourage dislodged micro debris to be retained within central portion 9516 when the oral care implement 9510 is scraped across soft tissue while being withdrawn from the user's mouth. Oral care implement 9510 further includes tooth cleaning elements 9536 extending from an opposite side of the head from cleaning elements 9512. Nubs 9520 are also provided. Thus, a user can use the single oral care implement 9510 to effectively clean their teeth and to scrape their tongue, for which the handling of the implement is improved via gripping features of handle 8103. In addition, the user can simultaneously clean their teeth via cleaning elements 9536 and engage the inside of their cheeks and lips via 9512.

FIGS. 98A-C show an oral cleaning implement 9810 that includes a dual function head 4900 or 9514, and a powered handle 1. The handle is generally the same as powered handle 1 discussed along with FIGS. 1-5, which may be used to move or vibrate tooth cleaning features of the head, and/or soft tissue cleanser features of the head. Although the head is shown as either head 4900 or head 9514, the head may include any one of heads 9014, 9214, 9414, 9614 and 9514 or other dual function heads. As discussed above, these embodiments can provide enhanced cleansing benefits by simultaneously engaging proximate oral surfaces, such as cleaning a user's teeth, and cleaning or stimulating the inside of their cheeks and lips. Moreover, such combination devices can provide the functions of two devices in a single device.

As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims. Further, as noted above, it is intended that oral care implements according to the invention and associated methods may utilize various combinations of aspects, features and configurations discussed within the application.

What is claimed is:

1. An oral care implement comprising:
   a handle;
   a head formed of a rigid material and having a first face, the head having a proximal end connected to the handle, a distal end, lateral sides and a longitudinal axis;
   a soft tissue cleanser in the form of a ring of elastomeric material defining a central opening, the soft tissue cleanser disposed on the first face of the head so that a central portion of the head is exposed via the central opening;
   the soft tissue cleanser comprising a plurality of projections protruding outwardly from the ring of elastomeric material;
   wherein the projections of the soft tissue cleanser adjacent the sides of the head comprise first ridges oriented to generally radiate from the central opening: and
   wherein the projections of the soft tissue cleanser adjacent the proximal end of the head are nubs.

2. The oral care implement of claim 1, wherein the central portion is a depression formed into the first surface of the head having, a bottom surface and a side wall formed from the rigid material.

3. The oral care implement of claim 2, wherein at least a portion of the side wall of the depression extends above the first face of the head so as to form an elongated scraper.

4. The oral care implement of claim 3, wherein the elongated scraper is a curved ridge located adjacent the distal end of the head.

5. The oral care implement of claim 3, wherein the elongated scraper is a substantially continuous boundary around the central portion.

6. The oral care implement of claim 1, wherein the projections of the soft tissue cleanser along the sides of the head further comprise second ridges oriented to be generally transverse to the first ridges.

7. The oral care implement of claim 1, wherein the ridges each include a top edge angled away from the first face to provide increasing engagement with the soft tissues as the first face is pressed into the soft tissues.

8. The oral care implement of claim 1, wherein the ring of elastomeric material is substantially elliptically shaped.

9. The oral care implement of claim 1, further comprising tooth cleansing elements extending from a second face of the head for cleaning a user's teeth.

10. The oral care implement of claim 9, wherein the tooth cleansing elements extend in a direction substantially opposite the direction in which the projections protrude to permit simultaneous engagement of a user's teeth via the tooth cleansing elements along with engagement of soft tissues opposed to the teeth via the soft tissue cleanser.

11. The oral care implement of claim 9, further comprising a drive mechanism for moving at least one of the tooth cleansing elements and projections.

12. The oral care implement of claim 11, wherein the drive mechanism includes a mechanical vibratory device.

13. The oral care implement of claim 11, wherein the drive mechanism simultaneously moves both the tooth cleansing elements and projections.

14. An oral care implement comprising:
a handle;
a head having a first face and an opposite second face;
a soft tissue cleanser for cleansing soft tissue in a user's mouth disposed on the first face of the head, the soft tissue cleanser comprising:
a ring of projections protruding outward from the first face for dislodging microbial and other debris from the soft tissue, the ring of projections comprising nubs and ridges;
an elongate ridge projecting outward from the first face for dislodging microbial and other debris from the soft tissue, the elongate ridge disposed within the ring of projections; and
a central portion on the first face substantially bordered by the elongate ridge and by a surface of the first face, the central portion having a depression having a bottom surface located at a depth below the first face; and
tooth cleansing elements extending from the second face in a direction substantially opposite the elongate ridge and the ring of projections.

15. An oral care implement comprising:
a handle;
a head formed of a rigid material and having a first face and a central axis generally aligned with the handle and traversing a central portion of the first face:
an oval depression formed into the first face of the head, the depression having a bottom surface and a continuous upstanding side wall that encloses the depression;
a soft tissue cleanser disposed on the first face of the head for cleansing soft tissue in a user's mouth, the soft tissue cleanser comprising soft tissue cleanser elements disposed generally symmetrically about the central axis: and
wherein the at least a portion of the side wall of the depression extends above the first face so as to form an elongated ridge; and
wherein the soft tissue cleanser elements include nubs and ridges projecting from the first face.

16. The oral care implement of claim 15, wherein the soft tissue cleanser elements include a ring of projections protruding outwardly from the first face.

17. The oral care implement of claim 16, wherein the ring generally forms an ellipse.

18. The oral care implement of claim 15, further comprising tooth cleansing elements extending from a second face of the head for cleaning a user's teeth.

19. The oral care implement of claim 18, wherein the tooth cleansing elements extend in a direction substantially opposite the direction in which the soft tissue cleanser elements are oriented outwardly from the first face to permit simultaneous engagement of a user's teeth via the tooth cleansing elements along with engagement of soft tissues opposed to the teeth via the soft tissue cleanser.

* * * * *